United States Patent
Lorentsen et al.

(10) Patent No.: US 10,253,304 B2
(45) Date of Patent: *Apr. 9, 2019

(54) COMPOSITION AND METHODS COMPRISING A XYLANASE ENZYME VARIANT

(71) Applicant: DUPONT NUTRITION BIOSCIENCES APS, Copenhagen (DK)

(72) Inventors: Rikke Hoeegh Lorentsen, Randers (DK); Susan Arent Lund, Brabrand (DK); Jacob F. Cramer, Højbjerg (DK); Igor Nikolaev, Palo Alto, CA (US); Wilhelmus Van Der Kleij, Leiden (NL)

(73) Assignee: DUPONT NUTRITION BIOSIENCES APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/114,886

(22) PCT Filed: Jan. 30, 2015

(86) PCT No.: PCT/EP2015/051974
§ 371 (c)(1),
(2) Date: Jul. 28, 2016

(87) PCT Pub. No.: WO2015/114108
PCT Pub. Date: Aug. 6, 2015

(65) Prior Publication Data
US 2016/0340664 A1  Nov. 24, 2016

(30) Foreign Application Priority Data

Jan. 31, 2014 (GB) .................................. 1401680.2

(51) Int. Cl.
*C12N 9/24* (2006.01)
*C12P 19/02* (2006.01)
(Continued)

(52) U.S. Cl.
CPC ............ *C12N 9/2482* (2013.01); *A23K 10/12* (2016.05); *A23L 2/382* (2013.01); *C12P 19/02* (2013.01);
(Continued)

(58) Field of Classification Search
None
See application file for complete search history.

(56) References Cited

FOREIGN PATENT DOCUMENTS

WO    2011109524 A2    9/2011

OTHER PUBLICATIONS

GenBank Accession No. ADM34973.1, published Aug. 26, 2010.*
(Continued)

*Primary Examiner* — Richard C Ekstrom

(57) ABSTRACT

The present invention provides hemicellulytic enzyme variants. Specifically, the present invention provides xylanase variants having one or more modifications as compared to a parent xylanase enzyme resulting in at least one improved property. In addition, the present invention provides compositions comprising a xylanase variant of the invention. The present invention also provides methods of degrading hemicellulotic material, including arabino-xylan using compositions comprising a xylanase variant of the invention.

24 Claims, 16 Drawing Sheets
Specification includes a Sequence Listing.

(51) Int. Cl.
  C12P 19/14    (2006.01)
  A23K 10/12    (2016.01)
  A23L 2/38     (2006.01)
  A61K 38/00    (2006.01)

(52) U.S. Cl.
  CPC ....... *C12P 19/14* (2013.01); *C12Y 302/01008* (2013.01); *A23V 2002/00* (2013.01); *A61K 38/00* (2013.01); *Y02E 50/17* (2013.01)

(56) References Cited

OTHER PUBLICATIONS

GenBank Accession No. ENH76371.1, published Apr. 9, 2013.*
International Search Report, PCT Application No. PCT/EP2015/051974, dated Aug. 6, 2015.
Database Uniprot (Online), "Beta-Xylanase From Fusarium Oxysporum", ECO:0000256 Rule Base: RU361174), XP002741186, Retrieved From EBI Accession No. UNIPROT N1S2Q7, Database Accession No. N1S2Q7 Sequence (2013), pp. 1-4.
Hokanson et al., "Engineering Highly Thermostable Xylanase Variants Using an Enhanced Combinatorial Library Method", Protein Engineering Design and Selection, vol. 24, No. 8 (2011), pp. 597-605.

* cited by examiner

Figure 5

(SEQ ID NO: 1)

ATTCCCACCGCCATCGAGCCCCCGCCAGGCTGCCGACAGCATCAACAAGCTGATCAAGAACAAGGGCAAGCTCTACTA
CGGAACCATCACCGACCCCAACCTGCTCGGCGTCGCAAAGGACACCGCCATCATCAAGGCCGACTTTGGCGCCGTTA
CCCCCGAGAACTCGGGCAAGTGGGACGCCACCGAGCCCAGCCAGGGCAAGTTCAACTTCGGTAGCTTCGACCAGGTT
GTCAACTTTGCCCAGCAGAATGGCCTCAAGGTCCGAGGTCACACTCTGGTCTGGCACTCTCAGCTCCCTCAGTGGGT
TAAGAACATCAACGACAAGGCTACTCTGACCAAGGTCATTGAGAACCACGTCACCCAAGTCGTTGGACGCTACAAGG
GCAAGATCTACGCCTGGGACGTGGTCAACGAGATCTTCGAGTGGGACGGTACCCTCCGAAAGGACTCTCACTTCAAC
AACGTCTTCGGCAACGACGACTACGTTGGCATTGCCTTCCGCGCCGCCCGCAAGGCTGACCCCAACGCCAAGCTGTA
CATCAACGACTACAGCCTCGACTCCGGCAGCGCCTCCAAGGTCACCAAGGGTATGGTTCCCTCCGTCAAGAAGTGGC
TCAGCCAGGGCGTTCCCGTCGACGGCATTGGCTCTCAGACTCACCTTGACCCCGGTGCCGCTGGCCAAATCCAGGGT
GCTCTCACTGCCCTCGCCAATTCTGGTGTCAAGGAGGTTGCCATCACCGAGCTCGACATCCGCACTGCCCCCGCCAA
CGACTACGCTACCGTCACCAAGGCCTGCCTCAACGTCCCCAAGTGCATTGGTATCACCGTCTGGGGTGTCTCTGACA
AGAACTCTTGGCGCAAGGAGCACGACAGTCTTCTGTTCGATGCTAACTACAACCCCAAGCCTGCTTACACTGCTGTT
GTCAACGCTCTCCGCTAA

Figure 6

(SEQ ID NO: 2)

Qaadsinkliknkgklyygtitdpnllgvakdtaiikadfgavtpensgkwdatepsqgkfnfgsfdqvvnfaqqnglkvrghtlvwhs
qlpqwvknindkatltkvienhvtqvvgrykgkiyawdvvneifewdgtlrkdshfnnvfgnddyvgiafraarkadpnaklyindysl
dsgsaskvtkgmvpsvkkwlsqgvpvdgigsqthldpgaagqiqgaltalansgvkevaiteldirtapandyatvtkaclnvpkci
gitvwgvsdknswrkehdsllfdanynpkpaytavvnalr

Figure 7

(SEQ ID NO:3)

ATTCCCACCGCCATCGAGCCCCGCCAGGCCTCCGACAGCATCAACAAGCTGATCAAGAACAAGGGCAAGCTCTACTA
CGGAACCATCACCGACCCCAACCTGCTCGGCGTCGCAAAGGACACTGCCATCATCAAGGCTGACTTTGGCGCCGTCA
CACCCGAGAACTCGGGTAAGTGGGATGCCACCGAGCCCAGCCAGGGCAAGTTCAACTTCGGCAGCTTCGACCAGGTC
GTCAACTTTGCTCAGCAGAATGGCCTCAAGGTCCGAGGTCACACTCTAGTCTGGCACTCCCAGCTCCCTCAGTGGGT
TAAGAACATCAACGACAAGGCTACTTTGACCAAGGTCATCGAGAACCACGTCACCAACGTCGTTGGACGCTACAAGG
GCAAGATCTACGCCTGGGACGTCGTTAACGAGATCTTCGACTGGGATGGTACCCTCCGAAAGGACTCTCACTTCAAC
AACGTCTTCGGCAACGACGACTACGTTGGCATTGCCTTCCGCGCTGCCCGCAAGGCTGACCCCAACGCCAAGCTGTA
CATCAACGACTACAGCCTCGACTCCGGCAGCGCCTCCAAGGTCACCAAGGGCATGGTTCCCTCTGTCAAGAAGTGGC
TCAGCCAGGGCGTCCCCGTCGACGGTATTGGTTCTCAGACTCACCTTGACCCCGGTGCCGCTGGCCAAATCCAGGGT
GCTCTCACTGCCCTCGCCAACTCTGGTGTGAAGGAGGTTGCCATCACCGAGCTCGACATCCGCACTGCCCCCGCCAA
CGACTACGCTACCGTTACCAAGGCCTGCCTCAACGTCCCCAAGTGCATTGGTATCACCGTCTGGGGCGTATCTGACA
AGAACTCTTGGCGCAAGGAGCACGACAGCCTTCTGTTCGATGCTAACTACAACCCCAAGGCTGCTTACACTGCTGTT

Figure 8

(SEQ ID NO: 4)

QASDSINKLIKNKGKLYYGTIHDPNLLGVAKDTAIKADFGAVTPENSGKWDATPFGQSKFSPGSFEQVVNFAQQNG
LKVRGRTLVWHSQLPQWVKSIMDKATLTKVIENHVTNVVGRYKGKIYAWDVVNEIFDWDGTLRKDSRFNRVFGNDDY
VGIAFRAARKADPNAKLYINDYSLDSSGAKKVTKGSVPSVRKWLSQGVPVDGIGSQTRLDPQAACQIQGALTALASS
GVKEVAITELDIRTAPANDYATVTKACLKVPKCIGITVWGVSDKNSWRSSRDSLLFTAKYNPKAAYTAVVRALR

Figure 9

(SEQ ID NO:5)

atgaagctgtcttcttcctctacaccgcctcgctggtcgcggccattccacccgccatcgagcccgccaggctgccgacagcatca
acaagctgatcaagaacaagggcaagctctactacggaaccatcaccgaccccaacctgctcggcgtcgcaaaggacaccgcc
atcatcaaggccgactttggcgccgttaccccgagaactcgggcaagtgggacgccaccgagcccagccagggcaagttcaa
cttcggtagcttcgaccaggttgtcaactttgcccagcagaatggcctcaaggtccgaggtcacactctggtctggcactctcagctcc
ctcagtgggttaagaacatcaacgacaaggctactctgaccaaggtcattgagaaccacgtcacccaagtcgttggacgctacaa
gggcaagatctacgcctgggtatgttttattccccagacttcttcgaaatgacttgctaacatgttcaggacgtcgtcaacgagatctt
cgagtgggacggtaccctccgaaaggactctcacttcaacaacgtcttcggcaacgacgactacgttggcattgccttccgcgccgc
ccgcaaggctgaccccaacgccaagctgtacatcaacgactacagcctcgactccggcagcgcctccaaggtcaccaagggtat
ggttccctccgtcaagaagtggctcagccagggcgttcccgtcgacggcattggctctcagactcaccttgaccccggtgccgctgg
ccaaatccagggtgctctcactgccctcgccaattctggtgtcaaggaggttgccatcaccgagctcgacatccgcactgccccgc
caacgactacgctaccgtcaccaaggcctgcctcaacgtccccaagtgcattggtatcaccgtctggggtgtctctgacaagaactct
tggcgcaaggagcacgacagtcttctgttcgatgctaactacaaccccaagcctgcttacactgctgttgtcaacgctctccgctaa

Figure 10

(SEQ ID NO:6)

atgaagctgtcttcttcctctacaccgcctcgctggtcgcggccattccacccgccatcgagcccgccaggctgccgacagcatca
acaagctgatcaagaacaagggcaagctctactacggaaccatcaccgaccccaacctgctcggcgtcgcaaaggacaccgcc
atcatcaaggccgactttggcgccgttaccccgagaactcgggcaagtgggacgccaccgagcccagccagggcaagttcaa
cttcggtagcttcgaccaggttgtcaactttgcccagcagaatggcctcaaggtccgaggtcacactctggtctggcactctcagctcc
ctcagtgggttaagaacatcaacgacaaggctactctgaccaaggtcattgagaaccacgtcacccaagtcgttggacgctacaa
gggcaagatctacgcctgggacgtcgtcaacgagatcttcgagtgggacggtaccctccgaaaggactctcacttcaacaacgtctt
cggcaacgacgactacgttggcattgccttccgcgccgcccgcaaggctgaccccaacgccaagctgtacatcaacgactacag
cctcgactccggcagcgcctccaaggtcaccaagggtatggttccctccgtcaagaagtggctcagccagggcgttcccgtcgacg
gcattggctctcagactcaccttgaccccggtgccgctggccaaatccagggtgctctcactgccctcgccaattctggtgtcaagga ggttgccatcaccgagctcgacatcgcactgcccccgccaacgactacgctaccgtcaccaaggcctgcctcaacgtccccaag
tgcattggtatcaccgtctggggtgtctctgacaagaactcttggcgcaaggagcacgacagtcttcttgttcgatgctaactacaaccc
caagcctgcttacactgctgttgtcaacgctctccgctaa

Figure 11

(SEQ ID NO: 7)

mklssflytasivaaiptaieprqaadsinklilknkgklyygtitdpnllgvakdtaiikadfgavtpensgkwdatepsqgkfnfgsfdqvvnfaq
qnglkvrghtlvwhsqlpqwvknindkatltkvienhvtqvvgrykgkiyawdvvneifewdgtlrkdshfnnvfgnddyvgiafraarkadp
naklyindysldsgsaskvtkgmvpsvkkwlsqgvpvdgigsqthldpgaagqiqgaltalansgvkevaiteldirtapandyatvtkaclnvp
kcigitvwgvsdknswrkehdsllfdanynpkpaytavvnalr

Figure 12

(SEQ ID NO: 8)

mklssflytasivaa*IPTAIEPR*QAADSINKLIKNKGKLYYGTITDPNLLGVAKDTAIIKADFGAVTPENS
GKWDATEPSQGKFNFGSFDQVVNFAQQNGLKVRGHTLVWHSQLPQWVKNINDKATLTKVIE
NHVTQVVGRYKGKIYAWDVVNEIFEWDGTLRKDSHFNNVFGNDDYVGIAFRAARKADPNAKL
YINDYSLDSGSASKVTKGMVPSVKKWLSQGVPVDGIGSQTHLDPGAAGQIQGALTALANSGV
KEVAITELDIRTAPANDYATVTKACLNVPKCIGITVWGVSDKNSWRKEHDSLLFDANYNPKPAY
TAVVNALR

Figure 13

(SEQ ID NO: 9)

*IPTAIEPR*QAADSINKLIKNKGKLYYGTITDPNLLGVAKDTAIIKADFGAVTPENSGKWDATEPS
QGKFNFGSFDQVVNFAQQNGLKVRGHTLVWHSQLPQWVKNINDKATLTKVIENHVTQVVGR
YKGKIYAWDVVNEIFEWDGTLRKDSHFNNVFGNDDYVGIAFRAARKADPNAKLYINDYSLDSG
SASKVTKGMVPSVKKWLSQGVPVDGIGSQTHLDPGAAGQIQGALTALANSGVKEVAITELDIR
TAPANDYATVTKACLNVPKCIGITVWGVSDKNSWRKEHDSLLFDANYNPKPAYTAVVNALR

Figure 14

(SEQ ID NO: 10)

ATGAAGCTGTCTTCTTTCCTCTACACCGCCTCGCTGGTCGCGGCCATTCCCACCGCCATC
GAGCCCCGCCAGGCTGCCGACAGCATCAACAAGCTGATCAAGAACAAGGGCAAGCTCTA
CTACGGAACCATCACCGACCCCAACCTGCTCGGCGTCGCAAAGGACACCGCCATCATCA
AGGCCGACTTTGGCGCCGTTACCCCCGAGAACTCGGGCAAGTGGGACGCCACCGAGCC
CAGCCAGGGCAAGTTCAACTTCGGTAGCTTCGACCAGGTTGTCAACTTTGCCCAGCAGAA
TGGCCTCAAGGTCCGAGGTCACACTCTGGTCTGGCACTCTCAGCTCCCTCAGTGGGTTAA
GAACATCAACGACAAGGCTACTCTGACCAAGGTCATTGAGAACCACGTCACCCAAGTCGT
TGGACGCTACAAGGGCAAGATCTACGCCTGG*gtatgttttattccccagacttcttcgaaatgactttgcta*
*acatgttcag*GACGTCGTCAACGAGATCTTCGAGTGGGACGGTACCCTCCGAAAGGACTCTC
ACTTCAACAACGTCTTCGGCAACGACGACTACGTTGGCATTGCCTTCCGCGCCGCCCGC
AAGGCTGACCCCAACGCCAAGCTGTACATCAACGACTACAGCCTCGACTCCGGCAGCGC
CTCCAAGGTCACCAAGGGTATGGTTCCCTCCGTCAAGAAGTGGCTCAGCCAGGGCGTTC
CCGTCGACGGCATTGGCTCTCAGACTCACCTTGACCCCGGTGCCGCTGGCCAAATCCAG
GGTGCTCTCACTGCCCTCGCCAATTCTGGTGTCAAGGAGGTTGCCATCACCGAGCTCGA
CATCCGCACTGCCCCCGCCAACGACTACGCTACCGTCACCAAGGCCTGCCTCAACGTCC
CCAAGTGCATTGGTATCACCGTCTGGGGTGTCTCTGACAAGAACTCTTGGCGCAAGGAG
CACGACAGTCTTCTGTTCGATGCTAACTACAACCCCAAGCCTGCTTACACTGCTGTTGTCA
ACGCTCTCCGCTAA

Figure 15

(SEQ ID NO: 11)

ATGAAGCTGTCTTCTTTCCTCTACACCGCCTCGCTGGTCGCGGCCATTCCCACCGCCATC
GAGCCCCGCCAGGCTGCCGACAGCATCAACAAGCTGATCAAGAACAAGGGCAAGCTCTA
CTACGGAACCATCACCGACCCCAACCTGCTCGGCGTCGCAAAGGACACCGCCATCATCA
AGGCCGACTTTGGCGCCGTTACCCCCGAGAACTCGGGCAAGTGGGACGCCACCGAGCC
CAGCCAGGGCAAGTTCAACTTCGGTAGCTTCGACCAGGTTGTCAACTTTGCCCAGCAGAA
TGGCCTCAAGGTCCGAGGTCACACTCTGGTCTGGCACTCTCAGCTCCCTCAGTGGGTTAA
GAACATCAACGACAAGGCTACTCTGACCAAGGTCATTGAGAACCACGTCACCCAAGTCGT
TGGACGCTACAAGGGCAAGATCTACGCCTGGGACGTCGTCAACGAGATCTTCGAGTGGG
ACGGTACCCTCCGAAAGGACTCTCACTTCAACAACGTCTTCGGCAACGACGACTACGTTG
GCATTGCCTTCCGCGCCGCCCGCAAGGCTGACCCCAACGCCAAGCTGTACATCAACGAC
TACAGCCTCGACTCCGGCAGCGCCTCCAAGGTCACCAAGGGTATGGTTCCCTCCGTCAA
GAAGTGGCTCAGCCAGGGCGTTCCCGTCGACGGCATTGGCTCTCAGACTCACCTTGACC
CCGGTGCCGCTGGCCAAATCCAGGGTGCTCTCACTGCCCTCGCCAATTCTGGTGTCAAG
GAGGTTGCCATCACCGAGCTCGACATCCGCACTGCCCCCGCCAACGACTACGCTACCGT
CACCAAGGCCTGCCTCAACGTCCCCAAGTGCATTGGTATCACCGTCTGGGGTGTCTCTGA
CAAGAACTCTTGGCGCAAGGAGCACGACAGTCTTCTGTTCGATGCTAACTACAACCCCAA
GCCTGCTTACACTGCTGTTGTCAACGCTCTCCGCTAA

Figure 16

(SEQ ID NO: 12)

mklssflylaslvaa*IPTAIEPR*QASDSINKLIKNKGKLYYGTITDPNLLGVAKDTAIIKADFGAVTPENS
GKWDATEPSQGKFNFGSFDQVVNFAQQNGLKVRGHTLVWHSQLPQWVKNINDKATLTKVIE
NHVTNVVGRYKGKIYAWDVVNEIFDWDGTLRKDSHFNNVFGNDDYVGIAFRAARKADPNAKL
YINDYSLDSGSASKVTKGMVPSVKKWLSQGVPVDGIGSQTHLDPGAAGQIQGALTALANSGV
KEVAITELDIRTAPANDYATVTKACLNVPKCIGITVWGVSDKNSWRKEHDSLLFDANYNPKAAY
TAVVNALR

Figure 17

(SEQ ID NO: 13)

*IPTAIEPR*QASDSINKLIKNKGKLYYGTITDPNLLGVAKDTAIIKADFGAVTPENSGKWDATEPS
QGKFNFGSFDQVVNFAQQNGLKVRGHTLVWHSQLPQWVKNINDKATLTKVIENHVTNVVGR
YKGKIYAWDVVNEIFDWDGTLRKDSHFNNVFGNDDYVGIAFRAARKADPNAKLYINDYSLDSG
SASKVTKGMVPSVKKWLSQGVPVDGIGSQTHLDPGAAGQIQGALTALANSGVKEVAITELDIR
TAPANDYATVTKACLNVPKCIGITVWGVSDKNSWRKEHDSLLFDANYNPKAAYTAVVNALR

Figure 18

(SEQ ID NO:14)

ATGAAGCTGTCTTCGTTCCTCTACACCGCCTCGCTGGTCGCGGCCATTCCCACCGCCAT
CGAGCCCCGCCAGGCCTCCGACAGCATCAACAAGCTGATCAAGAACAAGGGCAAGCTCT
ACTACGGAACCATCACCGACCCCAACCTGCTCGGCGTCGCAAAGGACACTGCCATCATC
AAGGCTGACTTTGGCGCCGTCACACCGAGAACTCGGGTAAGTGGGATGCCACCGAGCC
CAGCCAGGGCAAGTTCAACTTCGGCAGCTTCGACCAGGTCGTCAACTTTGCTCAGCAGAA
TGGCCTCAAGGTCCGAGGTCACACTCTAGTCTGGCACTCCCAGCTCCCTCAGTGGGTTAA
GAACATCAACGACAAGGCTACTTTGACCAAGGTCATCGAGAACCACGTCACCAACGTCGT
TGGACGCTACAAGGGCAAGATCTACGCCTGG*gtatgttttcttcactcgaacttcttataaatggctttactaacatg*
*ttcag*GACGTCGTTAACGAGATCTTCGACTGGGATGGTACCCTCCGAAAGGACTCTCACTTC
AACAACGTCTTCGGCAACGACGACTACGTTGGCATTGCCTTCCGCGCTGCCCGCAAGGC
TGACCCCAACGCCAAGCTGTACATCAACGACTACAGCCTCGACTCCGGCAGCGCCTCCA
AGGTCACCAAGGGCATGGTTCCCTCTGTCAAGAAGTGGCTCAGCCAGGGCGTCCCCGTC
GACGGTATTGGTTCTCAGACTCACCTTGACCCCGGTGCCGCTGGCCAAATCCAGGGTGC
TCTCACTGCCCTCGCCAACTCTGGTGTGAAGGAGGTTGCCATCACCGAGCTCGACATCC
GCACTGCCCCGCCAACGACTACGCTACCGTTACCAAGGCCTGCCTCAACGTCCCCAAG
TGCATTGGTATCACCGTCTGGGGCGTATCTGACAAGAACTCTTGGCGCAAGGAGCACGA
CAGCCTTCTGTTCGATGCTAACTACAACCCCAAGGCTGCTTACACTGCTGTTGTCAACGC
TCTCCGCTAA

Figure 19

(SEQ ID NO: 15)

ATGAAGCTGTCTTCCTTCCTCTACACCGCCTCGCTGGTCGCGGCCATTCCCACCGCCAT
CGAGCCCCGCCAGGCCTCCGACAGCATCAACAAGCTGATCAAGAACAAGGGCAAGCTCT
ACTACGGAACCATCACCGACCCCAACCTGCTCGGCGTCGCAAAGGACACTGCCATCATC
AAGGCTGACTTTGGCGCCGTCACACCCGAGAACTCGGGTAAGTGGGATGCCACCGAGCC
CAGCCAGGGCAAGTTCAACTTCGGCAGCTTCGACCAGGTCGTCAACTTTGCTCAGCAGAA
TGGCCTCAAGGTCCGAGGTCACACTCTAGTCTGGCACTCCCAGCTCCCTCAGTGGGTTAA
GAACATCAACGACAAGGCTACTTTGACCAAGGTCATCGAGAACCACGTCACCAACGTCGT
TGGACGCTACAAGGGCAAGATCTACGCCTGGGACGTCGTTAACGAGATCTTCGACTGGG
ATGGTACCCTCCGAAAGGACTCTCACTTCAACAACGTCTTCGGCAACGACGACTACGTTG
GCATTGCCTTCCGCGCTGCCCGCAAGGCTGACCCCAACGCCAAGCTGTACATCAACGAC
TACAGCCTCGACTCCGGCAGCGCCTCCAAGGTCACCAAGGGCATGGTTCCCTCTGTCAA
GAAGTGGCTCAGCCAGGGCGTCCCCGTCGACGGTATTGGTTCTCAGACTCACCTTGACC
CCGGTGCCGCTGGCCAAATCCAGGGTGCTCTCACTGCCCTCGCCAACTCTGGTGTGAAG
GAGGTTGCCATCACCGAGCTCGACATCCGCACTGCCCCCGCCAACGACTACGCTACCGT
TACCAAGGCCTGCCTCAACGTCCCCAAGTGCATTGGTATCACCGTCTGGGGCGTATCTGA
CAAGAACTCTTGGCGCAAGGAGCACGACAGCCTTCTGTTCGATGCTAACTACAACCCCAA
GGCTGCTTACACTGCTGTTGTCAACGCTCTCCGCTAA

Figure 20

(SEQ ID NO: 16)

QAADSINKLIKMKGKLYYGTITDPNLLGVAKDTAVIKADPGAVTPENSGKWDATEPSQGRFNFGSPDQVVNFAQGNG
LKVRGHTLVWHSQLPQWVKNINDKAILTRVIENHVTQVVGRYKGKIYAWDVVNEIFDWDGTLRDSPFNHVFGNDDY
VGIAFRAARKADPRAKLYINDYSLDSASASKYTKGMVPSVKKWLSQGVPVDGIGSQGHLDPGAAGQVQSALTALANS
GVKEVAITELDIRTAFANDYATVTKACLRVPKCIGITVWGVSDKNSWRKEHDSLLFDSNYNPKPAYTAVVNALR

Figure 21

(SEQ ID NO: 17)

ATGAAGCTGTCTTCTTTCCTCTACACCGCCTCGCTGGTCGCGGCCATTCCCACCGCCATC
GAGCCCCGCCAGGCCGCCGACAGCATCAACAAGCTGATCAAGAACAAGGGCAAGCTCTA
CTACGGAACCATCACCGACCCCAACCTGCTCGGCGTCGCAAAGGACACCGCCGTCATCA
AGGCCGACTTTGGCGCCGTCACCCCCGAGAACTCGGGCAAGTGGGACGCCACCGAGCC
CAGCCAGGGCAACTTCAACTTCGGTAGCTTCGACCAGGTCGTCAACTTTGCTCAGCAGAA
TGGCCTCAAGGTCCGAGGTCACACTCTGGTCTGGCACTCTCAGCTCCCTCAGTGGGTTAA
GAACATCAACGACAAGGCTACTCTGACCAAGGTCATTGAGAACCACGTCACCCAAGTCGT
TGGACGCTACAAGGGCAAGATCTACGCCTGGgtatgttttcttgcctcgaccttctcaaagatgaatttgcta
acatgttcagGACGTTGTCAACGAGATCTTCGACTGGGACGGTACCCTCCGAAAGGATTCTCA
CTTCAACAACGTCTTCGGCAACGATGACTACGTTGGCATTGCCTTCCGCGCCGCCCGCAA
GGCTGACCCCAACGCCAAGCTGTACATCAACGACTACAGCCTCGACTCCGCCAGCGCCT
CCAAGGTCACCAAGGGCATGGTCCCCTCCGTCAAGAAGTGGCTCAGCCAGGGCGTTCCC
GTCGACGGCATTGGCTCCCAGTCTCACCTTGACCCCGGTGCCGCTGGCCAAGTCCAGGG
TGCTCTCACTGCCCTCGCCAACTCTGGTGTCAAGGAGGTTGCCATCACCGAGCTCGACAT
CCGCACTGCCCCCGCCAACGACTACGCCACCGTCACCAAGGCCTGCCTAAACGTCCCCA
AGTGCATTGGTATCACCGTCTGGGGTGTCTCTGACAAGAACTCTTGGCGCAAGGAGCAC
GACAGCCTTCTGTTCGACTCCAACTACAACCCCAAGCCTGCTTACACTGCTGTTGTCAAC
GCTCTCCGCTAA

Figure 22

(SEQ ID NO. 18)

ATGAAGCTGTCTTCTTTCCTCTACACCGCCTCGCTGGTCGCGGCCATTCCCACCGCCATC
GAGCCCCGCCAGGCCGCCGACAGCATCAACAAGCTGATCAAGAACAAGGGCAAGCTCTA
CTACGGAACCATCACCGACCCCAACCTGCTCGGCGTCGCAAAGGACACCGCCGTCATCA
AGGCCGACTTTGGCGCCGTCACCCCCGAGAACTCGGGCAAGTGGGACGCCACCGAGCC
CAGCCAGGGCAACTTCAACTTCGGTAGCTTCGACCAGGTCGTCAACTTTGCTCAGCAGAA
TGGCCTCAAGGTCCGAGGTCACACTCTGGTCTGGCACTCTCAGCTCCCTCAGTGGGTTAA
GAACATCAACGACAAGGCTACTCTGACCAAGGTCATTGAGAACCACGTCACCCAAGTCGT
TGGACGCTACAAGGGCAAGATCTACGCCTGGGACGTTGTCAACGAGATCTTCGACTGGG
ACGGTACCCTCCGAAAGGATTCTCACTTCAACAACGTCTTCGGCAACGATGACTACGTTG
GCATTGCCTTCCGCGCCGCCCGCAAGGCTGACCCCAACGCCAAGCTGTACATCAACGAC
TACAGCCTCGACTCCGCCAGCGCCTCCAAGGTCACCAAGGGCATGGTCCCCTCCGTCAA
GAAGTGGCTCAGCCAGGGCGTTCCCGTCGACGGCATTGGCTCCAGTCTCACCTTGACC
CCGGTGCCGCTGGCCAAGTCCAGGGTGCTCTCACTGCCCTCGCCAACTCTGGTGTCAAG
GAGGTTGCCATCACCGAGCTCGACATCCGCACTGCCCCCGCCAACGACTACGCCACCGT
CACCAAGGCCTGCCTAAACGTCCCCAAGTGCATTGGTATCACCGTCTGGGGTGTCTCTGA
CAAGAACTCTTGGCGCAAGGAGCACGACAGCCTTCTGTTCGACTCCAACTACAACCCCAA
GCCTGCTTACACTGCTGTTGTCAACGCTCTCCGCTAA

Figure 23

(SEQ ID NO. 19)

ATTCCACGGCATCGAGCCCCGCCAGGCCGCCGACAGCATCAACAAGCTGATCAAGAACAAGGGCAAGCTCTACTA
CGGAATCATCACCGACCCCAACCTGCTCGGCGTCGCAAAGGACACCGCCGTCATCAAGCCCGACTTTGGCGCCGTCA
CCCCCGAGAACTCGGGCAAGTGGGACGGCACCGAGCCCAGCCAGGGCAACTTCGAACTCGGTAGCTTCGACCAGGTG
GTCAACTTTGCTCAGCAGAATGGCCTCAAGGTCCGAGGTCACACTCTGGTCTGGCACTCTCAGTTCCCTCAGTGGGT
TAAGAACATCAACGACAAGGCTACTCTGACCAAGGTCATTGAGAACCACGTCACCCAAGTGTTGGACGCTACAAGG
GCAAGATACGCCTGGGACGTTGTCAACGAGATCTTCGACTGGGACGGTACCCTCCGAAAGGATTCTCACTTCAAC
AACGTCTTCGGCAACGATGACTACGTTGGCATTGCTTTCCGCGCCGCCCGCAAGGCTGACCCCAACGCCAAGCTGTA
CATCAACGACTACAGCCTGGACTCCGGCAGCGCCCTCCAAGGTCACCAAGGCCATGGTCGCCCTCCGTCAAGAAGTGGC
TCAGCCAGGGCGTTCCCGTCGACTGGCATTGGTCGAGTCTCACCTTGACCCCGGTGCCGCTGGCCAAGTCCAGGGT
GCTGTCACTGCCTTCGCCAACGTCTGGTGTCAAGGAGGTTGCCATCACCGACCTCGACATCCGACTGCCCGGCCAA
CGACTAGCCGACTGTCAGCAAGGGCTGCTTAAACGTCCCCAACGCCATTGGTATCACCGTCGGGGTGTTCCTGACA
AGAACTCTTGGCGCAAGGAGCACGACAGCTTCTGTTCGACTCCAACTACAACCCCAAGCTGCTTACACTGCTGTT
GTCAACCGTCTCCCTAA

```
                              SEQUENCE LISTING

<160> NUMBER OF SEQ ID NOS: 55

<210> SEQ ID NO 1
<211> LENGTH: 942
<212> TYPE: DNA
<213> ORGANISM: Fusarium verticillioides

<400> SEQUENCE: 1
attcccaccg ccatcgagcc ccgccaggct gccgacagca tcaacaagct gatcaagaac      60
aagggcaagc tctactacgg aaccatcacc gacccccaacc tgctcggcgt cgcaaaggac    120
accgccatca tcaaggccga ctttggcgcc gttaccccccg agaactcggg caagtgggac    180
gccaccgagc ccagccaggg caagttcaac ttcggtagct tcgaccaggt tgtcaacttt    240
gcccagcaga atggcctcaa ggtccgaggt cacactctgg tctggcactc tcagctccct    300
cagtgggtta agaacatcaa cgacaaggct actctgacca aggtcattga gaaccacgtc    360
acccaagtcg ttggacgcta caagggcaag atctacgcct gggacgtcgt caacgagatc    420
ttcgagtggg acggtaccct ccgaaaggac tctcacttca caacgtcttt cggcaacgac    480
gactacgttg gcattgcctt ccgcgccgcc cgcaaggctg accccaacgc caagctgtac    540
atcaacgact acagcctcga ctccggcagc gcctccaagg tcaccaaggg tatggttccc    600
tccgtcaaga agtggctcag ccagggcgtt cccgtcgacg gcattggctc tcagactcac    660
cttgaccccg gtgccgctgg ccaaatccag ggtgctctca ctgccctcgc caattctggt    720
gtcaaggagg ttgccatcac cgagctcgac atccgcactg ccccgccaa cgactacgct    780 accgtcacca aggcctgcct caacgtcccc aagtgcattg gtatcaccgt ctggggtgtc    840
tctgacaaga actcttggcg caaggagcac gacagtcttc tgttcgatgc taactacaac    900
cccaagcctg cttacactgc tgttgtcaac gctctccgct aa                       942
```

<210> SEQ ID NO 2
<211> LENGTH: 305
<212> TYPE: PRT
<213> ORGANISM: Fusarium verticillioides

<400> SEQUENCE: 2

Gln Ala Ala Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Thr Ala Ile Ile Lys Ala Asp Phe Gly Ala Val Thr Pro Glu Asn Ser
        35                  40                  45

Gly Lys Trp Asp Ala Thr Glu Pro Ser Gln Gly Lys Phe Asn Phe Gly
50                  55                  60

Ser Phe Asp Gln Val Val Asn Phe Ala Gln Gln Asn Gly Leu Lys Val
65                  70                  75                  80

Arg Gly His Thr Leu Val Trp His Ser Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
130                 135                 140

Phe Asn Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Ala Ala Gly Gln Ile Gln Gly Ala
210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Thr Ala Val Val Asn Ala Leu
290                 295                 300

Arg
305

<210> SEQ ID NO 3
<211> LENGTH: 942
<212> TYPE: DNA
<213> ORGANISM: Fusarium oxysporum

<400> SEQUENCE: 3
attcccaccg ccatcgagcc ccgccaggcc tccgacagca tcaacaagct gatcaagaac      60

```
aagggcaagc tctactacgg aaccatcacc gaccccaacc tgctcggcgt cgcaaaggac    120
actgccatca tcaaggctga ctttggcgcc gtcacacccg agaactcggg taagtgggat    180
gccaccgagc ccagccaggg caagttcaac ttcggcagct cgaccaggt cgtcaacttt    240 gctcagcaga atggcctcaa ggtccgaggt cacactctag tctggcactc ccagctccct    300
cagtgggtta agaacatcaa cgacaaggct actttgacca aggtcatcga gaaccacgtc    360
accaacgtcg ttggacgcta caagggcaag atctacgcct gggacgtcgt taacgagatc    420
ttcgactggg atggtaccct ccgaaaggac tctcacttca acaacgtctt cggcaacgac    480
gactacgttg gcattgcctt ccgcgctgcc cgcaaggctg accccaacgc caagctgtac    540
atcaacgact acagcctcga ctccggcagc gcctccaagg tcaccaaggg catggttccc    600
tctgtcaaga gtggctcag ccagggcgtc cccgtcgacg gtattggttc tcagactcac    660
cttgaccccg gtgccgctgg ccaaatccag ggtgctctca ctgccctcgc caactctggt    720
gtgaaggagg ttgccatcac cgagctcgac atccgcactg ccccgccaa cgactacgct    780 accgttacca aggcctgcct caacgtcccc aagtgcattg gtatcaccgt ctggggcgta    840
tctgacaaga actcttggcg caaggagcac gacagcctc tgttcgatgc taactacaac    900
cccaaggctg cttacactgc tgttgtcaac gctctccgct aa                       942
```

```
<210> SEQ ID NO 4
<211> LENGTH: 305
<212> TYPE: PRT
<213> ORGANISM: Fusarium oxysporum

<400> SEQUENCE: 4

Gln Ala Ser Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Thr Ala Ile Ile Lys Ala Asp Phe Gly Ala Val Thr Pro Glu Asn Ser
        35                  40                  45

Gly Lys Trp Asp Ala Thr Glu Pro Ser Gln Gly Lys Phe Asn Phe Gly
    50                  55                  60

Ser Phe Asp Gln Val Val Asn Phe Ala Gln Gln Asn Gly Leu Lys Val
65                  70                  75                  80

Arg Gly His Thr Leu Val Trp His Ser Gln Leu Pro Gln Trp Val Lys
                85                  90                  95

Asn Ile Asn Asp Lys Ala Thr Leu Thr Lys Val Ile Glu Asn His Val
            100                 105                 110

Thr Asn Val Val Gly Arg Tyr Lys Gly Lys Ile Tyr Ala Trp Asp Val
        115                 120                 125

Val Asn Glu Ile Phe Asp Trp Asp Gly Thr Leu Arg Lys Asp Ser His
    130                 135                 140

Phe Asn Asn Val Phe Gly Asn Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Ala Ala Gly Gln Ile Gln Gly Ala
    210                 215                 220
```

```
Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
            245                 250                 255

Ala Cys Leu Asn Val Pro Lys Cys Ile Gly Ile Thr Val Trp Gly Val
        260                 265                 270

Ser Asp Lys Asn Ser Trp Arg Lys Glu His Asp Ser Leu Leu Phe Asp
        275                 280                 285

Ala Asn Tyr Asn Pro Lys Ala Ala Tyr Thr Ala Val Val Asn Ala Leu
        290                 295                 300

Arg
305

<210> SEQ ID NO 5
<211> LENGTH: 1039
<212> TYPE: DNA
<213> ORGANISM: Fusarium verticillioides

<400> SEQUENCE: 5
atgaagctgt cttctttcct ctacaccgcc tcgctggtcg cggccattcc caccgccatc    60
gagccccgcc aggctgccga cagcatcaac aagctgatca gaacaaggg caagctctac   120 tacggaacca tcaccgaccc caacctgctc ggcgtcgcaa aggacaccgc catcatcaag   180
gccgactttg gcgccgttac ccccgagaac tcgggcaagt gggacgccac cgagcccagc   240
cagggcaagt tcaacttcgg tagcttcgac caggttgtca actttgccca gcagaatggc   300
ctcaaggtcc gaggtcacac tctggtctgg cactctcagc tccctcagtg ggttaagaac   360
atcaacgaca aggctactct gaccaaggtc attgagaacc acgtcaccca agtcgttgga   420
cgctacaagg gcaagatcta cgcctgggta tgttttattc ccccagactt cttcgaaatg   480
actttgctaa catgttcagg acgtcgtcaa cgagatcttc gagtgggacg gtaccctccg   540
aaaggactct cacttcaaca acgtcttcgg caacgacgac tacgttggca ttgccttccg   600
cgccgcccgc aaggctgacc ccaacgccaa gctgtacatc aacgactaca gcctcgactc   660
cggcagcgcc tccaaggtca ccaagggtat ggttccctcc gtcaagaagt ggctcagcca   720
gggcgttccc gtcgacggca ttggctctca gactcacctt gaccccggtg ccgctggcca   780
aatccagggt gctctcactg ccctcgccaa ttctggtgtc aaggaggttg ccatcaccga   840
gctcgacatc cgcactgccc ccgccaacga ctacgctacc gtcaccaagg cctgcctcaa   900
cgtccccaag tgcattggta tcaccgtctg gggtgtctct gacaagaact cttggcgcaa   960
ggagcacgac agtcttctgt tcgatgctaa ctacaacccc aagcctgctt acactgctgt  1020
tgtcaacgct ctccgctaa                                                1039

<210> SEQ ID NO 6
<211> LENGTH: 987
<212> TYPE: DNA
<213> ORGANISM: Fusarium verticillioides

<400> SEQUENCE: 6
atgaagctgt cttctttcct ctacaccgcc tcgctggtcg cggccattcc caccgccatc    60
gagccccgcc aggctgccga cagcatcaac aagctgatca gaacaaggg caagctctac   120 tacggaacca tcaccgaccc caacctgctc ggcgtcgcaa aggacaccgc catcatcaag   180
gccgactttg gcgccgttac ccccgagaac tcgggcaagt gggacgccac cgagcccagc   240
```

```
cagggcaagt caacttcgg tagcttcgac caggttgtca actttgccca gcagaatggc    300
ctcaaggtcc gaggtcacac tctggtctgg cactctcagc tccctcagtg ggttaagaac    360
atcaacgaca aggctactct gaccaaggtc attgagaacc acgtcaccca gtcgttgga     420 cgctacaagg gcaagatcta cgcctgggac gtcgtcaacg agatcttcga gtgggacggt    480
accctccgaa aggactctca cttcaacaac gtcttcggca cgacgacta cgttggcatt     540 gccttccgcg ccgcccgcaa ggctgacccc aacgccaagc tgtacatcaa cgactacagc    600
ctcgactccg gcagcgcctc caaggtcacc aagggtatgg ttccctccgt caagaagtgg    660
ctcagccagg gcgttcccgt cgacggcatt ggctctcaga ctcaccttga ccccggtgcc    720
gctggccaaa tccagggtgc tctcactgcc ctcgccaatt ctggtgtcaa ggaggttgcc    780
atcaccgagc tcgacatccg cactgccccc gccaacgact acgctaccgt caccaaggcc    840
tgcctcaacg tccccaagtg cattggtatc accgtctggg gtgtctctga caagaactct    900
tggcgcaagg agcacgacag tcttctgttc gatgctaact acaaccccaa gcctgcttac    960
actgctgttg tcaacgctct ccgctaa                                        987
```

<210> SEQ ID NO 7
<211> LENGTH: 328
<212> TYPE: PRT
<213> ORGANISM: Fusarium verticillioides

<400> SEQUENCE: 7

Met Lys Leu Ser Ser Phe Leu Tyr Thr Ala Ser Leu Val Ala Ala Ile
1               5                   10                  15

Pro Thr Ala Ile Glu Pro Arg Gln Ala Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Gln Val Val Gly Arg Tyr Lys Gly
    130                 135                 140

Lys Ile Tyr Ala Trp Asp Val Val Asn Glu Ile Phe Glu Trp Asp Gly
145                 150                 155                 160

Thr Leu Arg Lys Asp Ser His Phe Asn Asn Val Phe Gly Asn Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220

Val Pro Val Asp Gly Ile Gly Ser Gln Thr His Leu Asp Pro Gly Ala
225                 230                 235                 240

```
Ala Gly Gln Ile Gln Gly Ala Leu Thr Ala Leu Ala Asn Ser Gly Val
                245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
        275                 280                 285

Gly Ile Thr Val Trp Gly Val Ser Asp Lys Asn Ser Trp Arg Lys Glu
    290                 295                 300

His Asp Ser Leu Leu Phe Asp Ala Asn Tyr Asn Pro Lys Pro Ala Tyr
305                 310                 315                 320

Thr Ala Val Val Asn Ala Leu Arg
                325

<210> SEQ ID NO 8
<211> LENGTH: 328
<212> TYPE: PRT
<213> ORGANISM: Fusarium verticillioides

<400> SEQUENCE: 8

Met Lys Leu Ser Ser Phe Leu Tyr Thr Ala Ser Leu Val Ala Ala Ile
1               5                   10                  15

Pro Thr Ala Ile Glu Pro Arg Gln Ala Ala Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Gln Val Val Gly Arg Tyr Lys Gly
    130                 135                 140

Lys Ile Tyr Ala Trp Asp Val Val Asn Glu Ile Phe Glu Trp Asp Gly
145                 150                 155                 160

Thr Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
                245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
        275                 280                 285
```

```
Gly Ile Thr Val Trp Gly Val Ser Asp Lys Asn Ser Trp Arg Lys Glu
    290                 295                 300

His Asp Ser Leu Leu Phe Asp Ala Asn Tyr Asn Pro Lys Pro Ala Tyr
305                 310                 315                 320

Thr Ala Val Val Asn Ala Leu Arg
                325

<210> SEQ ID NO 9
<211> LENGTH: 313
<212> TYPE: PRT
<213> ORGANISM: Fusarium verticillioides

<400> SEQUENCE: 9

Ile Pro Thr Ala Ile Glu Pro Arg Gln Ala Ala Asp Ser Ile Asn Lys
1               5                   10                  15

Leu Ile Lys Asn Lys Gly Lys Leu Tyr Tyr Gly Thr Ile Thr Asp Pro
            20                  25                  30

Asn Leu Leu Gly Val Ala Lys Asp Thr Ala Ile Ile Lys Ala Asp Phe
        35                  40                  45

Gly Ala Val Thr Pro Glu Asn Ser Gly Lys Trp Asp Ala Thr Glu Pro
50                  55                  60

Ser Gln Gly Lys Phe Asn Phe Gly Ser Phe Asp Gln Val Val Asn Phe
65                  70                  75                  80

Ala Gln Gln Asn Gly Leu Lys Val Arg Gly His Thr Leu Val Trp His
                85                  90                  95

Ser Gln Leu Pro Gln Trp Val Lys Asn Ile Asn Asp Lys Ala Thr Leu
            100                 105                 110

Thr Lys Val Ile Glu Asn His Val Thr Gln Val Val Gly Arg Tyr Lys
        115                 120                 125

Gly Lys Ile Tyr Ala Trp Asp Val Val Asn Glu Ile Phe Glu Trp Asp
130                 135                 140

Gly Thr Leu Arg Lys Asp Ser His Phe Asn Asn Val Phe Gly Asn Asp
145                 150                 155                 160

Asp Tyr Val Gly Ile Ala Phe Arg Ala Ala Arg Lys Ala Asp Pro Asn
                165                 170                 175

Ala Lys Leu Tyr Ile Asn Asp Tyr Ser Leu Asp Ser Gly Ser Ala Ser
            180                 185                 190

Lys Val Thr Lys Gly Met Val Pro Ser Val Lys Lys Trp Leu Ser Gln
        195                 200                 205

Gly Val Pro Val Asp Gly Ile Gly Ser Gln Thr His Leu Asp Pro Gly
210                 215                 220

Ala Ala Gly Gln Ile Gln Gly Ala Leu Thr Ala Leu Ala Asn Ser Gly
225                 230                 235                 240

Val Lys Glu Val Ala Ile Thr Glu Leu Asp Ile Arg Thr Ala Pro Ala
                245                 250                 255

Asn Asp Tyr Ala Thr Val Thr Lys Ala Cys Leu Asn Val Pro Lys Cys
            260                 265                 270

Ile Gly Ile Thr Val Trp Gly Val Ser Asp Lys Asn Ser Trp Arg Lys
        275                 280                 285

Glu His Asp Ser Leu Leu Phe Asp Ala Asn Tyr Asn Pro Lys Pro Ala
290                 295                 300

Tyr Thr Ala Val Val Asn Ala Leu Arg
305                 310
```

```
<210> SEQ ID NO 10
<211> LENGTH: 1039
<212> TYPE: DNA
<213> ORGANISM: Fusarium verticillioides
<400> SEQUENCE: 10
atgaagctgt cttctttcct ctacaccgcc tcgctggtcg cggccattcc caccgccatc 60
gagccccgcc aggctgccga cagcatcaac aagctgatca agaacaaggg caagctctac 120
tacggaacca tcaccgaccc caacctgctc ggcgtcgcaa aggacaccgc catcatcaag 180
gccgactttg gcgccgttac ccccgagaac tcgggcaagt gggacgccac cgagcccagc 240
cagggcaagt tcaacttcgg tagcttcgac caggttgtca actttgccca gcagaatggc 300
ctcaaggtcc gaggtcacac tctggtctgg cactctcagc tccctcagtg ggttaagaac 360
atcaacgaca aggctactct gaccaaggtc attgagaacc acgtcaccca agtcgttgga 420
cgctacaagg gcaagatcta cgcctgggta tgttttattc ccccagactt cttcgaaatg 480
actttgctaa catgttcagg acgtcgtcaa cgagatcttc gagtgggacg gtaccctccg 540
aaaggactct cacttcaaca acgtcttcgg caacgacgac tacgttggca ttgccttccg 600
cgccgcccgc aaggctgacc ccaacgccaa gctgtacatc aacgactaca gcctcgactc 660
cggcagcgcc tccaaggtca ccaagggtat ggttccctcc gtcaagaagt ggctcagcca 720
gggcgttccc gtcgacggca ttggctctca gactcacctt gaccccggtg ccgctggcca 780
aatccagggt gctctcactg ccctcgccaa ttctggtgtc aaggaggttg ccatcaccga 840
gctcgacatc cgcactgccc ccgccaacga ctacgctacc gtcaccaagg cctgcctcaa 900
cgtccccaag tgcattggta tcaccgtctg ggtgtctct gacaagaact cttggcgcaa 960
ggagcacgac agtcttctgt tcgatgctaa ctacaacccc aagcctgctt acactgctgt 1020
tgtcaacgct ctccgctaa 1039

<210> SEQ ID NO 11
<211> LENGTH: 987
<212> TYPE: DNA
<213> ORGANISM: Fusarium verticillioides

<400> SEQUENCE: 11
atgaagctgt cttctttcct ctacaccgcc tcgctggtcg cggccattcc caccgccatc 60
gagccccgcc aggctgccga cagcatcaac aagctgatca agaacaaggg caagctctac 120
tacggaacca tcaccgaccc caacctgctc ggcgtcgcaa aggacaccgc catcatcaag 180
gccgactttg gcgccgttac ccccgagaac tcgggcaagt gggacgccac cgagcccagc 240
cagggcaagt tcaacttcgg tagcttcgac caggttgtca actttgccca gcagaatggc 300
ctcaaggtcc gaggtcacac tctggtctgg cactctcagc tccctcagtg ggttaagaac 360
atcaacgaca aggctactct gaccaaggtc attgagaacc acgtcaccca agtcgttgga 420
cgctacaagg gcaagatcta cgcctgggac gtcgtcaacg agatcttcga gtgggacggt 480
accctccgaa aggactctca cttcaacaac gtcttcggca acgacgacta cgttggcatt 540
gccttccgcg ccgcccgcaa ggctgacccc aacgccaagc tgtacatcaa cgactacagc 600
ctcgactccg gcagcgcctc caaggtcacc aagggtatgg ttccctccgt caagaagtgg 660
ctcagccagg gcgttcccgt cgacggcatt ggctctcaga ctcaccttga ccccggtgcc 720
gctggccaaa tccagggtgc tctcactgcc ctcgccaatt ctggtgtcaa ggaggttgcc 780
atcaccgagc tcgacatccg cactgccccc gccaacgact acgctaccgt caccaaggcc 840

```
tgcctcaacg tcccccaagtg cattggtatc accgtctggg gtgtctctga caagaactct    900
tggcgcaagg agcacgacag tcttctgttc gatgctaact acaaccccaa gcctgcttac    960
actgctgttg tcaacgctct ccgctaa                                        987
```

<210> SEQ ID NO 12
<211> LENGTH: 328
<212> TYPE: PRT
<213> ORGANISM: Fusarium oxysporum

<400> SEQUENCE: 12

```
Met Lys Leu Ser Ser Phe Leu Tyr Thr Ala Ser Leu Val Ala Ala Ile
1               5                   10                  15

Pro Thr Ala Ile Glu Pro Arg Gln Ala Ser Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Asn Val Val Gly Arg Tyr Lys Gly
    130                 135                 140

Lys Ile Tyr Ala Trp Asp Val Val Asn Glu Ile Phe Asp Trp Asp Gly
145                 150                 155                 160

Thr Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
                245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
        275                 280                 285

Gly Ile Thr Val Trp Gly Val Ser Asp Lys Asn Ser Trp Arg Lys Glu
    290                 295                 300

His Asp Ser Leu Leu Phe Asp Ala Asn Tyr Asn Pro Lys Ala Ala Tyr
305                 310                 315                 320

Thr Ala Val Val Asn Ala Leu Arg
                325
```

<210> SEQ ID NO 13

<211> LENGTH: 313
<212> TYPE: PRT
<213> ORGANISM: Fusarium oxysporum

<400> SEQUENCE: 13

```
Ile Pro Thr Ala Ile Glu Pro Arg Gln Ala Ser Asp Ser Ile Asn Lys
1               5                   10                  15
Leu Ile Lys Asn Lys Gly Lys Leu Tyr Tyr Gly Thr Ile Thr Asp Pro
            20                  25                  30
Asn Leu Leu Gly Val Ala Lys Asp Thr Ala Ile Ile Lys Ala Asp Phe
        35                  40                  45
Gly Ala Val Thr Pro Glu Asn Ser Gly Lys Trp Asp Ala Thr Glu Pro
    50                  55                  60
Ser Gln Gly Lys Phe Asn Phe Gly Ser Phe Asp Gln Val Val Asn Phe
65                  70                  75                  80
Ala Gln Gln Asn Gly Leu Lys Val Arg Gly His Thr Leu Val Trp His
                85                  90                  95
Ser Gln Leu Pro Gln Trp Val Lys Asn Ile Asn Asp Lys Ala Thr Leu
            100                 105                 110
Thr Lys Val Ile Glu Asn His Val Thr Asn Val Val Gly Arg Tyr Lys
        115                 120                 125
Gly Lys Ile Tyr Ala Trp Asp Val Val Asn Glu Ile Phe Asp Trp Asp
    130                 135                 140
Gly Thr Leu Arg Lys Asp Ser His Phe Asn Asn Val Phe Gly Asn Asp
145                 150                 155                 160
Asp Tyr Val Gly Ile Ala Phe Arg Ala Ala Arg Lys Ala Asp Pro Asn
                165                 170                 175
Ala Lys Leu Tyr Ile Asn Asp Tyr Ser Leu Asp Ser Gly Ser Ala Ser
            180                 185                 190
Lys Val Thr Lys Gly Met Val Pro Ser Val Lys Lys Trp Leu Ser Gln
        195                 200                 205
Gly Val Pro Val Asp Gly Ile Gly Ser Gln Thr His Leu Asp Pro Gly
    210                 215                 220
Ala Ala Gly Gln Ile Gln Gly Ala Leu Thr Ala Leu Ala Asn Ser Gly
225                 230                 235                 240
Val Lys Glu Val Ala Ile Thr Glu Leu Asp Ile Arg Thr Ala Pro Ala
                245                 250                 255
Asn Asp Tyr Ala Thr Val Thr Lys Ala Cys Leu Asn Val Pro Lys Cys
            260                 265                 270
Ile Gly Ile Thr Val Trp Gly Val Ser Asp Lys Asn Ser Trp Arg Lys
        275                 280                 285
Glu His Asp Ser Leu Leu Phe Asp Ala Asn Tyr Asn Pro Lys Ala Ala
    290                 295                 300
Tyr Thr Ala Val Val Asn Ala Leu Arg
305                 310
```

<210> SEQ ID NO 14
<211> LENGTH: 1039
<212> TYPE: DNA
<213> ORGANISM: Fusarium oxysporum

<400> SEQUENCE: 14

```
atgaagctgt cttccttcct ctacaccgcc tcgctggtcg cggccattcc caccgccatc      60
gagccccgcc aggcctccga cagcatcaac aagctgatca gaacaagggg caagctctac     120
tacggaacca tcaccgaccc caacctgctc ggcgtcgcaa aggacactgc catcatcaag     180
```

```
gctgactttg gcgccgtcac acccgagaac tcgggtaagt gggatgccac cgagcccagc    240
cagggcaagt tcaacttcgg cagcttcgac caggtcgtca actttgctca gcagaatggc    300
ctcaaggtcc gaggtcacac tctagtctgg cactcccagc tccctcagtg ggttaagaac    360
atcaacgaca aggctacttt gaccaaggtc atcgagaacc acgtcaccaa cgtcgttgga    420
cgctacaagg gcaagatcta cgcctgggta tgttttcttc actcgaactt cttataaatg    480
gctttactaa catgttcagg acgtcgttaa cgagatcttc gactgggatg gtaccctccg    540
aaaggactct cacttcaaca acgtcttcgg caacgacgac tacgttggca ttgccttccg    600
cgctgcccgc aaggctgacc ccaacgccaa gctgtacatc aacgactaca gcctcgactc    660
cggcagcgcc tccaaggtca ccaagggcat ggttccctct gtcaagaagt ggctcagcca    720
gggcgtcccc gtcgacggta ttggttctca gactcacctt gaccccggtg ccgctggcca    780
aatccagggt gctctcactg ccctcgccaa ctctggtgtg aaggaggttg ccatcaccga    840
gctcgacatc cgcactgccc ccgccaacga ctacgctacc gttaccaagg cctgcctcaa    900
cgtccccaag tgcattggta tcaccgtctg gggcgtatct gacaagaact cttggcgcaa    960
ggagcacgac agccttctgt tcgatgctaa ctacaacccc aaggctgctt acactgctgt   1020
tgtcaacgct ctccgctaa                                                1039
```

<210> SEQ ID NO 15
<211> LENGTH: 987
<212> TYPE: DNA
<213> ORGANISM: Fusarium oxysporum

<400> SEQUENCE: 15

```
atgaagctgt cttccttcct ctacaccgcc tcgctggtcg cggccattcc caccgccatc     60
gagccccgcc aggcctccga cagcatcaac aagctgatca gaacaaggg caagctctac    120 tacggaacca tcaccgaccc caacctgctc ggcgtcgcaa aggacactgc catcatcaag    180
gctgactttg gcgccgtcac acccgagaac tcgggtaagt gggatgccac cgagcccagc    240
cagggcaagt tcaacttcgg cagcttcgac caggtcgtca actttgctca gcagaatggc    300
ctcaaggtcc gaggtcacac tctagtctgg cactcccagc tccctcagtg ggttaagaac    360
atcaacgaca aggctacttt gaccaaggtc atcgagaacc acgtcaccaa cgtcgttgga    420
cgctacaagg gcaagatcta cgcctgggac gtcgttaacg agatcttcga ctgggatggt    480
accctccgaa aggactctca cttcaacaac gtcttcggca acgacgacta cgttggcatt    540
gccttccgct gcccgcaa ggctgacccc aacgccaagc tgtacatcaa cgactacagc     600
ctcgactccg gcagcgcctc caaggtcacc aagggcatgg ttccctctgt caagaagtgg    660
ctcagccagg gcgtccccgt cgacggtatt ggttctcaga ctcaccttga ccccggtgcc    720
gctggccaaa tccagggtgc tctcactgcc ctcgccaact ctggtgtgaa ggaggttgcc    780
atcaccgagc tcgacatccg cactgccccc gccaacgact acgctaccgt taccaaggcc    840
tgcctcaacg tccccaagtg cattggtatc accgtctggg gcgtatctga caagaactct    900
tggcgcaagg agcacgacag ccttctgttc gatgctaact acaaccccaa ggctgcttac    960
actgctgttg tcaacgctct ccgctaa                                        987
```

<210> SEQ ID NO 16
<211> LENGTH: 305
<212> TYPE: PRT
<213> ORGANISM: Fusarium sp.

<400> SEQUENCE: 16

Gln Ala Ala Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Thr Ala Val Ile Lys Ala Asp Phe Gly Ala Val Thr Pro Glu Asn Ser
        35                  40                  45

Gly Lys Trp Asp Ala Thr Glu Pro Ser Gln Gly Asn Phe Asn Phe Gly
    50                  55                  60

Ser Phe Asp Gln Val Val Asn Phe Ala Gln Gln Asn Gly Leu Lys Val
65                  70                  75                  80

Arg Gly His Thr Leu Val Trp His Ser Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Asp Trp Asp Gly Thr Leu Arg Lys Asp Ser His
    130                 135                 140

Phe Asn Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Ala Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Ser His Leu Asp Pro Gly Ala Ala Gly Gln Val Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ser Asn Tyr Asn Pro Lys Pro Ala Tyr Thr Ala Val Val Asn Ala Leu
    290                 295                 300

Arg
305

<210> SEQ ID NO 17
<211> LENGTH: 1039
<212> TYPE: DNA
<213> ORGANISM: Fusarium sp.

<400> SEQUENCE: 17
atgaagctgt cttctttcct ctacaccgcc tcgctggtcg cggccattcc caccgccatc      60
gagccccgcc aggccgccga cagcatcaac aagctgatca gaacaagggg caagctctac     120
tacggaacca tcaccgaccc caacctgctc ggcgtcgcaa aggacaccgc cgtcatcaag     180
gccgactttg gcgccgtcac ccccgagaac tcgggcaagt gggacgccac cgagcccagc     240
cagggcaact tcaacttcgg tagcttcgac caggtcgtca actttgctca gcagaatggc     300

```
ctcaaggtcc gaggtcacac tctggtctgg cactctcagc tccctcagtg ggttaagaac    360
atcaacgaca aggctactct gaccaaggtc attgagaacc acgtcaccca agtcgttgga    420
cgctacaagg gcaagatcta cgcctgggta tgttttcttg cctcgacctt ctcaaagatg    480
aatttgctaa catgttcagg acgttgtcaa cgagatcttc gactgggacg gtaccctccg    540
aaaggattct cacttcaaca acgtcttcgg caacgatgac tacgttggca ttgccttccg    600
cgccgcccgc aaggctgacc ccaacgccaa gctgtacatc aacgactaca gcctcgactc    660
cgccagcgcc tccaaggtca ccagggcat ggtcccctcc gtcaagaagt ggctcagcca    720
gggcgttccc gtcgacggca ttggctccca gtctcacctt gaccccggtg ccgctggcca    780
agtccagggt gctctcactg ccctcgccaa ctctggtgtc aaggaggttg ccatcaccga    840
gctcgacatc cgcactgccc ccgccaacga ctacgccacc gtcaccaagg cctgcctaaa    900
cgtccccaag tgcattggta tcaccgtctg gggtgtctct gacaagaact cttggcgcaa    960
ggagcacgac agccttctgt tcgactccaa ctacaacccc aagcctgctt acactgctgt   1020
tgtcaacgct ctccgctaa                                                1039
```

<210> SEQ ID NO 18
<211> LENGTH: 987
<212> TYPE: DNA
<213> ORGANISM: Fusarium sp.

<400> SEQUENCE: 18

```
atgaagctgt cttctttcct ctacaccgcc tcgctggtcg cggccattcc caccgccatc     60
gagccccgcc aggccgccga cagcatcaac aagctgatca agaacaaggg caagctctac    120
tacggaacca tcaccgaccc caacctgctc ggcgtcgcaa aggacaccgc cgtcatcaag    180
gccgactttg gcgccgtcac ccccgagaac tcgggcaagt gggacgccac cgagcccagc    240
cagggcaact tcaacttcgg tagcttcgac caggtcgtca actttgctca gcagaatggc    300
ctcaaggtcc gaggtcacac tctggtctgg cactctcagc tccctcagtg ggttaagaac    360
atcaacgaca aggctactct gaccaaggtc attgagaacc acgtcaccca agtcgttgga    420
cgctacaagg gcaagatcta cgcctgggac gttgtcaacg agatcttcga ctgggacggt    480
accctccgaa aggattctca cttcaacaac gtcttcggca acgatgacta cgttggcatt    540
gccttccgcg ccgcccgcaa ggctgacccc aacgccaagc tgtacatcaa cgactacagc    600
ctcgactccg ccagcgcctc caaggtcacc aagggcatgg tcccctccgt caagaagtgg    660
ctcagccagg gcgttcccgt cgacggcatt ggctcccagt ctcaccttga ccccggtgcc    720
gctggccaag tccagggtgc tctcactgcc ctcgccaact ctggtgtcaa ggaggttgcc    780
atcaccgagc tcgacatccg cactgccccc gccaacgact acgccaccgt caccaaggcc    840
tgcctaaacg tccccaagtg cattggtatc accgtctggg gtgtctctga caagaactct    900
tggcgcaagg agcacgacag ccttctgttc gactccaact acaaccccaa gcctgcttac    960
actgctgttg tcaacgctct ccgctaa                                        987
```

<210> SEQ ID NO 19
<211> LENGTH: 942
<212> TYPE: DNA
<213> ORGANISM: Fusarium sp.

<400> SEQUENCE: 19

```
attcccaccg ccatcgagcc ccgccaggcc gccgacagca tcaacaagct gatcaagaac     60
```

```
aagggcaagc tctactacgg aaccatcacc gaccccaacc tgctcggcgt cgcaaaggac    120
accgccgtca tcaaggccga ctttggcgcc gtcaccccccg agaactcggg caagtgggac   180
gccaccgagc ccagccaggg caacttcaac ttcggtagct tcgaccaggt cgtcaacttt    240
gctcagcaga atggcctcaa ggtccgaggt cacactctgg tctggcactc tcagctccct    300
cagtgggtta agaacatcaa cgacaaggct actctgacca aggtcattga gaaccacgtc    360
acccaagtcg ttggacgcta caagggcaag atctacgcct gggacgttgt caacgagatc    420
ttcgactggg acggtaccct ccgaaaggat tctcacttca acaacgtctt cggcaacgat    480
gactacgttg gcattgcctt ccgcgccgcc cgcaaggctg accccaacgc aagctgtac    540
atcaacgact acagcctcga ctccgccagc gcctccaagg tcaccaaggg catggtcccc    600
tccgtcaaga gtggctcag ccagggcgtt cccgtcgacg gcattggctc ccagtctcac    660
cttgaccccg gtgccgctgg ccaagtccag ggtgctctca ctgccctcgc caactctggt    720
gtcaaggagg ttgccatcac cgagctcgac atccgcactg cccccgccaa cgactacgcc    780
accgtcacca aggcctgcct aaacgtcccc aagtgcattg gtatcaccgt ctggggtgtc    840
tctgacaaga actcttggcg caaggagcac gacagcctttc tgttcgactc caactacaac    900
cccaagcctg cttacactgc tgttgtcaac gctctccgct aa                      942

<210> SEQ ID NO 20
<211> LENGTH: 328
<212> TYPE: PRT
<213> ORGANISM: Fusarium oxysporum

<400> SEQUENCE: 20

Met Lys Leu Ser Ser Phe Leu Tyr Thr Ala Ser Leu Val Ala Ala Ile
1               5                   10                  15

Pro Thr Ala Ile Glu Pro Arg Gln Ala Ser Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Asn Val Val Gly Arg Tyr Lys Gly
    130                 135                 140

Lys Ile Tyr Ala Trp Asp Val Val Asn Glu Ile Phe Asp Trp Asp Gly
145                 150                 155                 160

Ser Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220
```

```
Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
            245                 250                 255

Lys Glu Val Ala Ile Thr Glu Leu Asp Ile Arg Thr Pro Ala Asn
        260                 265                 270

Asp Tyr Ala Thr Val Thr Lys Ala Cys Leu Asn Val Pro Lys Cys Ile
            275                 280                 285

Gly Ile Thr Val Trp Gly Val Ser Asp Lys Asn Ser Trp Arg Lys Glu
            290                 295                 300

His Asp Ser Leu Leu Phe Asp Ala Asn Tyr Asn Pro Lys Ala Ala Tyr
305                 310                 315                 320

Thr Ala Val Val Asn Ala Leu Arg
                325

<210> SEQ ID NO 21
<211> LENGTH: 328
<212> TYPE: PRT
<213> ORGANISM: Fusarium oxysporum f. sp. lycopersici

<400> SEQUENCE: 21

Met Lys Leu Ser Ser Phe Leu Tyr Thr Ala Ser Leu Val Ala Ala Ile
1               5                   10                  15

Pro Thr Ala Ile Glu Pro Arg Gln Ala Ser Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Met Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Val Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Asn Val Val Gly Arg Tyr Lys Gly
    130                 135                 140

Lys Ile Tyr Ala Trp Asp Val Val Asn Glu Ile Phe Asp Trp Asp Gly
145                 150                 155                 160

Thr Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
            245                 250                 255

Lys Glu Val Ala Ile Thr Glu Leu Asp Ile Arg Thr Ala Pro Ala Asn
        260                 265                 270
```

```
                260                 265                 270
Asp Tyr Ala Thr Val Thr Lys Ala Cys Leu Asn Val Pro Lys Cys Ile
            275                 280                 285

Gly Ile Thr Val Trp Gly Val Ser Asp Lys Asn Ser Trp Arg Lys Glu
        290                 295                 300

His Asp Ser Leu Leu Phe Asp Ala Asn Tyr Asn Pro Lys Ala Ala Tyr
305                 310                 315                 320

Thr Ala Val Val Asn Ala Leu Arg
                325

<210> SEQ ID NO 22
<211> LENGTH: 327
<212> TYPE: PRT
<213> ORGANISM: Fusarium pseudograminearum

<400> SEQUENCE: 22

Met Lys Phe Ser Ser Leu Leu Phe Thr Ala Ser Leu Val Ala Ala Met
1               5                   10                  15

Pro Ala Ser Ile Glu Pro Arg Gln Ala Gln Asn Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gln Ser Gln Asn Asn Ala Ile Ile Lys Ala Asp Phe Gly
50                  55                  60

Gln Val Thr Pro Glu Asn Ser Met Lys Trp Asp Ala Thr Glu Pro Gln
65                  70                  75                  80

Gln Gly Lys Phe Asn Phe Gly Gly Gly Asp Gln Val Val Asn Phe Ala
                85                  90                  95

Ser Gln Asn Gly Leu Lys Val Arg Gly His Ala Leu Val Trp His Leu
            100                 105                 110

Gln Leu Pro Gln Trp Val His Asn Ile Lys Asp Lys Thr Gln Met Lys
        115                 120                 125

Asn Ala Ile Glu Asn His Ile Lys Asn Val Ala Gly His Phe Lys Gly
    130                 135                 140

Lys Val Tyr Ala Trp Asp Val Leu Asn Glu Ile Phe Asp Trp Asp Gly
145                 150                 155                 160

Ser Leu Arg Lys Asp Ser Pro Phe Thr Gln Val Leu Gly Glu Glu Phe
                165                 170                 175

Val Gly Ile Ala Phe Arg Ala Ala Arg Ala Ala Asp Pro Asn Ala Lys
            180                 185                 190

Leu Tyr Ile Asn Asp Tyr Ser Ile Asp Asp Pro Asn Ala Lys Leu
        195                 200                 205

Lys Ala Gly Met Val Ala His Val Lys Lys Trp Val Ser Gln Gly Ile
    210                 215                 220

Pro Ile Asp Gly Ile Gly Ser Gln Thr His Leu Asp Pro Gly Ala Ala
225                 230                 235                 240

Asn Gly Val Gln Ala Ala Leu Gln Gln Met Ala Ser Thr Gly Val Lys
                245                 250                 255

Glu Val Ala Ile Thr Glu Leu Asp Ile Arg Ser Ala Pro Ala Ala Asp
            260                 265                 270

Tyr Ala Thr Val Thr Lys Ala Cys Leu Asn Val Pro Lys Cys Val Gly
        275                 280                 285

Ile Thr Val Trp Gly Val Ser Asp Lys Asp Ser Trp Arg Lys Glu Lys
    290                 295                 300
```

Asp Ser Leu Leu Phe Asn Ala Gln Tyr Gln Ala Lys Pro Ala Tyr Thr
305                 310                 315                 320

Ala Val Val Asn Ala Leu Arg
            325

<210> SEQ ID NO 23
<211> LENGTH: 327
<212> TYPE: PRT
<213> ORGANISM: Gibberella zeae

<400> SEQUENCE: 23

Met Lys Phe Ser Ser Leu Leu Phe Thr Ala Ser Leu Val Ala Ala Met
1               5                   10                  15

Pro Ala Ser Ile Glu Pro Arg Gln Ala Gln Glu Ser Ile Asn Lys Leu
            20                  25                  30

Ile Lys Ala Lys Gly Lys Leu Tyr Tyr Gly Thr Ile Thr Asp Pro Asn
        35                  40                  45

Leu Leu Gln Ser Gln Gln Asn Asn Ala Val Ile Lys Ala Asp Phe Gly
    50                  55                  60

Gln Val Thr Pro Glu Asn Ser Met Lys Trp Asp Ala Thr Glu Pro Gln
65                  70                  75                  80

Gln Gly Lys Phe Asn Phe Gly Gly Asp Gln Val Val Asn Phe Ala
                85                  90                  95

Ala Gln Asn Gly Leu Lys Val Arg Gly His Ala Leu Val Trp His Ser
            100                 105                 110

Gln Leu Pro Gln Trp Val His Asn Ile Lys Asp Lys Thr Gln Met Lys
        115                 120                 125

Asn Ala Ile Glu Asn His Ile Lys Asn Val Ala Gly His Phe Lys Gly
    130                 135                 140

Lys Val Tyr Ala Trp Asp Val Leu Asn Glu Ile Phe Asp Trp Asp Gly
145                 150                 155                 160

Ser Leu Arg Lys Asp Ser Pro Phe Thr Gln Val Leu Gly Glu Glu Phe
                165                 170                 175

Val Gly Ile Ala Phe Arg Ala Ala Arg Ala Ala Asp Pro Asn Ala Lys
            180                 185                 190

Leu Tyr Ile Asn Asp Tyr Ser Ile Asp Asp Pro Asn Ala Ala Lys Leu
        195                 200                 205

Lys Ala Gly Met Val Ala His Val Lys Lys Trp Val Ser Gln Gly Ile
    210                 215                 220

Pro Ile Asp Gly Ile Gly Ser Gln Thr His Leu Asp Pro Gly Ala Ala
225                 230                 235                 240

Asn Gly Val Gln Ala Ala Leu Gln Gln Met Ala Ser Thr Gly Val Lys
                245                 250                 255

Glu Val Ala Ile Thr Glu Leu Asp Ile Arg Ser Ala Pro Ala Ala Asp
            260                 265                 270

Tyr Ala Thr Val Thr Lys Ala Cys Leu Asn Val Pro Lys Cys Val Gly
        275                 280                 285

Ile Thr Val Trp Gly Val Ser Asp Lys Asp Ser Trp Arg Lys Glu Lys
    290                 295                 300

Asp Ser Leu Leu Phe Asn Ala Gln Tyr Gln Ala Lys Pro Ala Tyr Thr
305                 310                 315                 320

Ala Val Val Asn Ala Leu Arg
            325

<210> SEQ ID NO 24

<211> LENGTH: 327
<212> TYPE: PRT
<213> ORGANISM: Gibberella zeae

<400> SEQUENCE: 24

Met Lys Phe Ser Ser Leu Leu Phe Thr Ala Ser Leu Val Ala Ala Met
1               5                   10                  15

Pro Ala Ser Ile Glu Pro Arg Gln Ala Gln Glu Ser Ile Asn Lys Leu
            20                  25                  30

Ile Lys Ala Lys Gly Lys Leu Tyr Tyr Gly Thr Ile Thr Asp Pro Asn
        35                  40                  45

Leu Leu Gln Ser Gln Gln Asn Asn Ala Val Ile Lys Ala Asp Phe Gly
    50                  55                  60

Gln Val Thr Pro Glu Asn Ser Met Lys Trp Asp Ala Thr Glu Pro Gln
65                  70                  75                  80

Gln Gly Lys Phe Asn Phe Gly Gly Asp Gln Val Val Asn Phe Ala
                85                  90                  95

Ser Gln Asn Gly Leu Lys Val Arg Gly His Ala Leu Val Trp His Ser
            100                 105                 110

Gln Leu Pro Gln Trp Val His Asn Ile Lys Asp Lys Thr Gln Met Lys
        115                 120                 125

Asn Ala Ile Glu Asn His Ile Lys Asn Val Ala Gly His Phe Lys Gly
    130                 135                 140

Lys Val Tyr Ala Trp Asp Val Leu Asn Glu Ile Phe Asp Trp Asp Gly
145                 150                 155                 160

Ser Leu Arg Lys Asp Ser Pro Phe Thr Gln Val Leu Gly Glu Glu Phe
                165                 170                 175

Val Gly Ile Ala Phe Arg Ala Ala Arg Ala Ala Asp Pro Asn Ala Lys
            180                 185                 190

Leu Tyr Ile Asn Asp Tyr Ser Ile Asp Asp Pro Asn Ala Ala Arg Leu
        195                 200                 205

Lys Ala Gly Met Val Ala His Val Lys Lys Trp Val Ser Gln Gly Ile
    210                 215                 220

Pro Ile Asp Gly Ile Gly Ser Gln Thr His Leu Asp Pro Gly Ala Ala
225                 230                 235                 240

Asn Gly Val Gln Ala Ala Leu Gln Gln Met Ala Ser Thr Gly Val Lys
                245                 250                 255

Glu Val Ala Ile Thr Glu Leu Asp Ile Arg Ser Ala Pro Ala Ala Asp
            260                 265                 270

Tyr Ala Thr Val Thr Lys Ala Cys Leu Asn Val Pro Lys Cys Val Gly
        275                 280                 285

Ile Thr Val Trp Gly Val Ser Asp Lys Asp Ser Trp Arg Lys Glu Lys
    290                 295                 300

Asp Ser Leu Leu Phe Asn Ala Gln Tyr Gln Ala Lys Pro Ala Tyr Thr
305                 310                 315                 320

Ala Val Val Asn Ala Leu Arg
                325

<210> SEQ ID NO 25
<211> LENGTH: 326
<212> TYPE: PRT
<213> ORGANISM: Nectria haematococca

<400> SEQUENCE: 25

Met Lys Phe Ser Ser Phe Leu Phe Ala Ala Ser Leu Val Ala Ala Ala
1               5                   10                  15

```
Pro Ala Asn Val Glu Pro Arg Gln Ser Pro Asn Ser Ile Asn Lys Leu
            20                  25                  30

Ile Ile Asn Lys Gly Lys Lys Tyr Tyr Gly Thr Ile Thr Asp Pro Asn
        35                  40                  45

Leu Leu Ser Asn Gln Lys Asn Asn Ala Ile Ile Lys Ala Asn Phe Gly
    50                  55                  60

Gln Val Thr Ala Glu Asn Ser Met Lys Trp Asp Ala Thr Glu Pro Gln
65                  70                  75                  80

Arg Gly Gln Phe Asn Phe Ala Gly Ala Asp Gln Val Val Asn Phe Ala
                85                  90                  95

Gln Gln Asn Gly Leu Lys Val Arg Gly His Thr Leu Leu Trp His Ser
            100                 105                 110

Gln Leu Pro Gln Trp Val Gln Ser Ile Asn Asp Arg Asn Thr Leu Thr
        115                 120                 125

Gln Val Ile Glu Asn His Ile Lys Thr Val Ala Gly Arg Tyr Lys Gly
    130                 135                 140

Lys Ile Tyr Ala Trp Asp Val Val Asn Glu Ile Phe Glu Trp Asp Gly
145                 150                 155                 160

Arg Leu Arg Asp Ser Val Phe Ser Arg Val Leu Gly Glu Asp Phe Val
                165                 170                 175

Gly Ile Ala Phe Arg Ala Ala Arg Ala Ala Asp Pro Asn Ala Lys Leu
            180                 185                 190

Tyr Ile Asn Asp Tyr Ser Leu Asp Ser Ala Asn Ala Ala Lys Val Thr
        195                 200                 205

Thr Gly Met Val Ala His Val Lys Lys Trp Ile Ala Ala Gly Ile Pro
    210                 215                 220

Ile Asp Gly Ile Gly Ser Gln Thr His Leu Asp Pro Gly Ala Ala Ser
225                 230                 235                 240

Gly Ile Gln Gly Ala Leu Gln Ala Leu Ala Gly Ser Gly Val Ser Glu
                245                 250                 255

Val Ala Ile Thr Glu Leu Asp Ile Ala Ser Ala Pro Ala Asn Asp Tyr
            260                 265                 270

Ala Thr Val Thr Lys Ala Cys Leu Asn Val Pro Lys Cys Val Gly Ile
        275                 280                 285

Thr Val Trp Gly Val Arg Asp Gln Asp Ser Trp Arg Thr Gly Lys Asn
    290                 295                 300

Pro Leu Leu Phe Asp Asn Asn Tyr Ser Pro Lys Pro Ala Tyr Asp Ala
305                 310                 315                 320

Val Val Gln Ala Leu Arg
                325

<210> SEQ ID NO 26
<211> LENGTH: 334
<212> TYPE: PRT
<213> ORGANISM: Verticillium albo-atrum

<400> SEQUENCE: 26

Met Lys Phe Ser Gln Ile His Leu Ala Leu Leu Leu Ala Pro Leu Ala
1               5                   10                  15

Ala Val Ala Ser Pro Val Pro Glu Ala Ala Ser His Val Glu Ser Arg
            20                  25                  30

Gln Ala Ala Ala Ser Ile Asp Lys Leu Phe Lys Ala Lys Gly Lys Leu
        35                  40                  45

Tyr Ile Gly Val Ala Thr Asp Arg Gly Leu Leu Gln Thr Gly Lys Asn
```

```
            50                  55                  60
Ala Ala Ile Ile Gln Gln Asp Phe Gly Gln Val Thr Pro Glu Asn Ser
 65                  70                  75                  80

Met Lys Trp Asp Ala Leu Glu Pro Ser Arg Gly Ser Phe Asn Phe Ala
                     85                  90                  95

Gly Ala Asp Phe Leu Val Asp Trp Ala Gln Thr Asn Ser Lys Ser Ile
                100                 105                 110

Arg Gly His Thr Leu Val Trp His Ser Gln Leu Pro Gln Trp Val Lys
                115                 120                 125

Asp Ile Lys Asp Arg Asp Leu Thr Asn Val Ile Glu Asn His Val
130                 135                 140

Lys Thr Ile Val Thr Arg Tyr Lys Gly Lys Ile Arg Ala Trp Asp Val
145                 150                 155                 160

Val Asn Glu Ile Phe Asn Glu Asp Gly Thr Met Arg Ser Ser Val Phe
                165                 170                 175

Ser Asp Ile Leu Gly Glu Asp Phe Val Gly Ile Ala Phe Arg Ala Ala
                180                 185                 190

Arg Ala Ala Asp Pro Asn Ala Lys Leu Tyr Ile Asn Asp Tyr Asn Leu
                195                 200                 205

Asp Arg Ala Asn Tyr Gly Lys Val Asn Gly Leu Val Ser Lys Val Asn
210                 215                 220

Lys Trp Ile Thr Ala Gly Val Pro Ile Asp Gly Ile Gly Ser Gln Thr
225                 230                 235                 240

His Leu Asp Ala Gly Ala Ala Gly Asn Ile Lys Gly Val Leu Gln Gln
                245                 250                 255

Leu Ala Ser Ala Gln Val Ser Glu Val Ala Ile Thr Glu Leu Asp Ile
                260                 265                 270

Lys Thr Ala Pro Ala Ala Asp Phe Ala Thr Ile Val Gly Ala Cys Leu
                275                 280                 285

Asp Val Pro Lys Cys Lys Gly Ile Thr Val Trp Gly Val Ser Asp Lys
                290                 295                 300

Asp Ser Trp Arg Gln Gly Thr Asn Pro Leu Leu Phe Asp Ala Asp Tyr
305                 310                 315                 320

Asn Pro Lys Ala Ala Tyr Thr Ala Ile Val Thr Lys Leu Ser
                325                 330

<210> SEQ ID NO 27
<211> LENGTH: 325
<212> TYPE: PRT
<213> ORGANISM: Aspergillus fumigatus

<400> SEQUENCE: 27

Met Val Val Leu Ser Lys Leu Val Ser Ser Ile Leu Phe Ala Ser Leu
 1               5                  10                  15

Val Ser Ala Gly Val Ile Glu Glu Arg Gln Ala Ala Ser Ile Asn Gln
                20                  25                  30

Ala Phe Thr Ser His Gly Lys Arg Tyr Phe Gly Thr Ala Ser Asp Gln
                35                  40                  45

Ala Leu Leu Gln Lys Ser Gln Asn Glu Ala Ile Val Arg Lys Asp Phe
 50                  55                  60

Gly Gln Leu Thr Pro Glu Asn Ser Met Lys Trp Asp Ala Thr Glu Pro
 65                  70                  75                  80

Ser Gln Gly Arg Phe Asn Phe Ala Gly Ala Asp Phe Leu Val Asn Tyr
                 85                  90                  95
```

```
Ala Lys Gln Asn Gly Lys Lys Val Arg Gly His Thr Leu Val Trp His
            100                 105                 110

Ser Gln Leu Pro Ser Trp Val Ser Ala Ile Ser Asp Lys Asn Thr Leu
            115                 120                 125

Thr Ser Val Leu Lys Asn His Ile Thr Thr Val Met Thr Arg Tyr Lys
130                 135                 140

Gly Gln Ile Tyr Ala Trp Asp Val Val Asn Glu Ile Phe Asn Glu Asp
145                 150                 155                 160

Gly Ser Leu Arg Asp Ser Val Phe Ser Arg Val Leu Gly Glu Asp Phe
                165                 170                 175

Val Arg Ile Ala Phe Glu Thr Ala Arg Ser Val Asp Pro Ser Ala Lys
            180                 185                 190

Leu Tyr Ile Asn Asp Tyr Asn Leu Asp Ser Ala Ser Tyr Gly Lys Thr
            195                 200                 205

Gln Gly Met Val Arg Cys Val Lys Lys Trp Leu Ala Ala Gly Ile Pro
            210                 215                 220

Ile Asp Gly Ile Gly Thr Gln Thr His Leu Gly Ala Gly Ala Ser Ser
225                 230                 235                 240

Ser Val Lys Gly Ala Leu Thr Ala Leu Ala Ser Ser Gly Val Ser Glu
                245                 250                 255

Val Ala Ile Thr Glu Leu Asp Ile Ala Gly Ala Ser Ser Gln Asp Tyr
            260                 265                 270

Val Asn Val Val Lys Ala Cys Leu Asp Val Pro Lys Cys Val Gly Ile
            275                 280                 285

Thr Val Trp Gly Val Ser Asp Arg Asp Ser Trp Arg Ser Gly Ser Ser
290                 295                 300

Pro Leu Leu Phe Asp Ser Asn Tyr Gln Pro Lys Ala Ala Tyr Asn Ala
305                 310                 315                 320

Ile Ile Ala Ala Leu
            325

<210> SEQ ID NO 28
<211> LENGTH: 334
<212> TYPE: PRT
<213> ORGANISM: Verticillium dahliae

<400> SEQUENCE:

```
Lys Thr Ile Val Thr Arg Tyr Lys Gly Lys Ile Arg Ala Trp Asp Val
145                 150                 155                 160

Val Asn Glu Ile Phe Asn Glu Asp Gly Thr Met Arg Ser Ser Val Phe
            165                 170                 175

Ser Asp Val Leu Gly Glu Asp Phe Val Gly Ile Ala Phe Arg Ala Ala
            180                 185                 190

Arg Ala Ala Asp Pro Asn Ala Lys Leu Tyr Ile Asn Asp Tyr Asn Leu
        195                 200                 205

Asp Arg Ala Asn Tyr Gly Lys Val Asn Gly Leu Val Ser Lys Val Asn
    210                 215                 220

Lys Trp Ile Thr Ala Gly Val Pro Ile Asp Gly Ile Gly Ser Gln Thr
225                 230                 235                 240

His Leu Asp Ala Gly Ala Ala Gly Asn Ile Lys Gly Val Leu Gln Gln
            245                 250                 255

Leu Ala Ser Thr Gln Val Ser Glu Val Ala Ile Thr Glu Leu Asp Ile
            260                 265                 270

Lys Met Ala Pro Ala Ala Asp Phe Ala Thr Val Val Gly Ala Cys Leu
        275                 280                 285

Asp Val Pro Lys Cys Lys Gly Ile Thr Val Trp Gly Val Ser Asp Lys
    290                 295                 300

Asp Ser Trp Arg Lys Gly Ala Asn Pro Leu Leu Phe Asp Gly Asp Tyr
305                 310                 315                 320

Asn Pro Lys Ala Ala Tyr Thr Ala Ile Val Thr Lys Leu Ser
            325                 330

<210> SEQ ID NO 29
<211> LENGTH: 325
<212> TYPE: PRT
<213> ORGANISM: Aspergillus fumigatus

<400> SEQUENCE: 29

Met Val Val Leu Ser Lys Leu Val Ser Ser Ile Leu Phe Val Ser Leu
1               5                   10                  15

Val Ser Ala Gly Val Ile Glu Glu Arg Gln Ala Ala Ser Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
    50                  55                  60

Gly Gln Leu Thr Pro Glu Asn Ser Met Lys Trp Asp Ala Thr Glu Pro
65                  70                  75                  80

Ser Gln Gly Arg Phe Asn Phe Ala Gly Ala Asp Phe Leu Val Asn Tyr
            85                  90                  95

Ala Lys Gln Asn Gly Lys Lys Val Arg Gly His Thr Leu Val Trp His
        100                 105                 110

Ser Gln Leu Pro Ser Trp Val Ser Ala Ile Ser Asp Lys Asn Thr Leu
    115                 120                 125

Thr Ser Val Leu Lys Asn His Ile Thr Thr Val Met Thr Arg Tyr Lys
130                 135                 140

Gly Gln Ile Tyr Ala Trp Asp Val Val Asn Glu Ile Phe Asn Glu Asp
145                 150                 155                 160

Gly Ser Leu Arg Asp Ser Val Phe Ser Arg Val Leu Gly Glu Asp Phe
            165                 170                 175

Val Arg Ile Ala Phe Glu Thr Ala Arg Ser Val Asp Pro Ser Ala Lys
```

```
                    180                 185                 190
Leu Tyr Ile Asn Asp Tyr Asn Leu Asp Ser Ala Ser Tyr Gly Lys Thr
                195                 200                 205

Gln Gly Met Val Arg Tyr Val Lys Lys Trp Leu Ala Ala Gly Ile Pro
            210                 215                 220

Ile Asp Gly Ile Gly Thr Gln Thr His Leu Gly Ala Gly Ala Ser Ser
225                 230                 235                 240

Ser Val Lys Gly Ala Leu Thr Ala Leu Ala Ser Ser Gly Val Ser Glu
                245                 250                 255

Val Ala Ile Thr Glu Leu Asp Ile Ala Gly Ala Ser Ser Gln Asp Tyr
            260                 265                 270

Val Asn Val Val Lys Ala Cys Leu Asp Val Pro Lys Cys Val Gly Ile
                275                 280                 285

Thr Val Trp Gly Val Ser Asp Arg Asp Ser Trp Arg Ser Gly Ser Ser
            290                 295                 300

Pro Leu Leu Phe Asp Ser Asn Tyr Gln Pro Lys Ala Ala Tyr Asn Ala
305                 310                 315                 320

Ile Ile Ala Ala Leu
                325

<210> SEQ ID NO 30
<211> LENGTH: 330
<212> TYPE: PRT
<213> ORGANISM: Glomerella graminicola

<400> SEQUENCE: 30

Met Lys Phe Ser Met Ser Leu Val Cys Leu Leu Ala Pro Ile Thr Val
1               5                   10                  15

Leu Ala Ala Pro Leu Glu Gly Gly Leu Glu Gln Arg Gln Ala Ala Gln
                20                  25                  30

Ser Val Asp Arg Leu Ile Lys Ala Lys Gly Lys Lys Tyr Phe Gly Thr
            35                  40                  45

Cys Ser Asp Gln Gly Arg Leu Thr Ser Gly Lys Asn Ala Ala Ile Ile
50                  55                  60

Asn Ala Asp Phe Gly Gln Leu Thr Pro Glu Asn Ser Met Lys Trp Asp
65                  70                  75                  80

Gln Ile Gln Pro Asn Asn Gly Gln Phe Asn Trp Ala Gly Ala Asp Tyr
                85                  90                  95

Leu Val Asn Phe Ala Gln Gln Asn Gly Lys Leu Val Arg Gly His Thr
                100                 105                 110

Leu Val Trp His Ser Gln Leu Ala Ser Tyr Val Gln Asn Ile Arg Asp
            115                 120                 125

Lys Ala Thr Leu Thr Lys Thr Ile Gln Asp His Ile Ser Ala Val Val
        130                 135                 140

Gly Arg Tyr Lys Gly Lys Ile Tyr Ala Trp Asp Val Val Asn Glu Ile
145                 150                 155                 160

Phe Asp Glu Ser Gly Asn Leu Arg Ser Ser Val Phe Ser Gln Val Leu
                165                 170                 175

Gly Glu Asp Phe Val Gly Ile Ala Phe Arg Ala Ala Arg Ala Ala Asp
            180                 185                 190

Pro Asn Ala Lys Leu Tyr Ile Asn Asp Tyr Asn Leu Asp Gln Ala Ser
        195                 200                 205

Tyr Ala Lys Thr Gln Ala Met Ala Arg Lys Val Lys Gln Trp Ile Gly
    210                 215                 220
```

```
Gln Gly Ile Pro Ile Asp Gly Ile Gly Ser Gln Ala His Leu Gln Ala
225                 230                 235                 240

Asn Gln Gly Gly Asn Ala Leu Gly Ala Leu Gln Thr Leu Ala Gly Ser
            245                 250                 255

Gly Val Lys Glu Val Ala Ile Thr Glu Leu Asp Ile Val Gly Ala Ser
        260                 265                 270

Ser Asn Asp Tyr Ser Ala Val Thr Arg Ala Cys Leu Gln Val Pro Gln
    275                 280                 285

Cys Val Gly Ile Thr Val Trp Gly Val Arg Asp Pro Asp Ser Trp Arg
290                 295                 300

Ala Gln Asn Asn Pro Leu Leu Phe Asp Ala Asn Trp Asn Pro Lys Ala
305                 310                 315                 320

Ala Tyr Asn Ala Val Val Ser Ala Leu Gln
                325                 330

<210> SEQ ID NO 31
<211> LENGTH: 326
<212> TYPE: PRT
<213> ORGANISM: Glomerella graminicola

<400> SEQUENCE: 31

Met Lys Phe Ser Thr Ser Leu Val Cys Leu Leu Ala Pro Ile Thr Ala
1               5                   10                  15

Leu Ala Ala Pro Ile Glu Glu Arg Gln Ala Ser Gln Ser Ile Asp Lys
            20                  25                  30

Leu Phe Lys Ala Lys Gly Lys Gln Tyr Tyr Gly Asn Ile Ala Asp Pro
        35                  40                  45

Asn Leu Ile Asn Asn Ala Lys Asn Ala Ala Ile Leu Lys Ala Asp Phe
50                  55                  60

Gly Val Leu Thr Pro Glu Asn Ser Met Lys Trp Gln Ser Ile Glu Pro
65                  70                  75                  80

Thr Gln Gly Lys Phe Asn Trp Ala Gly Ala Asp Ala Leu Val Asp Phe
                85                  90                  95

Ala Thr Lys Asn Gly Gln Lys Val Arg Gly His Thr Leu Val Trp His
            100                 105                 110

Ser Gln Leu Ala Ser Tyr Val Ser Asn Ile Lys Asp Lys Ala Thr Leu
        115                 120                 125

Thr Lys Ala Ile Glu Glu His Ile Ser Ala Val Val Gly Arg Tyr Lys
    130                 135                 140

Gly Lys Ile Met His Trp Asp Val Val Asn Glu Met Phe Asn Glu Asp
145                 150                 155                 160

Gly Ser Leu Arg Pro Ser Val Phe Ser Asn Val Leu Gly Glu Asp Phe
                165                 170                 175

Val Arg Ile Ala Phe Lys Ala Ala Lys Ala Ala Asp Pro Asn Ala Leu
            180                 185                 190

Leu Phe Ile Asn Asp Phe Asn Leu Asp Ser Ala Asn Ser Ala Lys Thr
        195                 200                 205

Lys Ala Met Ala Asn Lys Val Lys Gln Trp Ile Ala Gln Gly Ile Pro
    210                 215                 220

Ile Asp Gly Ile Gly Ser Gln Thr His Leu Asn Pro Gly Gln Ala Ala
225                 230                 235                 240

Gly Val Ala Gly Ala Leu Lys Thr Leu Ala Ser Ser Gly Val Lys His
                245                 250                 255

Val Ala Ile Thr Glu Leu Asp Ile Ala Gly Ala Asn Pro Asn Asp Tyr
            260                 265                 270
```

```
Ser Thr Val Thr Lys Ala Cys Leu Asp Leu Pro Gln Cys Val Gly Ile
        275                 280                 285

Ser Val Trp Gly Val Arg Asp Ser Asp Ser Trp Arg Thr Gly Ala Asn
290                 295                 300

Pro Leu Leu Phe Asp Ala Asn Phe Gln Pro Lys Gln Ala Tyr Asn Ala
305                 310                 315                 320

Val Ala Gln Val Ile Gly
                325
```

<210> SEQ ID NO 32
<211> LENGTH: 331
<212> TYPE: PRT
<213> ORGANISM: Magnaporthe oryzae

<400> SEQUENCE: 32

```
Met Lys Ala Ser Ser Val Leu Leu Gly Leu Ala Pro Leu Ala Ala Leu
1               5                   10                  15

Ala Ala Pro Thr Pro Glu Ala Glu Leu Ser Ala Arg Gln Ala Gln Gln
                20                  25                  30

Ser Ile Asp Ala Leu Met Lys Ala Lys Gly Lys Leu Tyr Phe Gly Thr
            35                  40                  45

Ala Thr Asp Gln Gly Leu Leu Asn Thr Gly Lys Asn Ser Ala Ile Ile
50                  55                  60

Lys Ala Asp Phe Gly Gln Val Thr Pro Glu Asn Ser Met Lys Trp Gln
65                  70                  75                  80

Ser Leu Glu Asn Thr Arg Gly Gln Tyr Asn Trp Ala Pro Ala Asp Ala
                85                  90                  95

Leu Val Asn Phe Ala Val Ser Asn Asn Lys Ser Ile Arg Gly His Thr
            100                 105                 110

Leu Ile Trp His Ser Gln Leu Pro Gly Trp Val Asn Asn Ile Asn Asp
        115                 120                 125

Arg Asn Gln Leu Thr Thr Val Ile Gln Asn His Val Ala Thr Val Met
130                 135                 140

Gly Arg Trp Lys Gly Lys Ile Arg Ala Trp Asp Val Val Asn Glu Ile
145                 150                 155                 160

Phe Asn Glu Asp Gly Thr Met Arg Gln Ser Val Phe Ser Arg Val Leu
                165                 170                 175

Gly Glu Asp Phe Val Arg Ile Ala Phe Glu Ala Ala Arg Lys Ala Asp
            180                 185                 190

Pro Asn Ala Lys Leu Tyr Ile Asn Asp Tyr Asn Leu Asp Ser Pro Asn
        195                 200                 205

Ala Ala Lys Leu Thr Lys Gly Met Val Ala His Val Lys Lys Trp Leu
210                 215                 220

Ala Ala Gly Val Pro Ile Asp Gly Ile Gly Ser Gln Gly His Leu Gln
225                 230                 235                 240

Ser Gly Gln Gly Asn Gly Leu Ala Gln Ala Ile Lys Ala Leu Ala Asp
                245                 250                 255

Ser Gly Val Lys Glu Val Ala Val Thr Glu Leu Asp Ile Gln Gly Asn
            260                 265                 270

Asn Ala Asn Asp Tyr Ala Ala Val Thr Lys Gly Cys Leu Ala Val Pro
        275                 280                 285

Ala Cys Val Gly Ile Thr Ala Trp Gly Val Arg Asp Asn Asp Ser Trp
290                 295                 300

Arg Pro Gln Gly Asn Pro Leu Leu Phe Asp Ser Asn Tyr Asn Pro Lys
```

Ala Ala Tyr Asn Ser Val Val Gln Ala Leu Lys
305             310             315             320

<210> SEQ ID NO 33
<211> LENGTH: 330
<212> TYPE: PRT
<213> ORGANISM: Penicillium oxalicum

<400> SEQUENCE: 33

Met Val Gln Ile Lys Ala Ala Ile Ala Leu Ile Phe Ala Gly Ser
1               5                   10                  15

Ala Ile Ala Ala Pro Ala Glu Thr Leu Glu Ser Arg Gln Ala Thr
                20                  25                  30

Ser Ile Asp Ala Lys Phe Lys Ala His Gly Lys Lys Tyr Phe Gly Asn
                35                  40                  45

Ile Ala Asp Gln Tyr Thr Leu Thr Lys Ser Pro Lys Pro Ala Ala Ile
50                  55                  60

Ile Lys Ala Asp Phe Gly Gln Leu Thr Pro Glu Asn Ser Met Lys Trp
65                  70                  75                  80

Asp Ala Thr Glu Pro Ser Arg Gly Lys Phe Asn Phe Gly Gly Ser Asp
                85                  90                  95

Tyr Leu Val Asn Phe Ala Thr Gln Asn Asn Lys Met Ile Arg Gly His
                100                 105                 110

Thr Leu Val Trp His Ser Gln Leu Pro Gln Trp Val Gln Asn Ile Asn
            115                 120                 125

Asp Arg Asn Thr Leu Thr Gln Val Leu Lys Asp His Ile Thr Asn Val
130                 135                 140

Met Gly Arg Tyr Lys Gly Lys Ile Tyr Ala Trp Asp Val Val Asn Glu
145                 150                 155                 160

Ile Phe Asn Glu Asp Gly Ser Leu Arg Asn Ser Val Phe Tyr Arg Val
                165                 170                 175

Leu Gly Glu Asp Phe Val Arg Ile Ala Phe Glu Thr Ala Arg Ala Thr
                180                 185                 190

Asp Pro Asn Ala Lys Leu Tyr Ile Asn Asp Tyr Asn Leu Asp Asn Ala
                195                 200                 205

Asn Tyr Gly Lys Thr Lys Gly Met Ile Ser His Val Lys Lys Trp Ile
210                 215                 220

Ser Gln Gly Ile Pro Ile Asp Gly Ile Gly Ser Gln Ser His Leu Glu
225                 230                 235                 240

Ala Gly Met Gly Ala Gly Val Ser Ala Ala Leu Asn Ala Leu Ala Thr
                245                 250                 255

Ala Gly Thr Lys Glu Val Ala Ile Thr Glu Leu Asp Ile Ala Gly Ala
                260                 265                 270

Ser Ser Thr Asp Tyr Val Asn Val Ala Lys Ala Cys Leu Asn Gln Pro
275                 280                 285

Lys Cys Val Gly Ile Thr Val Trp Gly Val Ser Asp Asn Asp Ser Trp
                290                 295                 300

Arg Ser Asp Lys Ser Pro Cys Leu Phe Asp Arg Asn Tyr Asn Val Lys
305                 310                 315                 320

Pro Ala Tyr Asn Ala Ile Thr Thr Ala Leu
                325                 330

<210> SEQ ID NO 34
<211> LENGTH: 330

<212> TYPE: PRT
<213> ORGANISM: Paecilomyces aerugineus

<400> SEQUENCE: 34

Met Val Gln Ile Lys Ala Ala Ile Ala Leu Ile Phe Ala Gly Ser
1               5                   10                  15

Ala Ile Ala Ala Pro Ala Glu Thr Leu Glu Ser Arg Gln Ala Ala Thr
            20                  25                  30

Ser Ile Asp Ala Lys Phe Lys Ala His Gly Lys Lys Tyr Phe Gly Asn
        35                  40                  45

Ile Ala Asp Gln Tyr Thr Leu Thr Lys Ser Pro Lys Pro Ala Ala Ile
    50                  55                  60

Ile Lys Ala Asp Phe Gly Gln Leu Thr Pro Glu Asn Ser Met Lys Trp
65                  70                  75                  80

Asp Ala Thr Glu Pro Ser Arg Gly Lys Phe Asn Phe Gly Gly Ser Asp
                85                  90                  95

Tyr Leu Val Asn Phe Ala Thr Gln Asn Asn Lys Met Ile Arg Gly His
            100                 105                 110

Thr Leu Val Trp His Ser Gln Leu Pro Gln Trp Val Gln Asn Ile Asn
        115                 120                 125

Asp Arg Asn Thr Leu Thr Gln Val Leu Lys Asp His Ile Thr Asn Val
    130                 135                 140

Met Gly Arg Tyr Lys Gly Lys Ile Tyr Ala Trp Asp Val Val Asn Glu
145                 150                 155                 160

Ile Phe Asn Glu Asp Gly Ser Leu Arg Asn Ser Val Phe Tyr Arg Val
                165                 170                 175

Leu Gly Glu Asp Phe Val Arg Ile Ala Phe Glu Thr Ala Arg Ala Thr
            180                 185                 190

Asp Pro Asn Ala Lys Leu Tyr Ile Asn Asp Tyr Asn Leu Asp Asn Ala
        195                 200                 205

Asn Tyr Gly Lys Thr Lys Gly Met Ile Ser His Val Lys Lys Trp Ile
    210                 215                 220

Ser Gln Gly Ile Pro Ile Asp Gly Ile Gly Ser Gln Ser His Leu Glu
225                 230                 235                 240

Ala Gly Met Gly Ala Gly Val Ser Ala Ala Leu Asn Ala Leu Ala Thr
                245                 250                 255

Ala Gly Thr Lys Glu Val Ala Ile Thr Glu Leu Asp Ile Ala Gly Ala
            260                 265                 270

Ser Ser Thr Asp Tyr Val Asn Val Ala Lys Ala Cys Leu Asn Gln Pro
        275                 280                 285

Lys Cys Val Gly Ile Thr Val Trp Gly Val Ser Asp Asn Asp Ser Trp
    290                 295                 300

Arg Ser Asp Lys Ser Pro Cys Leu Phe Asp Arg Asn Tyr Asn Val Lys
305                 310                 315                 320

Pro Ala Tyr Asn Ala Ile Thr Ala Ala Leu
                325                 330

<210> SEQ ID NO 35
<211> LENGTH: 317
<212> TYPE: PRT
<213> ORGANISM: Aspergillus clavatus

<400> SEQUENCE: 35

Met Val Val Leu Ser Lys Ile Phe Ser Cys Ala Leu Phe Leu Ser Leu
1               5                   10                  15

```
Gly Ser Ala Ala Ala Ile Asp Ile Arg Gln Thr Ser Ser Ile Asn Asn
                20                  25                  30

Ala Phe Lys Ser His Gly Lys Lys Tyr Phe Gly Thr Cys Gly Asp Gln
            35                  40                  45

Asn Thr Leu Ser Ile Pro Gln Asn Ser Ala Ile Ile Lys Ala Asp Phe
50                  55                  60

Gly Ala Leu Thr Pro Glu Asn Ser Met Lys Trp Asp Ala Thr Glu Pro
65                  70                  75                  80

Ser Arg Gly Lys Phe Asn Phe Ala Gly Ala Asp His Leu Val Asn Tyr
                85                  90                  95

Ala Lys Gln Asn Gly Lys Leu Val Arg Gly His Thr Leu Val Trp Tyr
            100                 105                 110

Ser Gln Leu Pro Ala Trp Val Lys Ala Ile Ser Asp Lys Gln Thr Leu
        115                 120                 125

Thr Ser Val Leu Lys Asn His Ile Thr Thr Val Met Ser Arg Tyr Lys
130                 135                 140

Gly Gln Val Tyr Ala Trp Asp Val Val Asn Glu Ile Phe Glu Glu Asn
145                 150                 155                 160

Gly Ser Leu Arg Asn Ser Val Phe Tyr Arg Val Leu Gly Glu Asp Phe
                165                 170                 175

Val Arg Ile Ala Phe Glu Thr Ala Arg Ala Val Asp Pro His Ala Lys
            180                 185                 190

Leu Tyr Ile Asn Asp Tyr Asn Leu Asp Ser Ala Asn Tyr Gly Lys Thr
        195                 200                 205

Gln Ala Met Val Lys His Val Lys Lys Trp Leu Ala Ala Gly Ile Pro
210                 215                 220

Ile Asp Gly Ile Gly Ser Gln Ser His Leu Ser Gln Ala Leu Ser Ala
225                 230                 235                 240

Leu Ala Ser Thr Gly Val Ser Glu Ile Ala Ile Thr Glu Leu Asp Ile
                245                 250                 255

Lys Gly Ala Asn Pro Ser Glu Tyr Val Ala Val Thr Lys Ala Cys Leu
            260                 265                 270

Glu Val Lys Lys Cys Ile Gly Ile Thr Val Trp Gly Val Ser Asp Lys
        275                 280                 285

Asn Ser Trp Arg Lys Asp Asn Ser Pro Leu Leu Phe Asp Arg Asn Tyr
290                 295                 300

Asn Pro Lys Pro Ala Tyr Asn Ala Ile Ile Ala Leu
305                 310                 315

<210> SEQ ID NO 36
<211> LENGTH: 316
<212> TYPE: PRT
<213> ORGANISM: Aspergillus fumigatus

<400> SEQUENCE: 36

Met Val Val Leu Ser Lys Leu Val Ser Ser Ile Leu Phe Val Ser Leu
1               5                   10                  15

Val Ser Ala Gly Val Ile Glu Glu Arg Gln Ala Ala Ser Ile Asn Gln
                20                  25                  30

Ala Phe Thr Ser His Gly Lys Lys Tyr Phe Gly Thr Ala Ser Asp Gln
            35                  40                  45

Ala Leu Leu Gln Lys Ser Gln Asn Glu Ala Ile Val Arg Lys Asp Phe
        50                  55                  60

Gly Gln Leu Thr Pro Glu Asn Ser Met Lys Trp Asp Ala Thr Glu Pro
65                  70                  75                  80
```

-continued

```
Ser Gln Gly Arg Phe Asn Phe Ala Gly Ala Asp Phe Leu Val Asn Tyr
                85                  90                  95

Ala Lys Gln Asn Gly Lys Lys Val Arg Gly His Thr Leu Val Trp His
            100                 105                 110

Ser Gln Leu Pro Ser Trp Val Ser Ala Ile Ser Asp Lys Asn Thr Leu
        115                 120                 125

Thr Ser Val Leu Lys Asn His Ile Thr Thr Val Met Thr Arg Tyr Lys
130                 135                 140

Gly Gln Ile Tyr Ala Trp Asp Val Val Asn Glu Ile Phe Asn Glu Asp
145                 150                 155                 160

Gly Ser Leu Arg Asp Ser Val Phe Ser Arg Val Leu Gly Glu Asp Phe
                165                 170                 175

Val Arg Ile Ala Phe Glu Thr Ala Arg Ser Val Asp Pro Ser Ala Lys
            180                 185                 190

Leu Tyr Ile Asn Asp Tyr Asn Leu Asp Ser Ala Ser Tyr Gly Lys Thr
        195                 200                 205

Gln Gly Met Val Arg Tyr Val Lys Lys Trp Leu Ala Ala Gly Ile Pro
210                 215                 220

Ile Asp Gly Ile Gly Thr Gln Thr His Leu Gly Ala Leu Thr Ala Leu
225                 230                 235                 240

Ala Ser Ser Gly Val Ser Glu Val Ala Ile Thr Glu Leu Asp Ile Ala
                245                 250                 255

Gly Ala Ser Ser Gln Asp Tyr Val Asn Val Val Lys Ala Cys Leu Asp
            260                 265                 270

Val Pro Lys Cys Val Gly Ile Thr Val Trp Gly Val Ser Asp Arg Asp
        275                 280                 285

Ser Trp Arg Ser Gly Ser Pro Leu Leu Phe Asp Ser Asn Tyr Gln
290                 295                 300

Pro Lys Ala Ala Tyr Asn Ala Ile Ile Ala Ala Leu
305                 310                 315
```

<210> SEQ ID NO 37
<211> LENGTH: 323
<212> TYPE: PRT
<213> ORGANISM: Aspergillus sojae

<400> SEQUENCE: 37

```
Met Val His Leu Lys Ser Leu Ala Gly Ile Leu Leu Tyr Thr Ser Leu
1               5                   10                  15

Cys Ile Ala Ser Ser Gln Gln Ala Pro Ala Ser Ile Asn Asn Ala Phe
            20                  25                  30

Val Thr Lys Gly Lys Lys Tyr Phe Gly Thr Cys Ala Asp Gln Gly Thr
        35                  40                  45

Leu Ser Asp Gly Thr Asn Ser Gly Ile Ile Lys Ala Asp Phe Gly Gln
    50                  55                  60

Leu Thr Pro Glu Asn Ser Met Lys Trp Asp Ala Thr Glu Pro Ser Gln
65                  70                  75                  80

Gly Lys Phe Ser Phe Ser Gly Ala Asp Tyr Leu Val Asn Tyr Ala Ala
                85                  90                  95

Thr Asn Asn Lys Leu Ile Arg Gly His Thr Leu Val Trp His Ser Gln
            100                 105                 110

Leu Pro Ser Trp Val Gln Gly Ile Thr Asp Lys Asn Thr Leu Thr Ser
        115                 120                 125

Val Leu Lys Asn His Ile Thr Thr Val Met Asn Arg Tyr Lys Gly Lys
```

```
                130                 135                 140
Val Tyr Ala Trp Asp Val Val Asn Glu Ile Phe Asn Glu Asp Gly Thr
145                 150                 155                 160

Leu Arg Ser Ser Val Phe Tyr Lys Val Leu Gly Glu Asp Phe Val Arg
                165                 170                 175

Ile Ala Phe Glu Ala Ala Arg Ala Ala Asp Pro Gln Ala Lys Leu Tyr
            180                 185                 190

Ile Asn Asp Tyr Asn Leu Asp Ser Ala Asn Tyr Gly Lys Thr Thr Gly
            195                 200                 205

Leu Ala Asn His Val Lys Lys Trp Ile Ala Gln Gly Ile Pro Ile Asp
            210                 215                 220

Gly Ile Gly Ser Gln Thr His Leu Ser Ala Gly Ser Ser Gly Val
225                 230                 235                 240

Lys Gly Ala Leu Asn Ile Leu Ala Ser Gly Val Ser Glu Val Ala
                245                 250                 255

Ile Thr Glu Leu Asp Ile Ala Gly Ala Ser Ser Asn Asp Tyr Val Asn
                260                 265                 270

Val Val Lys Ala Cys Leu Glu Val Ser Lys Cys Val Gly Ile Thr Val
            275                 280                 285

Trp Gly Val Ser Asp Lys Asn Ser Trp Arg Ser Ala Glu Ser Pro Leu
290                 295                 300

Leu Phe Asp Gly Asn Tyr Gln Pro Lys Thr Ala Tyr Asn Ala Ile Leu
305                 310                 315                 320

Asn Ala Leu

<210> SEQ ID NO 38
<211> LENGTH: 323
<212> TYPE: PRT
<213> ORGANISM: Aspergillus oryzae

<400> SEQUENCE: 38

Met Val His Leu Lys Ser Leu Ala Gly Ile Leu Leu Tyr Thr Ser Leu
1               5                   10                  15

Cys Ile Ala Ser Ser Gln Gln Ala Pro Ala Ser Ile Asn Asn Ala Phe
            20                  25                  30

Val Ala Lys Gly Lys Lys Tyr Phe Gly Thr Cys Ala Asp Gln Gly Thr
        35                  40                  45

Leu Ser Asp Gly Thr Asn Ser Gly Ile Ile Lys Ala Asp Phe Gly Gln
50                  55                  60

Leu Thr Pro Glu Asn Ser Met Lys Trp Asp Ala Thr Glu Pro Ser Gln
65                  70                  75                  80

Gly Lys Phe Ser Phe Ser Gly Ala Asp Tyr Leu Val Asn Tyr Ala Ala
                85                  90                  95

Thr Asn Asn Lys Leu Ile Arg Gly His Thr Leu Val Trp His Ser Gln
            100                 105                 110

Leu Pro Ser Trp Val Gln Gly Ile Thr Asp Lys Asn Thr Leu Thr Ser
        115                 120                 125

Val Leu Lys Asn His Ile Thr Thr Val Met Asn Arg Tyr Lys Gly Lys
130                 135                 140

Val Tyr Ala Trp Asp Val Val Asn Glu Ile Phe Asn Glu Asp Gly Thr
145                 150                 155                 160

Leu Arg Ser Ser Val Phe Tyr Asn Val Leu Gly Glu Asp Phe Val Arg
                165                 170                 175

Ile Ala Phe Glu Thr Ala Arg Ala Ala Asp Pro Gln Ala Lys Leu Tyr
```

```
            180                 185                 190
Ile Asn Asp Tyr Asn Leu Asp Ser Ala Asn Tyr Gly Lys Thr Thr Gly
            195                 200                 205
Leu Ala Asn His Val Lys Lys Trp Ile Ala Gln Gly Ile Pro Ile Asp
            210                 215                 220
Gly Ile Gly Ser Gln Thr His Leu Ser Ala Gly Gly Ser Ser Gly Val
225                 230                 235                 240
Lys Gly Ala Leu Asn Thr Leu Ala Ala Ser Gly Val Ser Glu Val Ala
                245                 250                 255
Ile Thr Glu Leu Asp Ile Ala Gly Ala Ser Ser Asn Asp Tyr Val Asn
            260                 265                 270
Val Val Glu Ala Cys Leu Glu Val Ser Lys Cys Val Gly Ile Thr Val
            275                 280                 285
Trp Gly Val Ser Asp Lys Asn Ser Trp Arg Ser Ala Glu Ser Pro Leu
            290                 295                 300
Leu Phe Asp Gly Asn Tyr Gln Pro Lys Ser Ala Tyr Asn Ala Ile Leu
305                 310                 315                 320

Asn Ala Leu

<210> SEQ ID NO 39
<211> LENGTH: 355
<212> TYPE: PRT
<213> ORGANISM: Trichoderma pseudokoningii

<400> SEQUENCE: 39

Met Lys Ala Asn Val Ile Leu Cys Leu Leu Ala Pro Leu Ile Ala Ala
1               5                   10                  15
Leu Pro Thr Glu Pro Ile Pro Leu Asp Pro Glu Leu Ala Ala Leu Arg
            20                  25                  30
Ala Asn Leu Thr Glu Arg Thr Pro Asp Leu Trp Asp Arg Gln Ala Ala
        35                  40                  45
Gln Ser Ile Asp Gln Leu Ile Lys Arg Arg Gly Lys Leu Tyr Phe Gly
    50                  55                  60
Thr Ala Thr Asp Arg Gly Leu Leu Gln Arg Glu Lys Asn Ala Ala Ile
65                  70                  75                  80
Ile Gln Ala Asp Leu Gly Gln Val Thr Pro Glu Asn Ser Met Lys Trp
                85                  90                  95
Gln Ser Leu Glu Asn Asn Gln Gly Gln Tyr Asn Trp Gly Asp Ala Asp
            100                 105                 110
Tyr Leu Val Asn Phe Ala Gln Gln Asn Gly Lys Leu Ile Arg Gly His
        115                 120                 125
Thr Leu Ile Trp His Ser Gln Leu Pro Ala Trp Val Asn Asn Ile Asn
    130                 135                 140
Asn Ala Asp Thr Leu Arg Gln Val Ile Arg Thr His Val Ser Thr Val
145                 150                 155                 160
Val Gly Arg Tyr Lys Gly Lys Ile Arg Ala Trp Asp Val Val Asn Glu
                165                 170                 175
Ile Phe Asn Glu Asp Gly Thr Leu Val Phe Asn Glu Asp Gly Thr Leu
            180                 185                 190
Arg Ser Ser Val Phe Ser Arg Leu Leu Gly Glu Glu Phe Val Ser Ile
        195                 200                 205
Ala Phe Arg Ala Ala Arg Asp Ala Asp Pro Ser Ala Arg Leu Tyr Ile
    210                 215                 220
Asn Asp Tyr Asn Leu Asp Ser Ala Thr Tyr Gly Lys Val Asn Gly Leu
```

```
            225                 230                 235                 240

Lys Ser Tyr Val Ser Lys Trp Ile Ser Gln Gly Val Pro Ile Asp Gly
                245                 250                 255

Ile Gly Ser Gln Ser His Leu Ser Pro Gly Gly Ala Ser Gly Thr Leu
                260                 265                 270

Gly Ala Leu Gln Gln Leu Ala Thr Val Pro Val Thr Glu Val Ala Ile
                275                 280                 285

Thr Glu Leu Asp Ile Gln Gly Ala Pro Thr Asn Asp Tyr Thr Gln Val
            290                 295                 300

Val Gln Ala Cys Leu Asn Val Ser Lys Cys Val Gly Ile Thr Val Trp
305                 310                 315                 320

Gly Ile Ser Asp Lys Asp Ser Trp Arg Ala Ser Thr Asn Pro Leu Leu
                325                 330                 335

Phe Asp Ser Asn Phe Asn Pro Lys Pro Ala Tyr Asn Ser Ile Val Ser
                340                 345                 350

Ile Leu Gln
        355

<210> SEQ ID NO 40
<211> LENGTH: 327
<212> TYPE: PRT
<213> ORGANISM: Penicillium citrinum

<400> SEQUENCE: 40

Met Val Gln Ile Lys Thr Ala Ala Leu Ala Leu Phe Ala Gly Gln
1               5                   10                  15

Val Leu Ser Thr Pro Leu Glu Pro Arg Gln Ala Ser Val Ser Ile Asp
                20                  25                  30

Ala Lys Phe Lys Ala His Gly Lys Lys Tyr Phe Gly Asn Ile Gly Glu
            35                  40                  45

Gln Tyr Thr Phe Asn Arg Asn Ala Lys Thr Pro Ala Ile Ile Lys Ala
    50                  55                  60

Asp Phe Gly Gln Leu Thr Pro Glu Asn Ser Met Lys Trp Asp Ala Thr
65                  70                  75                  80

Glu Pro Asn Gln Gly Gln Phe Ser Phe Ser Gly Ser Asp Tyr Leu Val
                85                  90                  95

Asn Phe Ala Gln Ser Asn Gly Lys Leu Ile Arg Gly His Thr Leu Val
            100                 105                 110

Trp His Ser Gln Leu Pro Ser Trp Val Ser Ser Ile Ser Asp Lys Asn
        115                 120                 125

Thr Leu Ile Asn Val Met Lys Asn His Ile Thr Thr Val Met Asn Arg
    130                 135                 140

Tyr Lys Gly Lys Ile Tyr Ala Trp Asp Val Val Asn Glu Ile Phe Asn
145                 150                 155                 160

Glu Asp Gly Ser Leu Arg Asp Ser Val Phe Ser Arg Val Ile Gly Glu
                165                 170                 175

Asp Phe Val Arg Ile Ala Phe Glu Thr Ala Arg Ala Ala Asp Pro Asn
            180                 185                 190

Ala Lys Leu Tyr Ile Asn Asp Tyr Asn Leu Asp Ser Ala Ser Tyr Ser
        195                 200                 205

Lys Val Asn Gly Met Val Ser His Val Lys Lys Trp Ile Ala Ala Gly
    210                 215                 220

Ile Pro Ile Asp Gly Ile Gly Ser Gln Thr His Leu Gly Ala Gly Ala
225                 230                 235                 240
```

```
Gly Ser Ala Val Ser Gly Ala Leu Asn Ala Leu Ala Ser Ala Gly Thr
                245                 250                 255

Lys Glu Val Ala Ile Thr Glu Leu Asp Ile Ala Gly Ala Ser Ser Thr
            260                 265                 270

Asp Tyr Val Asn Val Asn Ala Cys Leu Asn Gln Pro Lys Cys Val
        275                 280                 285

Gly Ile Thr Val Trp Gly Val Ala Asp Pro Asp Ser Trp Arg Ala Ser
            290                 295                 300

Ser Asn Pro Leu Leu Phe Asp Gly Asn Tyr Asn Pro Lys Ala Ala Tyr
305                 310                 315                 320

Asn Ala Ile Ala Asn Ala Leu
                325
```

<210> SEQ ID NO 41
<211> LENGTH: 314
<212> TYPE: PRT
<213> ORGANISM: Neosartorya fischeri

<400> SEQUENCE: 41

```
Met Val Val Leu Ser Lys Leu Ile Ser Ser Ile Leu Phe Ala Ser Leu
1               5                   10                  15

Val Ser Ala Ala Val Ile Glu Arg Gln Ala Thr Ser Ile Asn Gln Ala
            20                  25                  30

Phe Thr Ser His Gly Lys Lys Tyr Phe Gly Thr Ala Ser Asp Gln Arg
        35                  40                  45

Leu Leu Gln Asn Ser Gln Asn Glu Ala Ile Val Arg Lys Asp Phe Gly
    50                  55                  60

Gln Leu Thr Pro Glu Asn Ser Met Lys Trp Asp Ala Thr Glu Pro Ser
65                  70                  75                  80

Arg Gly Ser Phe Asn Phe Ala Gly Ala Asp Phe Leu Val Asn Tyr Ala
                85                  90                  95

Lys Gln Asn Gly Met Lys Val Arg Gly His Thr Leu Val Trp His Ser
            100                 105                 110

Gln Leu Pro Ser Trp Val Ser Ala Ile Thr Asp Lys Asn Thr Leu Thr
        115                 120                 125

Ser Val Leu Lys Asn His Ile Thr Thr Val Met Thr Arg Tyr Lys Gly
    130                 135                 140

Gln Ile Tyr His Trp Asp Val Val Asn Glu Ile Phe Asn Glu Asp Gly
145                 150                 155                 160

Ser Leu Arg Asp Ser Val Phe Ser Arg Val Leu Gly Glu Asp Phe Val
                165                 170                 175

Arg Ile Ala Phe Glu Thr Ala Arg Ser Val Asp Pro Ser Ala Lys Leu
            180                 185                 190

Tyr Ile Asn Asp Tyr Asn Leu Asp Ser Ala Ser Tyr Gly Lys Thr Gln
        195                 200                 205

Gly Met Val Ser His Val Lys Lys Trp Leu Ala Ala Gly Ile Pro Ile
    210                 215                 220

Asp Gly Ile Gly Ser Gln Thr His Leu Ala Leu Thr Ala Leu Ala Ser
225                 230                 235                 240

Ser Gly Val Ser Glu Val Ala Ile Thr Glu Leu Asp Ile Ala Gly Ala
                245                 250                 255

Ser Ser Gln Asp Tyr Val Asn Val Val Asn Ala Cys Leu Gly Val Pro
            260                 265                 270

Lys Cys Val Gly Ile Thr Val Trp Gly Val Ser Asp Lys Asp Ser Trp
        275                 280                 285
```

Arg Ser Ser Ser Ser Pro Leu Leu Phe Asp Ser Asn Tyr Gln Pro Lys
            290                 295                 300

Ala Ala Tyr Asn Ala Ile Ile Ala Ala Leu
305                 310

<210> SEQ ID NO 42
<211> LENGTH: 330
<212> TYPE: PRT
<213> ORGANISM: Gaeumannomyces graminis

<400> SEQUENCE: 42

Met Arg Gly Leu Phe Ala Leu Leu Leu Pro Leu Ala Leu Ala Ala
1               5                   10                  15

Pro Thr Pro Glu Ala Gly Glu Leu Val Glu Arg Gln Ala Ala Gln Ser
            20                  25                  30

Ile Asp Arg Leu Met Lys Ala Lys Gly Lys Leu Tyr Tyr Gly Thr Ala
        35                  40                  45

Thr Asp Gln Gly Arg Leu Gly Gln Gly Lys Asn Ala Ala Val Ile Gln
    50                  55                  60

Gly Asn Phe Gly Gln Val Thr Pro Glu Asn Ser Met Lys Trp Glu Ser
65                  70                  75                  80

Ile Glu Arg Ser Lys Gly Gln Tyr Asn Trp Gly Gln Ala Asp Tyr Leu
                85                  90                  95

Val Asp Trp Ala Thr Lys Asn Asp Lys Ser Ile Arg Gly His Thr Leu
            100                 105                 110

Val Trp His Ser Gln Leu Pro Gly Trp Val Ser Asn Ile Asn Asn Lys
        115                 120                 125

Ala Glu Leu Thr Lys Val Ile Gln Asp His Val Ala Ala Val Val Gly
    130                 135                 140

Arg Tyr Lys Gly Lys Ile Arg Ala Trp Asp Val Leu Asn Glu Ile Phe
145                 150                 155                 160

Asn Glu Asp Gly Ser Leu Arg Ser Ser Val Phe Ser Arg Val Leu Gly
                165                 170                 175

Glu Asp Phe Val Arg Ile Thr Phe Glu Ala Ala Arg Lys Ala Asp Pro
            180                 185                 190

Asp Ala Val Leu Tyr Ile Asn Asp Tyr Asn Leu Asp Ser Pro Asn Ala
        195                 200                 205

Ala Lys Leu Thr Arg Gly Met Val Ala Asn Val Lys Lys Trp Ile Ser
    210                 215                 220

Gln Gly Ile Pro Ile Asp Gly Ile Gly Thr Gln Gly His Leu Gln Ser
225                 230                 235                 240

Gly Gln Gly Ser Ala Leu Ala Gly Ala Ile Lys Ala Leu Ala Asp Thr
                245                 250                 255

Gly Val Lys Glu Val Ala Val Thr Glu Leu Asp Ile Gln Asn Asn Asn
            260                 265                 270

Ala Asn Asp Tyr Ala Ala Val Thr Lys Gly Cys Leu Ala Val Lys Ser
        275                 280                 285

Cys Val Gly Ile Thr Val Trp Gly Val Arg Asp Gln Asp Ser Trp Arg
    290                 295                 300

Pro Gln Gly Asn Pro Leu Leu Phe Asp Ser Gly Phe Asn Ala Lys Ala
305                 310                 315                 320

Asn Tyr Asn Ala Ile Val Gln Ala Leu Gln
                325                 330

<210> SEQ ID NO 43
<211> LENGTH: 326
<212> TYPE: PRT
<213> ORGANISM: Aspergillus terreus

<400> SEQUENCE: 43

Met Val Arg Leu Thr Val Leu Ala Gly Phe Leu Leu Thr Ser Ala Ala
1               5                   10                  15

Cys Ser Ala Cys Val Ile Gly Glu Arg Gln Ala Ala Ser Ser Ile Asn
            20                  25                  30

Asn Ala Phe Lys Ala Lys Gly Lys Lys Tyr Phe Gly Thr Cys Gly Asp
        35                  40                  45

Gln Gly Thr Leu Ser Asp Ser Thr Asn Ser Ala Ile Val Lys Ala Asp
    50                  55                  60

Phe Gly Gln Leu Thr Pro Glu Asn Ser Met Lys Trp Asp Ala Thr Glu
65                  70                  75                  80

Pro Asn Arg Gly Gln Phe Ser Phe Gly Gly Ala Asp Tyr Leu Val Asn
                85                  90                  95

Tyr Ala Ala Ser Asn Gly Lys Met Ile Arg Gly His Thr Leu Val Trp
            100                 105                 110

His Ser Gln Leu Pro Gly Trp Val Gln Gly Ile Thr Asp Lys Asn Thr
        115                 120                 125

Leu Thr Ser Val Leu Lys Asn His Ile Thr Thr Val Met Gln Arg Tyr
    130                 135                 140

Lys Gly Lys Val Tyr Ala Trp Asp Val Val Asn Glu Ile Phe Asn Glu
145                 150                 155                 160

Asp Gly Ser Leu Arg Lys Ser Val Phe Tyr Asn Val Leu Gly Glu Asp
                165                 170                 175

Phe Val Arg Ile Ala Phe Glu Thr Ala Arg Ser Val Asp Pro Gln Ala
            180                 185                 190

Lys Leu Tyr Ile Asn Asp Tyr Asn Leu Asp Asn Ala Asn Tyr Ala Lys
        195                 200                 205

Thr Lys Gly Met Ala Asp His Val Arg Lys Trp Ile Ser Gln Gly Ile
    210                 215                 220

Pro Ile Asp Gly Ile Gly Ser Gln Thr His Leu Gly Ser Gly Gly Ser
225                 230                 235                 240

Trp Thr Val Lys Asp Ala Leu Asn Thr Leu Ala Ser Ser Gly Val Ser
                245                 250                 255

Glu Val Ala Ile Thr Glu Leu Asp Ile Ala Gly Ala Ser Ser Thr Asp
            260                 265                 270

Tyr Val Asn Val Val Asn Ala Cys Leu Ser Val Ser Lys Cys Val Gly
        275                 280                 285

Ile Thr Val Trp Gly Val Ser Asp Lys Tyr Ser Trp Arg Ser Asn Asp
    290                 295                 300

Lys Pro Leu Leu Phe Asp Ser Asn Phe Gln Pro Lys Ala Ala Tyr Asn
305                 310                 315                 320

Ala Ile Ile Ser Ala Leu
                325

<210> SEQ ID NO 44
<211> LENGTH: 326
<212> TYPE: PRT
<213> ORGANISM: Aspergillus terreus

<400> SEQUENCE: 44

Met Val Arg Leu Thr Val Leu Ala Gly Phe Leu Leu Thr Ser Ala Ala

```
              1               5                 10                15
          Cys Ser Ala Cys Val Ile Gly Glu Arg Gln Ala Ala Ser Ile Asn
                          20                 25               30

Asn Ala Phe Lys Ala Lys Gly Lys Tyr Phe Gly Thr Cys Gly Asp
                      35                 40                 45

Gln Gly Thr Leu Ser Asp Ser Thr Asn Ser Ala Ile Val Lys Ala Asp
                      50                  55                 60

Phe Gly Gln Leu Thr Pro Glu Asn Ser Met Lys Trp Asp Ala Thr Glu
          65                  70                 75                 80

Pro Asn Arg Gly Gln Phe Ser Phe Gly Gly Ala Asp Tyr Leu Val Asn
                              85                  90                 95

Tyr Ala Thr Ser Asn Gly Lys Met Ile Arg Gly His Thr Leu Val Trp
                          100                105                110

His Ser Gln Leu Pro Gly Trp Val Gln Gly Ile Thr Asp Lys Asn Thr
                          115                120                125

Leu Thr Ser Val Leu Lys Asn His Ile Thr Thr Val Met Gln Arg Tyr
                      130                 135                140

Lys Gly Lys Ile Tyr Ala Trp Asp Val Val Asn Glu Ile Phe Asn Glu
          145                 150                155                160

Asp Gly Ser Leu Arg Lys Ser Val Phe Tyr Asn Val Leu Gly Glu Asp
                              165                170                175

Phe Val Arg Ile Ala Phe Glu Thr Ala Arg Ser Val Asp Pro Gln Ala
                          180                185                190

Lys Leu Tyr Ile Asn Asp Tyr Asn Leu Asp Asn Ala Asn Tyr Ala Lys
                          195                200                205

Thr Lys Gly Met Ala Asp His Val Arg Lys Trp Ile Ser Gln Gly Ile
                      210                 215                220

Pro Ile Asp Gly Ile Gly Ser Gln Thr His Leu Gly Ser Gly Gly Ser
          225                 230                235                240

Trp Thr Val Lys Asp Ala Leu Asn Thr Leu Ala Ser Ser Gly Val Ser
                              245                250                255

Glu Val Ala Ile Thr Glu Leu Asp Ile Ala Gly Ala Ser Ser Thr Asp
                          260                265                270

Tyr Val Asn Val Val Asn Ala Cys Leu Ser Val Ser Lys Cys Val Gly
                      275                 280                285

Ile Thr Val Trp Gly Val Ser Asp Lys Tyr Ser Trp Arg Ser Asn Asp
          290                 295                300

Lys Pro Leu Leu Phe Asp Ser Asn Phe Gln Pro Lys Ala Ala Tyr Asn
          305                 310                315                320

Ala Ile Ile Ser Ala Leu
                          325
```

<210> SEQ ID NO 45
<211> LENGTH: 329
<212> TYPE: PRT
<213> ORGANISM: Thermoascus aurantiacus

<400> SEQUENCE: 45

```
          Met Val Arg Pro Thr Ile Leu Leu Thr Ser Leu Leu Leu Ala Pro Phe
          1                   5                  10                 15

Ala Ala Ala Ser Pro Ile Leu Glu Glu Arg Gln Ala Ala Gln Ser Val
                          20                 25                30

Asp Gln Leu Ile Lys Ala Arg Gly Lys Val Tyr Phe Gly Val Ala Thr
                      35                  40                45
```

```
Asp Gln Asn Arg Leu Thr Thr Gly Lys Asn Ala Ala Ile Ile Gln Ala
        50                  55                  60

Asp Phe Gly Gln Val Thr Pro Glu Asn Ser Met Lys Trp Asp Ala Thr
 65                  70                  75                  80

Glu Pro Ser Gln Gly Asn Phe Asn Phe Ala Gly Ala Asp Tyr Leu Val
                     85                  90                  95

Asn Trp Ala Gln Gln Asn Gly Lys Leu Ile Arg Gly His Thr Leu Val
                100                 105                 110

Trp His Ser Gln Leu Pro Ser Trp Val Ser Ser Ile Thr Asp Lys Asn
            115                 120                 125

Thr Leu Thr Asn Val Met Lys Asn His Ile Thr Thr Leu Met Thr Arg
        130                 135                 140

Tyr Lys Gly Lys Ile Arg Ala Trp Asp Val Val Asn Glu Ala Phe Asn
145                 150                 155                 160

Glu Asp Gly Ser Leu Arg Gln Thr Val Phe Leu Asn Val Ile Gly Glu
                    165                 170                 175

Asp Tyr Ile Pro Ile Ala Phe Gln Thr Ala Arg Ala Ala Asp Pro Asn
                180                 185                 190

Ala Lys Leu Tyr Ile Asn Asp Tyr Asn Leu Asp Ser Ala Ser Tyr Pro
            195                 200                 205

Lys Thr Gln Ala Ile Val Asn Arg Val Lys Gln Trp Arg Ala Ala Gly
        210                 215                 220

Val Pro Ile Asp Gly Ile Gly Ser Gln Thr His Leu Ser Ala Gly Gln
225                 230                 235                 240

Gly Ala Ser Val Leu Gln Ala Leu Pro Leu Leu Ala Ser Ala Gly Thr
                    245                 250                 255

Pro Glu Val Ala Ile Thr Glu Leu Asp Val Ala Gly Ala Ser Ser Thr
                260                 265                 270

Asp Tyr Val Asn Val Val Asn Ala Cys Leu Asn Val Gln Ser Cys Val
            275                 280                 285

Gly Ile Thr Val Trp Gly Val Ala Asp Pro Asp Ser Trp Arg Ala Ser
        290                 295                 300

Thr Thr Pro Leu Leu Phe Asp Gly Asn Phe Asn Pro Lys Pro Ala Tyr
305                 310                 315                 320

Asn Ala Ile Val Gln Asp Leu Gln Gln
                325

<210> SEQ ID NO 46
<211> LENGTH: 326
<212> TYPE: PRT
<213> ORGANISM: Aspergillus terreus

<400> SEQUENCE: 46

Met Val Arg Leu Thr Val Leu Ala Gly Phe Leu Leu Thr Ser Ala Ala
 1               5                  10                  15

Cys Ser Ala Cys Val Ile Gly Glu Arg Gln Ala Ala Ser Ile Asn
                 20                  25                  30

Asn Ala Phe Lys Ala Lys Gly Lys Lys Tyr Phe Gly Thr Cys Gly Asp
             35                  40                  45

Gln Gly Thr Leu Ser Asp Ser Thr Asn Ser Ala Ile Val Lys Ala Asp
         50                  55                  60

Phe Gly Gln Leu Thr Pro Glu Asn Asn Met Lys Trp Asp Ala Thr Glu
 65                  70                  75                  80

Pro Asn Arg Gly Gln Phe Ser Phe Gly Gly Ala Asp Tyr Leu Val Asn
                     85                  90                  95
```

-continued

```
Tyr Ala Thr Ser Asn Gly Lys Met Ile Arg Gly His Thr Leu Val Trp
            100                 105                 110

His Ser Gln Leu Pro Gly Trp Val Gln Gly Ile Thr Asp Lys Asn Thr
        115                 120                 125

Leu Thr Ser Val Leu Lys Asn His Ile Thr Thr Val Met Gln Arg Tyr
    130                 135                 140

Lys Gly Lys Ile Tyr Ala Trp Asp Val Val Asn Glu Ile Phe Asn Glu
145                 150                 155                 160

Asp Gly Ser Leu Arg Lys Ser Val Phe Tyr Asn Val Leu Gly Glu Asp
                165                 170                 175

Phe Val Arg Ile Ala Phe Glu Thr Ala Arg Ser Val Asp Pro Gln Ala
            180                 185                 190

Lys Leu Tyr Ile Asn Asp Tyr Asn Leu Asp Asn Ala Asn Cys Ala Lys
        195                 200                 205

Thr Lys Gly Met Ala Asp His Val Arg Glu Trp Ile Ser Gln Gly Ile
    210                 215                 220

Pro Ile Asp Gly Ile Gly Ser Gln Thr His Leu Gly Ser Gly Gly Ser
225                 230                 235                 240

Trp Thr Val Lys Asp Ala Leu Asn Thr Leu Ala Ser Ser Gly Val Ser
                245                 250                 255

Glu Val Ala Ile Thr Glu Leu Asp Ile Ala Gly Ala Ser Ser Thr Asp
            260                 265                 270

Tyr Val Asn Val Val Asn Ala Cys Leu Ser Val Ser Lys Cys Val Gly
        275                 280                 285

Ile Thr Val Trp Gly Val Ser Asp Lys Tyr Ser Trp Arg Ser Asn Asp
    290                 295                 300

Lys Pro Leu Leu Phe Asp Ser Asn Phe Gln Pro Lys Ala Ala Tyr Asn
305                 310                 315                 320

Ala Ile Ile Ser Ala Leu
                325

<210> SEQ ID NO 47
<211> LENGTH: 384
<212> TYPE: PRT
<213> ORGANISM: Chrysosporium lucknowense
<400> SEQUENCE: 47

Met Arg Thr Leu Thr Phe Val Leu Ala Ala Ala Pro Val Ala Val Leu
1               5                   10                  15

Ala Gln Ser Pro Leu Trp Gly Gln Cys Gly Gly Gln Gly Trp Thr Gly
            20                  25                  30

Pro Thr Thr Cys Val Ser Gly Ala Val Cys Gln Phe Val Asn Asp Trp
        35                  40                  45

Tyr Ser Gln Cys Val Pro Gly Ser Ser Asn Pro Pro Thr Gly Thr Thr
    50                  55                  60

Ser Ser Thr Thr Gly Ser Thr Pro Ala Pro Thr Gly Gly Gly Gly Ser
65                  70                  75                  80

Gly Thr Gly Leu His Asp Lys Phe Lys Ala Lys Gly Lys Leu Tyr Phe
                85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr His Glu Asn Ser Leu Lys
        115                 120                 125

Trp Asp Ala Thr Glu Pro Ser Arg Asn Gln Phe Asn Phe Ala Asn Ala
```

```
            130                 135                 140
Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
            180                 185                 190

Leu Val Thr Arg Tyr Lys Gly Lys Ile Leu His Trp Asp Val Val Asn
        195                 200                 205

Glu Ile Phe Ala Glu Asp Gly Ser Leu Arg Asp Ser Val Phe Ser Arg
    210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Arg Gly Met Val Glu Lys Val Asn Lys
            260                 265                 270

Trp Ile Ala Gln Gly Ile Pro Ile Asp Gly Ile Gly Thr Gln Cys His
        275                 280                 285

Leu Ala Gly Pro Gly Gly Trp Asn Thr Ala Ala Gly Val Pro Asp Ala
    290                 295                 300

Leu Lys Ala Leu Ala Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
                325                 330                 335

Ala Cys Leu Gln Val Ser Lys Cys Val Gly Ile Thr Val Trp Gly Val
            340                 345                 350

Ser Asp Lys Asp Ser Trp Arg Ser Ser Asn Pro Leu Leu Phe Asp
        355                 360                 365

Ser Asn Tyr Gln Pro Lys Ala Ala Tyr Asn Ala Leu Ile Asn Ala Leu
    370                 375                 380

<210> SEQ ID NO 48
<211> LENGTH: 301
<212> TYPE: PRT
<213> ORGANISM: Thermoascus aurantiacus

<400> SEQUENCE: 48

Ala Ala Ala Gln Ser Val Asp Gln Leu Ile Asp Ala Arg Gly Lys Val
1               5                   10                  15

Tyr Phe Gly Val Ala Thr Asp Gln Asn Arg Leu Thr Thr Gly Lys Asn
                20                  25                  30

Ala Ala Ile Ile Gln Ala Asp Phe Gly Gln Val Thr Pro Glu Asn Ser
            35                  40                  45

Met Lys Trp Asp Ala Thr Glu Pro Ser Gln Gly Asn Phe Asn Phe Ala
        50                  55                  60

Gly Ala Asp Tyr Leu Val Asn Trp Ala Gln Gln Asn Gly Lys Leu Ile
65                  70                  75                  80

Arg Gly His Thr Leu Val Trp His Ser Gln Leu Pro Ser Trp Val Val
                85                  90                  95

Ser Ile Thr Asp Lys Asn Thr Leu Thr Asn Val Met Lys Asn His Ile
            100                 105                 110

Thr Thr Ile Met Thr Arg Tyr Ile Gly Lys Ile Arg Ala Trp Asp Val
        115                 120                 125
```

```
Val Asn Glu Ala Phe Asn Glu Asp Gly Ser Leu Arg Gln Thr Val Phe
    130                 135                 140

Asn Asn Val Ile Gly Glu Asp Tyr Ile Pro Ile Ala Phe Arg Thr Ala
145                 150                 155                 160

Arg Ala Ala Asp Pro Asn Ala Lys Leu Tyr Ile Asn Asp Tyr Asn Leu
                165                 170                 175

Asp Ser Ala Ser Lys Pro Lys Thr Ser Ala Ile Val Lys Arg Val Lys
            180                 185                 190

Lys Trp Arg Ala Ala Gly Val Pro Ile Asp Gly Ile Gly Ser Gln Thr
        195                 200                 205

His Leu Ser Ala Gly Gln Gly Ala Ser Ile Asp Ala Ala Leu Pro Asn
    210                 215                 220

Leu Ala Ser Ala Gly Thr Pro Glu Val Ala Ile Thr Glu Leu Asp Ile
225                 230                 235                 240

Ala Gly Ala Thr Ser Thr Asp Tyr Val Asp Val Asn Ala Cys Leu
                245                 250                 255

Asp Val Asp Ser Cys Ile Gly Ile Thr Val Trp Gly Val Ala Asp Pro
                260                 265                 270

Asp Ser Trp Arg Ala Ser Thr Thr Pro Leu Leu Phe Asp Gly Asn Phe
        275                 280                 285

Asn Pro Lys Pro Ala Tyr Asn Ala Ile Val Gln Leu Leu
290                 295                 300

<210> SEQ ID NO 49
<211> LENGTH: 329
<212> TYPE: PRT
<213> ORGANISM: Colletotrichum higginsianum

<400> SEQUENCE: 49

Met Lys Phe Phe Ser Glu Arg Arg Leu Pro Pro Gly Gly Pro Thr His
1               5                   10                  15

Arg Pro Ser Arg Arg Pro Ser Glu Glu Arg Gln Ala Ser Gln Ser Ile
            20                  25                  30

Asp Arg Leu Ile Lys Ala Lys Gly Lys Gln Tyr Tyr Gly Thr Cys Ser
        35                  40                  45

Asp Gln Gly Arg Leu Thr Ser Gly Arg Asn Ala Asp Ile Ile Lys Ala
    50                  55                  60

Asn Phe Arg Ala Gln Ile Thr Pro Glu Asn Ser Met Lys Trp Asp Gln
65                  70                  75                  80

Ile Glu Pro Ser Arg Gly Gln Phe Asn Trp Ala Gly Pro Asp Tyr Leu
                85                  90                  95

Val Glu Phe Ala Gln Lys Asn Gly Lys Leu Val Arg Gly His Thr Leu
            100                 105                 110

Val Trp His Ser Gln Leu Ala Gly Trp Val Asn Asn Val Arg Asp Arg
        115                 120                 125

Ala Gly Leu Thr Gln Val Ile Glu Ser His Ile Lys Ala Ile Val Gly
    130                 135                 140

Arg Tyr Lys Gly Lys Ile Tyr His Trp Asp Val Val Asn Glu Ile Phe
145                 150                 155                 160

Asn Glu Asp Gly Ser Leu Arg Ser Ser Val Phe Ser Gln Val Leu Gly
                165                 170                 175

Glu Asp Phe Val Gly Ile Ala Phe Arg Ala Ala Arg Ala Ala Asp Pro
            180                 185                 190

Asn Ala Lys Leu Tyr Ile Asn Asp Tyr Asn Leu Asp Gln Ala Ser Tyr
        195                 200                 205
```

Ala Lys Thr Gln Ala Met Ala Arg Lys Val Lys Glu Trp Ile Gly Lys
            210                 215                 220

Gly Ile Pro Ile Tyr Gly Ile Gly Ser Gln Ala His Leu Gln Ala Asn
225                 230                 235                 240

Gln Gly Gly Asn Ala Leu Gly Ala Leu Gln Thr Leu Ala Gly Ser Gly
                245                 250                 255

Val Lys Glu Val Ala Ile Thr Glu Leu Asp Ile Val Gly Ala Ser Thr
            260                 265                 270

Asn Asp Tyr Thr Ala Val Thr Arg Ala Cys Leu Gln Val Pro Gln Cys
        275                 280                 285

Val Gly Ile Thr Val Trp Gly Val Arg Asp Pro Asp Ser Trp Arg Ala
            290                 295                 300

Gln Asn Asn Pro Leu Leu Phe Asp Ala Asn Trp Asn Pro Lys Ala Ala
305                 310                 315                 320

Tyr Asn Ala Val Val Gln Ala Leu Gln
                325

<210> SEQ ID NO 50
<211> LENGTH: 329
<212> TYPE: PRT
<213> ORGANISM: Thermoascus aurantiacus

<400> SEQUENCE: 50

Met Val Arg Pro Thr Ile Leu Leu Thr Ser Leu Leu Leu Ala Pro Phe
1               5                   10                  15

Ala Ala Ala Ser Pro Ile Leu Glu Glu Arg Gln Ala Ala Gln Ser Val
            20                  25                  30

Asp Gln Leu Ile Lys Ala Arg Gly Lys Val Tyr Phe Gly Val Ala Thr
        35                  40                  45

Asp Gln Asn Arg Leu Thr Thr Gly Lys Asn Ala Ala Ile Ile Gln Ala
    50                  55                  60

Asp Phe Gly Gln Val Thr Pro Glu Asn Ser Met Lys Trp Asp Ala Thr
65                  70                  75                  80

Glu Pro Ser Gln Gly Asn Phe Asn Phe Ala Gly Ala Asp Tyr Leu Val
                85                  90                  95

Asn Trp Ala Gln Gln Asn Gly Lys Leu Ile Arg Gly His Thr Leu Val
            100                 105                 110

Trp His Ser Gln Leu Pro Ser Trp Val Ser Ser Ile Thr Asp Lys Asn
        115                 120                 125

Thr Leu Thr Asn Val Met Lys Asn His Ile Thr Thr Leu Met Thr Arg
    130                 135                 140

Tyr Lys Gly Lys Ile Arg Ala Trp Asp Val Val Asn Glu Ala Phe Asn
145                 150                 155                 160

Glu Asp Gly Ser Leu Arg Gln Thr Val Phe Leu Asn Val Ile Gly Glu
                165                 170                 175

Asp Tyr Ile Pro Ile Ala Phe Gln Thr Ala Arg Ala Ala Asp Pro Asn
            180                 185                 190

Ala Lys Leu Tyr Ile Asn Asp Tyr Asn Leu Asp Ser Ala Ser Tyr Pro
        195                 200                 205

Lys Thr Gln Ala Ile Val Asn Arg Val Lys Gln Trp Arg Ala Ala Gly
    210                 215                 220

Val Pro Ile Asp Gly Ile Gly Ser Gln Thr His Leu Ser Ala Gly Gln
225                 230                 235                 240

Gly Ala Gly Val Leu Gln Ala Leu Pro Leu Leu Ala Ser Ala Gly Thr

```
            245                 250                 255
Pro Glu Val Ala Ile Thr Glu Leu Asp Val Ala Gly Ala Ser Pro Thr
            260                 265                 270

Asp Tyr Val Asn Val Val Asn Ala Cys Leu Asn Val Gln Ser Cys Val
            275                 280                 285

Gly Ile Thr Val Trp Gly Val Ala Asp Pro Asp Ser Trp Arg Ala Ser
            290                 295                 300

Thr Thr Pro Leu Leu Phe Asp Gly Asn Phe Asn Pro Lys Pro Ala Tyr
305                 310                 315                 320

Asn Ala Ile Val Gln Asp Leu Gln Gln
                325

<210> SEQ ID NO 51
<211> LENGTH: 327
<212> TYPE: PRT
<213> ORGANISM: Aspergillus aculeatus

<400> SEQUENCE: 51

Met Val Gln Ile Lys Ala Ala Leu Ala Val Leu Phe Ala Ser Asn
1               5                   10                  15

Val Leu Ala Asn Pro Ile Glu Pro Arg Gln Ala Ser Val Ser Ile Asp
            20                  25                  30

Ala Lys Phe Lys Ala His Gly Lys Lys Tyr Leu Gly Thr Ile Gly Asp
            35                  40                  45

Gln Tyr Thr Leu Asn Lys Asn Ala Lys Thr Pro Ala Ile Ile Lys Ala
50                  55                  60

Asp Phe Gly Gln Leu Thr Pro Glu Asn Ser Met Lys Trp Asp Ala Thr
65                  70                  75                  80

Glu Pro Asn Arg Gly Gln Phe Ser Phe Ser Gly Ser Asp Tyr Leu Val
            85                  90                  95

Asn Phe Ala Gln Ser Asn Gly Lys Leu Ile Arg Gly His Thr Leu Val
            100                 105                 110

Trp His Ser Gln Leu Pro Ser Trp Val Gln Ser Ile Tyr Asp Lys Gly
            115                 120                 125

Thr Leu Ile Gln Val Met Gln Asn His Ile Ala Thr Val Met Gln Arg
    130                 135                 140

Tyr Lys Gly Lys Val Tyr Ala Trp Asp Val Val Asn Glu Ile Phe Asn
145                 150                 155                 160

Glu Asp Gly Ser Leu Arg Gln Ser His Phe Tyr Asn Val Ile Gly Glu
            165                 170                 175

Asp Tyr Val Arg Ile Ala Phe Glu Thr Ala Arg Ala Val Asp Pro Asn
            180                 185                 190

Ala Lys Leu Tyr Ile Asn Asp Tyr Asn Leu Asp Ser Ala Ser Tyr Pro
            195                 200                 205

Lys Leu Thr Gly Leu Val Asn His Val Lys Lys Trp Val Ala Ala Gly
    210                 215                 220

Val Pro Ile Asp Gly Ile Gly Ser Gln Thr His Leu Ser Ala Gly Ala
225                 230                 235                 240

Gly Ala Ala Val Ser Gly Ala Leu Asn Ala Leu Ala Gly Ala Gly Thr
            245                 250                 255

Lys Glu Val Ala Ile Thr Glu Leu Asp Ile Ala Gly Ala Ser Ser Thr
            260                 265                 270

Asp Tyr Val Asn Val Val Lys Ala Cys Leu Asn Gln Pro Lys Cys Val
            275                 280                 285
```

```
Gly Ile Thr Val Trp Gly Val Ala Asp Pro Asp Ser Trp Arg Ser Ser
            290                 295                 300

Ser Ser Pro Leu Leu Phe Asp Ser Asn Tyr Asn Pro Lys Ala Ala Tyr
305                 310                 315                 320

Thr Ala Ile Ala Asn Ala Leu
                325

<210> SEQ ID NO 52
<211> LENGTH: 303
<212> TYPE: PRT
<213> ORGANISM: Thermoascus aurantiacus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 52

Xaa Ala Ala Gln Ser Val Asp Gln Leu Ile Lys Ala Arg Gly Lys Val
1               5                   10                  15

Tyr Phe Gly Val Ala Thr Asp Gln Asn Arg Leu Thr Thr Gly Lys Asn
                20                  25                  30

Ala Ala Ile Ile Gln Ala Asn Phe Gly Gln Val Thr Pro Glu Asn Ser
            35                  40                  45

Met Lys Trp Asp Ala Thr Glu Pro Ser Gln Gly Asn Phe Asn Phe Ala
50                  55                  60

Gly Ala Asp Tyr Leu Val Asn Trp Ala Gln Gln Asn Gly Lys Leu Ile
65                  70                  75                  80

Arg Gly His Thr Leu Val Trp His Ser Gln Leu Pro Ser Trp Val Ser
                85                  90                  95

Ser Ile Thr Asp Lys Asn Thr Leu Thr Asn Val Met Lys Asn His Ile
            100                 105                 110

Thr Thr Leu Met Thr Arg Tyr Lys Gly Lys Ile Arg Ala Trp Asp Val
        115                 120                 125

Val Asn Glu Ala Phe Asn Glu Asp Gly Ser Leu Arg Gln Thr Val Phe
130                 135                 140

Leu Asn Val Ile Gly Glu Asp Tyr Ile Pro Ile Ala Phe Gln Thr Ala
145                 150                 155                 160

Arg Ala Ala Asp Pro Asn Ala Lys Leu Tyr Ile Asn Asp Tyr Asn Leu
                165                 170                 175

Asp Ser Ala Ser Tyr Pro Lys Thr Gln Ala Ile Val Asn Arg Val Lys
            180                 185                 190

Lys Trp Arg Ala Ala Gly Val Pro Ile Asp Gly Ile Gly Ser Gln Thr
        195                 200                 205

His Leu Ser Ala Gly Gln Gly Ala Ser Val Leu Gln Ala Leu Pro Leu
210                 215                 220

Leu Ala Ser Ala Gly Thr Pro Glu Val Ala Ile Thr Glu Leu Asp Val
225                 230                 235                 240

Ala Gly Ala Ser Ser Thr Asp Tyr Val Asn Val Val Asn Ala Cys Leu
                245                 250                 255

Asn Val Ser Ser Cys Val Gly Ile Thr Val Trp Gly Val Ala Asp Pro
            260                 265                 270

Asp Ser Trp Arg Ala Ser Thr Thr Pro Leu Leu Phe Asp Gly Asn Phe
        275                 280                 285

Asn Pro Lys Pro Ala Tyr Asn Ala Ile Val Gln Asn Leu Gln Gln
290                 295                 300
```

```
<210> SEQ ID NO 53
<211> LENGTH: 347
<212> TYPE: PRT
<213> ORGANISM: Trichoderma virens

<400> SEQUENCE: 53

Met Lys Ala Asn Val Ile Phe Cys Leu Leu Ala Pro Leu Val Ala Ala
1               5                   10                  15

Leu Pro Thr Glu Phe Ile Gln Leu Glu Pro Asn Leu Ala Ala Arg Arg
            20                  25                  30

Val Asn Ile Thr Glu Arg Met Ala Asp Leu Glu Asp Arg Gln Ala Ser
        35                  40                  45

Val Ser Ile Asp Gln Leu Phe Lys Lys Gly Lys Val Tyr Phe Gly
    50                  55                  60

Thr Ala Thr Asp Arg Gly Leu Leu Gln Arg Glu Arg Asn Ala Ala Ile
65                  70                  75                  80

Ile Gln Ala Asn Phe Gly Gln Val Thr Pro Glu Asn Ser Met Lys Trp
                85                  90                  95

Gln Ser Leu Asn Pro Asn Gln Gly Gln Tyr Asn Trp Ala Asp Ala Asp
            100                 105                 110

Tyr Leu Val Asn Phe Ala Gln Gln Asn Gly Lys Thr Ile Arg Gly His
        115                 120                 125

Thr Leu Val Trp His Ser Gln Leu Pro Ser Trp Val Asn Asn Ile Asn
130                 135                 140

Asn Ala Asp Thr Leu Arg Gln Val Ile Arg Thr His Val Leu Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Glu Ala
        195                 200                 205

Asp Pro Ser Cys Arg Leu Tyr Ile Asn Asp Tyr Asn Leu Asp Arg Ala
    210                 215                 220

Gly Ser Ser Lys Val Asn Leu Met Arg Tyr Tyr Val Asp Lys Trp Ile
225                 230                 235                 240

Ser Gln Gly Val Pro Ile Asp Gly Ile Gly Thr Gln Thr His Leu Ser
                245                 250                 255

Ala Gly Gly Gly Ala Ser Ile Gln Gly Ala Leu Gln Gln Leu Ala Thr
            260                 265                 270

Ala Pro Val Thr Glu Leu Ala Ile Thr Glu Leu Asp Ile Ala Gly Ala
        275                 280                 285

Pro Ser Asn Asp Tyr Asn Ala Val Val Gln Gly Cys Leu Ser Val Ala
    290                 295                 300

Lys Cys Trp Gly Ile Thr Val Trp Gly Ile Ser Asp Lys Asp Ser Trp
305                 310                 315                 320

Arg Gln Gly Thr Asn Pro Leu Leu Phe Asp Ser Asn Phe Asn Pro Lys
                325                 330                 335

Pro Ala Tyr Asn Ser Ile Val Ser Ile Leu Gln
            340                 345

<210> SEQ ID NO 54
<211> LENGTH: 327
<212> TYPE: PRT
<213> ORGANISM: Aspergillus niger
```

<400> SEQUENCE: 54

Met Val Gln Ile Lys Val Ala Ala Leu Ala Met Leu Phe Ala Ser Gln
1               5                   10                  15

Val Leu Ser Glu Pro Ile Glu Pro Arg Gln Ala Ser Val Ser Ile Asp
            20                  25                  30

Thr Lys Phe Lys Ala His Gly Lys Tyr Leu Gly Asn Ile Gly Asp
        35                  40                  45

Gln Tyr Thr Leu Thr Lys Asn Ser Lys Thr Pro Ala Ile Ile Lys Ala
    50                  55                  60

Asp Phe Gly Ala Leu Thr Pro Glu Asn Ser Met Lys Trp Asp Ala Thr
65                  70                  75                  80

Glu Pro Ser Arg Gly Gln Phe Ser Phe Ser Gly Ser Asp Tyr Leu Val
                85                  90                  95

Asn Phe Ala Gln Ser Asn Asn Lys Leu Ile Arg Gly His Thr Leu Val
                100                 105                 110

Trp His Ser Gln Leu Pro Ser Trp Val Gln Ser Ile Thr Asp Lys Asn
            115                 120                 125

Thr Leu Ile Glu Val Met Lys Asn His Ile Thr Thr Val Met Gln His
    130                 135                 140

Tyr Lys Gly Lys Ile Tyr Ala Trp Asp Val Val Asn Glu Ile Phe Asn
145                 150                 155                 160

Glu Asp Gly Ser Leu Arg Asp Ser Val Phe Tyr Lys Val Ile Gly Glu
                165                 170                 175

Asp Tyr Val Arg Ile Ala Phe Glu Thr Ala Arg Ala Ala Asp Pro Asn
                180                 185                 190

Ala Lys Leu Tyr Ile Asn Asp Tyr Asn Leu Asp Ser Ala Ser Tyr Pro
            195                 200                 205

Lys Leu Thr Gly Met Val Ser His Val Lys Lys Trp Ile Ala Ala Gly
    210                 215                 220

Ile Pro Ile Asp Gly Ile Gly Ser Gln Thr His Leu Ser Ala Gly Gly
225                 230                 235                 240

Gly Ala Gly Ile Ser Gly Ala Leu Asn Ala Leu Ala Gly Ala Gly Thr
                245                 250                 255

Lys Glu Ile Ala Val Thr Glu Leu Asp Ile Ala Gly Ala Ser Ser Thr
                260                 265                 270

Asp Tyr Val Glu Val Val Glu Ala Cys Leu Asn Gln Pro Lys Cys Ile
            275                 280                 285

Gly Ile Thr Val Trp Gly Val Ala Asp Pro Asp Ser Trp Arg Ser Ser
    290                 295                 300

Ser Thr Pro Leu Leu Phe Asp Ser Asn Tyr Asn Pro Lys Pro Ala Tyr
305                 310                 315                 320

Thr Ala Ile Ala Asn Ala Leu
                325

<210> SEQ ID NO 55
<211> LENGTH: 327
<212> TYPE: PRT
<213> ORGANISM: Aspergillus niger

<400> SEQUENCE: 55

Met Val Gln Ile Lys Val Ala Ala Leu Ala Met Leu Phe Ala Ser Gln
1               5                   10                  15

Val Leu Ser Glu Pro Ile Asp Pro Arg Gln Ala Ser Val Ser Ile Asp
            20                  25                  30

```
Thr Lys Phe Lys Ala His Gly Lys Lys Tyr Leu Gly Asn Ile Gly Asp
        35              40              45

Gln Tyr Thr Leu Thr Lys Asn Ser Lys Thr Pro Ala Ile Ile Lys Ala
    50              55              60

Asp Phe Gly Ala Leu Thr Pro Glu Asn Ser Met Lys Trp Asp Ala Thr
65              70              75                      80

Glu Pro Ser Arg Gly Gln Phe Ser Phe Ser Gly Ser Asp Tyr Leu Val
            85              90              95

Asn Phe Ala Gln Ser Asn Asn Lys Leu Ile Arg Gly His Thr Leu Val
            100             105             110

Trp His Ser Gln Leu Pro Ser Trp Val Gln Ser Ile Thr Asp Lys Asn
            115             120             125

Thr Leu Ile Glu Val Met Lys Asn His Ile Thr Thr Val Met Gln His
    130             135             140

Tyr Lys Gly Lys Ile Tyr Ala Trp Asp Val Val Asn Glu Ile Phe Asn
145             150             155             160

Glu Asp Gly Ser Leu Arg Asp Ser Val Phe Tyr Lys Val Ile Gly Glu
            165             170             175

Asp Tyr Val Arg Ile Ala Phe Glu Thr Ala Arg Ala Ala Asp Pro Asn
            180             185             190

Ala Lys Leu Tyr Ile Asn Asp Tyr Asn Leu Asp Ser Ala Ser Tyr Ser
    195             200             205

Lys Leu Thr Gly Met Val Ser His Val Lys Lys Trp Ile Ala Ala Gly
    210             215             220

Ile Pro Ile Asp Gly Ile Gly Ser Gln Thr His Leu Ser Ala Gly Gly
225             230             235             240

Gly Ala Gly Ile Ser Gly Ala Leu Asn Ala Leu Ala Gly Ala Gly Thr
            245             250             255

Lys Glu Ile Ala Val Thr Glu Leu Asp Ile Ala Gly Ala Ser Ser Thr
            260             265             270

Asp Tyr Val Glu Val Val Glu Ala Cys Leu Asn Gln Pro Lys Cys Ile
    275             280             285

Gly Ile Thr Val Trp Gly Val Ala Asp Pro Asp Ser Trp Arg Ser Ser
    290             295             300

Ser Thr Pro Leu Leu Phe Asp Ser Asn Tyr Asn Pro Lys Pro Ala Tyr
305             310             315             320

Asp Ala Ile Ala Asn Ala Leu
            325
```

US 10,253,304 B2

COMPOSITION AND METHODS COMPRISING A XYLANASE ENZYME VARIANT

FIELD OF THE INVENTION

The present invention relates to novel xylanases, especially xylanase variants, which are thermostable and the use of said xylanases in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases.

BACKGROUND OF THE INVENTION

Endo-β-1,4-xylanases (EC 3.2.1.8), also referred herein as xylanases, is the name given to a class of enzymes which degrade the linear polysaccharide beta-1,4-xylan into shorter oligomers, and thus breaking down hemicellulose, one of the major components of plant cell walls.

Xylanases have been used for many years in various industrial applications such as in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases.

A common nominator in all these applications is the extreme conditions which faces the enzyme. For example, high temperatures decrease the effective utility of the presently available xylanases under industrial conditions.

In animal feed applications, suitable xylanase enzymes may increase the digestible energy of the biomass in animal feed. The biomass, such as including corn, wheat, and DDGS, used for animal feed comprises two fractions of arabinoxylan, namely the water un-extractable arabinoxylans (WU-AX) and the water extractable arabinoxylans (WE-AX).

Useful xylanases must have not only the capability to degrade WU-AX present in the cell walls and thereby increases the release of encapsulated nutrients, but also have the ability to reduce the digesta viscosity caused by the soluble fraction.

In addition to high bio-efficacy useful xylanases also need good product properties such as pepsin resistance, low pH stability and stability against heat processing.

Pepsin is a digestive protease excreted by the animal in the first part of the digestive system. Pepsin degrades protein which makes the protein available as a nutrient for the animal. The exogenous enzymes, i.e. enzymes added to the feed, are also proteins and they will be degraded if they are susceptible to degradation by the pepsin. This will in most cases destroy the enzyme activity. Thus, useful xylanases are resistant to pepsin degradation.

Stability against feed processing is also an important feature of a xylanase in order to be useful as a feed additive. During preparation the xylanase faces high temperature conditions for a short time (e.g. 30 sec at 90° C.) during feed processing (pelleting). However, the actual catalytic activity of the enzyme is needed at lower temperatures (e.g. ~37° C.). Consequently, the enzyme should not be inactivated irreversibly at high temperatures, while it has to be active at relative lower temperatures.

Accordingly, the need exists for xylanase enzymes that have high bio-efficacy and good product properties, including being stable against heat processing.

The parent xylanase of the present invention is superior for solubilisation of wheat and corn fiber, both water-unextractable arabinoxylans (WU-AX) and the water extractable arabinoxylans (WE-AX). In addition to that the parent xylanase has excellent biochemical properties relevant for e.g. feed production and feed application. The variants of the present invention are all derived from such a parent xylanase and were selected by specifically looking for amino acid positions which when substituted will improve the thermostability of said variant, while keeping the inherited biochemical properties unchanged.

BRIEF DESCRIPTION OF THE FIGURES

FIG. 5 shows a nucleotide sequence (SEQ ID NO:1) encoding a xylanase referred to herein as FveXyn4;

FIG. 6 shows a polypeptide sequence (SEQ ID NO:2) of a xylanase referred to herein as FveXyn4, without signal peptid. This is the active form of the enzyme. This may be referred to herein as the mature form of the enzyme. In some embodiments this sequence may be a backbone or parent sequence;

FIG. 7 shows a nucleotide sequence (SEQ ID NO:3) encoding a xylanase referred to herein as FoxXyn2;

FIG. 8 shows a polypeptide sequence (SEQ ID NO:4) of a xylanase referred to herein as FoxXyn2. This is another active form of the enzyme. In some embodiments, this may be referred to herein as the mature form of the enzyme. In some embodiments this sequence is a backbone or parent sequence.

FIG. 9 shows the nucleotide sequence (SEQ ID NO:5) of the genomic fragment coding for FveXyn4 xylanase;

FIG. 10 shows the coding cDNA sequence (SEQ ID NO:6) of FveXyn4 xylanase;

FIG. 11 shows the polypeptide sequence of the FveXyn4 protein (SEQ ID NO: 7) produced from *T. reesei* strain deleted for major cellulases and xylanase 2 (Δcbh1 Δcbh2 Δegl1 Δegl2 Δegl3 Δegl4 Δegl5 Δegl6 Δbgl1 Δman1 Δxyn2 pyr2-) (signal sequence is underlined);

FIG. 12 shows a polypeptide sequence (SEQ ID NO:8) of a xylanase of the present invention (FveXyn4). Underlined (lower case) portion of the sequence reflects an N terminal signal peptide which can be cleaved before the enzyme is matured;

FIG. 13 shows a polypeptide sequence (SEQ ID NO:9) of a xylanase of the present invention (FveXyn4). The amino acids shown in bold and italicized may also be cleaved by post-translational modification before the enzyme is fully matured. In some embodiments this sequence may be the backbone or parent sequence;

FIG. 14 shows a nucleotide sequence (SEQ ID NO:10) encoding a xylanase of the present invention (FveXyn4). The lower case nucleotides which are in bold show the intron sequence. The sequence shown bold (uppercase) encodes the sequence that may be cleaved off before maturation of the enzyme;

FIG. 15 shows a nucleotide sequence (SEQ ID NO:11) encoding a xylanase of the present invention (FveXyn4). The sequence shown bold (uppercase) encodes the sequence that may be cleaved off before maturation of the enzyme;

FIG. 16 shows a polypeptide sequence (SEQ ID NO:12) of a xylanase of the present invention (FoxXyn2). Underlined (lower case) portion of the sequence may reflect an N terminal signal peptide which can be cleaved before the enzyme is matured. The amino acids shown in bold and italicized may also be cleaved by post-translational modification before the enzyme is fully matured. In some embodiments this sequence is a backbone or parent sequence;

FIG. 17 shows a polypeptide sequence (SEQ ID NO:13) of a xylanase of the present invention (FoxXyn2). The amino acids shown in bold and italicized may also be cleaved by post-translational modification before the enzyme is fully matured. This sequence may be an active form of the protein. This may be referred to herein as the mature form of the enzyme. In some embodiments this sequence is a backbone or parent sequence;

FIG. 18 shows a nucleotide sequence (SEQ ID NO:14) encoding a xylanase of the present invention (FoxXyn2). The lower case nucleotides which are in bold show the intron sequence. The sequence shown bold (uppercase) encodes the sequence that may be cleaved off before maturation of the enzyme;

FIG. 19 shows shows a nucleotide sequence (SEQ ID NO:15) encoding a xylanase of the present invention (FoxXyn2). The sequence shown bold (uppercase) encodes the sequence that may be cleaved off before maturation of the enzyme;

FIG. 20 shows a polypeptide sequence (SEQ ID NO:16) of a xylanase from *Fusarium*—*Fusarium* Comparative Sequencing Project, Broad Institute of Harvard and MIT In some embodiments, this sequence is a backbone sequence;

FIG. 21 shows a nucleotide sequence (SEQ ID NO:17) encoding a xylanase for use in the present invention from *Fusarium*—obtained from *Fusarium* Comparative Sequencing Project, Broad Institute of Harvard and MIT. The lower case nucleotides which are in bold show the intron sequence. The sequence, which is shown bold (upper case), encodes the sequence that may be cleaved off before maturation of the enzyme. Changes compared with SEQ ID NO:10 are underlined;

FIG. 22 shows a nucleotide sequence (SEQ ID NO:18) encoding a xylanase for use in the present invention from *Fusarium*—obtained from *Fusarium* Comparative Sequencing Project, Broad Institute of Harvard and MIT. The sequence, which is shown bold (upper case), encodes the sequence that may be cleaved off before maturation of the enzyme. Changes compared with SEQ ID No. 11 are underlined;

FIG. 23 shows a nucleotide sequence (SEQ ID NO:19) encoding a xylanase for use in the present invention from *Fusarium*—obtained from *Fusarium* Comparative Sequencing Project, Broad Institute of Harvard and MIT. Changes compared with SEQ ID No. 1 are underlined.

SUMMARY OF THE INVENTION

Figure 1:
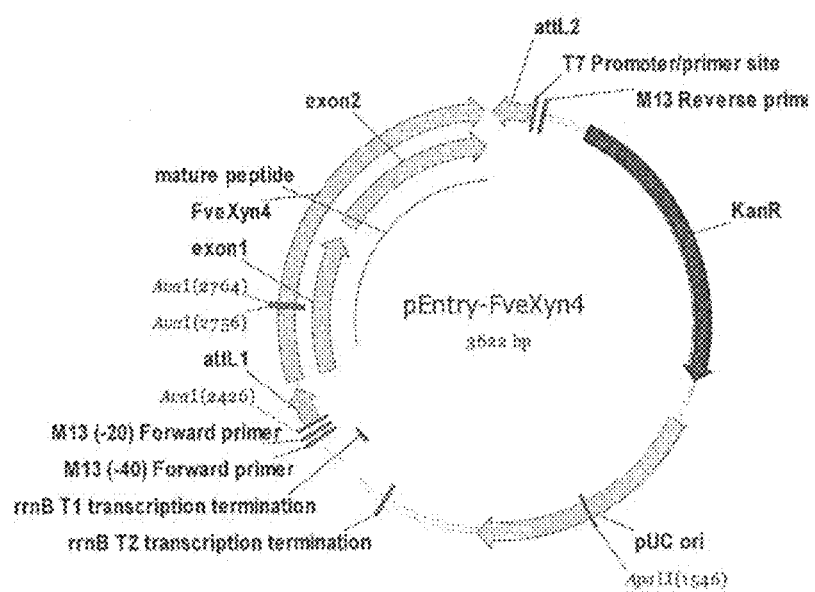
FIG. 1 shows a schematic map of pEntry-FveXyn4.
Figure 2:
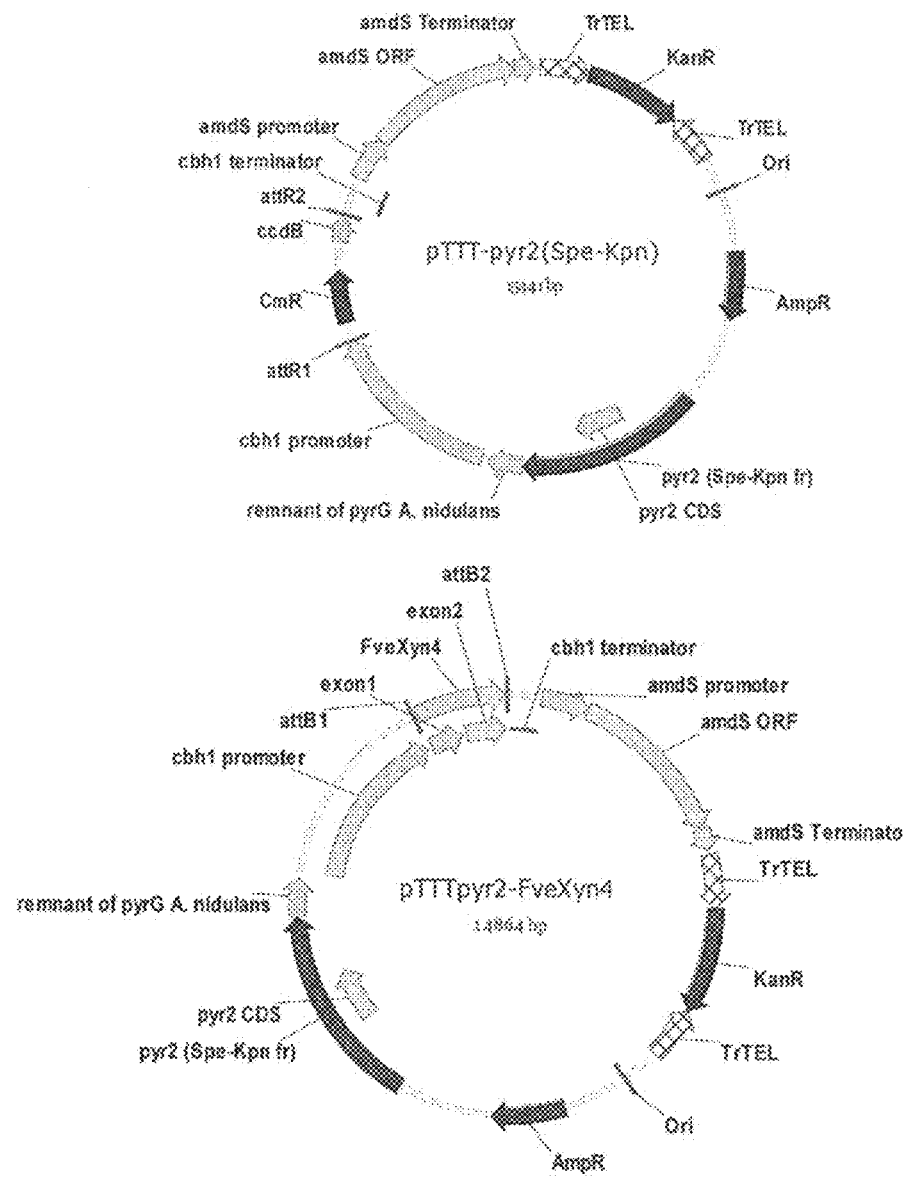
FIG. 2 show schematic maps of the destination pTTTpyr2 and expression pTTTpyr2-FveXyn4 vectors.

The present invention provides improved xylanase variant enzymes. Specifically, the present invention provides xylanase variants having one or more modifications, such as substitutions, as compared to a parent xylanase enzyme. Overall, these modifications results in xylanase enzymes having improved thermostability compared to the xylanase parent from which they are derived.

The present invention is based on the surprising finding that the most valuable mutations or substitutions in amino acid positions are not the ones that improve a single important property of the enzyme, such as e.g. improved thermostability, but rather modifications or substitution in amino acid positions that improve an important property of the enzyme and at the same time don't have a negative influence on other properties. These modifications or substitutions can be used to make superior combinatorial variants. Thus, the common feature for all xylanase variants of the present invention is that they have a substitution in an amino acid position and none of these substitutions in such positions significantly decrease expression, activity and stability of the enzyme compared to the parent enzyme, but improves at least one important property, such as increase thermostability, compared to the parent enzyme. This set of substitutions is beneficial for generating variants with several substitutions to obtain variants with highly increase performance.

Accordingly, the invention provides variants of GH10 xylanase enzymes having one or more modifications compared to their parent GH10 xylanase enzyme. The xylanase variants can be useful in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry.

Additionally, the invention provides amino acid positions in a xylanase enzyme, where favourable modifications result in a minimum performing index for specific activity, pepsin resistance and expression while having the thermostability improved compared to a parent xylanase enzyme. These modifications are considered suitable modifications of the invention. These amino acid positions can be considered useful positions for combinatorial modifications to a parent xylanase enzyme and will in the following be referred to as productive positions. Such productive positions can be further characterized by having multiple modifications that render the xylanase suitable for use in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry. For each position, greater numbers of possible suitable modifications denotes a higher productivity of a particular position.

In addition, the xylanase variants of the present invention are particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol), a (fast) reduction in viscosity is obtained or the solubilized polymers (obtained from dissolving AXinsol) cannot contribute to increasing viscosity.

Without wishing to be bound by theory, the xylanase variants of the present invention mainly release polymers, which do not contribute to viscosity, because the released polymers are short.

Typically, conventional xylanases may breakdown AXinsol, but will often lead to an increase in viscosity of the mixture. This increased viscosity is disadvantageous in many applications.

Without wishing to be bound by theory, although some conventional xylanases breakdown AXinsol, they lead to an increase in soluble degradation products of high molecular weight, which leads to an increase in viscosity in the mixture.

Furthermore or alternatively and again without wishing to be bound by theory, conventional xylanase enzymes may breakdown AXinsol, but because they do not degrade the solubilised products of high molecular weight fast enough the viscosity in the mixture is not ideal. In contrast, with the methods and uses of the present invention, the xylanase variant breakdown AXinsol without increasing viscosity and/or whilst reducing viscosity quickly compared with conventional enzymes. Without wishing to be being bound by theory, it is believed that high molecular weight products are not formed by the enzymes of the present invention.

The xylanase variants of the present invention and as described herein have been found to not only breakdown (solubilise) insoluble arabinoxylans (AXinsol) from a wide range of substrates, including corn, wheat, DDGS, etc, in particular corn and corn-based substrates, in particular both wheat (including wheat-based) products and corn (including corn-based products), but also efficiently ensuring that viscosity is not raised and/or reducing viscosity. Without wishing to be being bound by theory, it is believed that high molecular weight products are not formed by the enzymes of the present invention.

Thus the present invention relates to xylanase variants capable of solubilising pentosans, in particular xylan-containing materials, such as arabinoxylans, in particular insoluble arabinoxylans. In particular the enzyme is particularly good at solubilising pentosans in particular xylan-containing materials, such as arabinoxylans, in particular insoluble arabinoxylans, in a broad spectrum of substrates, including corn based substrates.

The present invention further relates to xylanase variants capable of degrading AXsol or the breakdown products of AXinsol to ensure viscosity is not increased and/or is reduced in the reaction mixture.

Many of the xylanases commercialized for use in feedstuffs for solubilizing pentosans are GH11 enzymes. It had been considered by those skilled in the art that GH10 xylanases were not as strong at solublizing pentosans, particularly AXinsol, compared with GH11 xylanases. Surprisingly it has been found that the novel xylanase variants disclosed herein which is a GH10 xylanase is particularly good at degrading AXinsol in a broad spectrum of substrates, including corn based substrates. Surprisingly, the present inventors have found that the variant GH10 xylanases of the present invention outperform commercial GH11 xylanases in their ability to solubilize pentosans. In addition the variant GH10 xylanases are thermostable.

The fact that the present enzymes efficiently degrade AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-based diet, such as corn-soy diet for example.

It was completely unexpected for a GH10 xylanase to be so good at degrading AXinsol in cereals, particularly in corn or corn-based substrates.

The enzymes of the present invention are able to efficiently (and quickly) degrade the polymers and oligomers that are produced from degradation of AXinsol or that are present in grain-based material. This leads to an unexpected advantage for the GH10 xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g. bio-based isoprene); or in the wheat gluten-starch separation industry for the production of starch for example.

Notably it has been found that the degradation product on average is shorter for the GH10 enzymes tested herein compared with GH11 enzymes. This means that the degradation products do not contribute to or cause an increase in viscosity.

Based on these findings, the xylanase variant according to the present invention can be used to degrade a xylan-containing material, particularly arabinoxylans, particularly AXinsol. In addition or alternatively, the xylanases according to the present invention can be used to degrade soluble polymers (e.g. oligomers) that are produced from degradation of AXinsol or that are (naturally) present in grain-based materials. Surprisingly it has been found that the xylanase variant according the present invention can be used to both degrade a xylan-containing material, particularly arabinoxylans, particularly AXinsol, and to degrade soluble polymers (e.g. oligomers) that are produced from degradation of AXinsol.

Such enzymes finds useful application in many industries, including feedstuffs, malting and brewing, in the treatment of arabinoxylan containing raw materials like grain-based materials, herein grain-based materials includes grains and cereals, in the wheat gluten-starch separation industry, in the production of starch derived syrups, in biofuel production, and the like.

Statements of the Invention

A first aspect of the present invention provides a xylanase polypeptide variant which comprises a substitution at a productive amino acid position compared to a parent GH10 xylanase, wherein said substitution increases the thermostability of the polypeptide without significantly reducing the specific activity, pepsin resistance and expression of the polypeptide, and wherein at least 2 out of 20 possible amino acid substitutions at the productive position makes the xylanase variant able to meet at least one of the following criteria:

a. Relative performance (Performance Index, PI) for specific activity in at least one of the two activity assays I and II is greater than 0.8, PI for pepsin resistance is greater than 0.9, PI for expression (unstressed activity assay 1) is greater than 0.057, and PI for thermostability assay 1 is greater than 1.2 or PI for thermostability assay 2 is greater than 1.5;

b. Relative performance (Performance Index, PI) for specific activity in at least one of the two activity assays I and II is greater than 0.5, PI for pepsin resistance is greater than 0.8, PI for expression (unstressed activity assay 1) is greater than 0.057, and PI for Thermostability assay 1 is greater than 1.2 or PI for thermostability assay 2 is greater than 1.3; or c. Relative performance (Performance Index, PI) for specific activity in at least one of the two activity assays I and II is greater than 0.9, PI for pepsin resistance is greater than 0.9, PI for expression (unstressed activity assay 1) is greater than 0.057, and PI for Thermostability assay 1 is greater than 1.0 or PI for thermostability assay 2 is greater than 1.0;

wherein the productive position is selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, and wherein the polypeptide set forth in SEQ ID NO:2 is used for numbering.

In another aspect, the present invention provides a nucleic acid molecule (e.g. an isolated or recombinant nucleic acid molecule) encoding a thermostable xylanase and comprising (or consisting of) a backbone polynucleotide sequence comprising a nucleotide sequence selected from the group consisting of:

a) a nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or b) a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or c) a nucleotide sequence which can hybridize to SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18 under high stringency conditions;

which backbone polynucleotide sequence is modified at, at least one codon encoding an amino acid at a position selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, wherein the polypeptide set forth in SEQ ID NO:2 is used for numbering.

In a yet further aspect, the present invention provides a vector (e.g. a plasmid) or constructs comprising (or consisting of) a backbone polynucleotide sequence comprising a nucleotide sequence selected from the group consisting of:

a) a nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or b) a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or c) a nucleotide sequence which can hybridize to SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18 under high stringency conditions;

which backbone polynucleotide sequence is modified at, at least one codon encoding an amino acid at a position selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, wherein the polypeptide set forth in SEQ ID NO:2 is used for numbering.

The present invention yet further provides a host cell comprising the nucleic acid according to the invention or a vector or construct according to the invention.

The present invention also relates to a method of producing a xylanase variant, comprising:

a. modifying (e.g. transforming) a host cell with a nucleic acid molecule according to the invention, or a vector or construct (e.g. DNA construct) according to the invention, or with a DNA construct comprising a promoter having transcriptional activity in the host cell operably linked with a heterologous polynucleotide sequence according to the invention, or with a DNA construct comprising a promoter having transcriptional activity in the host cell operably linked with a heterologous polynucleotide sequence encoding a xylanase variant according to the invention;

b. cultivating the modified (e.g. transformed) host cell in a suitable culture medium to allow expression of the xylanase.

A further aspect relates to a fermentate and a xylanase produced by the method of the invention.

In a further aspect of the present invention there is provided an enzyme composition comprising a xylanase variant enzyme according to the invention or the fermentate according to the invention or the xylanase according to the invention.

A yet further aspect of the present invention is the provision of a feed additive composition comprising a xylanase variant enzyme according to the invention or the fermentate according to the invention or the xylanase according to the invention.

The present invention yet further provides a premix comprising a xylanase variant enzyme according to the invention, or the fermentate according to the invention, or the xylanase according to the invention, or the enzyme composition according to the invention, or a feed additive composition according to the invention, and at least one vitamin and/or at least one mineral.

The present invention further provides a feed (or feedstuff) comprising a xylanase variant enzyme according to the invention, or the fermentate according to the invention, or the xylanase according to the invention, or the enzyme composition according to the invention, or a feed additive composition according to the invention, or a premix according to the invention.

The present invention yet further provides a method of preparing a feedstuff comprising admixing a feed component with a xylanase variant enzyme according to the invention, or the fermentate according to the invention, or the xylanase according to the invention, or the enzyme composition according to the invention, or a feed additive composition according to the invention, or a premix according to the invention.

A further aspect relates to a method for degrading arabinoxylan-containing material in a xylan-containing material, comprising admixing said xylan-containing material with a xylanase variant enzyme according to the invention, or the fermentate according to the invention, or the xylanase according to the invention, or the enzyme composition according to the invention, or a feed additive composition according to the invention, or a premix according to the invention.

Another aspect relates to the use of a xylanase variant enzyme according to the invention, or the fermentate according to the invention, or the xylanase according to the invention, or the enzyme composition according to the invention, or a feed additive composition according to the invention, or a premix according to the invention for solubilizing arabinoxylan in a xylan-containing material.

In a further aspect there is provided a fermented beverage, e.g. beer, produced by a method according to the invention.

A final aspect relates to xylanase variants, polypeptides, nucleic acids, vectors, host cells, methods, uses and kits as generally described herein with reference to the Figures and Examples.

DETAIL DISCLOSURE OF THE INVENTION

General Definitions

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

In the present invention, a specific numbering of amino acid residue positions in the xylanases used in the present invention may be employed. By alignment of the amino acid sequence of a sample xylanases with the xylanase of the present invention (particularly SEQ ID NO: 2) it is possible to allot a number to an amino acid residue position in said sample xylanase which corresponds with the amino acid residue position or numbering of the amino acid sequence shown in SEQ ID NO: 2 of the present invention.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The term "consisting essentially of" as used herein means that unspecified components may be present if the characteristics of the claimed composition are thereby not materially affected.

The term "consisting of" means that the proportions of the specific ingredients must total 100%.

The term "comprising" used herein may be amended in some embodiments to refer to consisting essentially of or consisting of (both having a more limited meaning that "comprising").

The publications discussed herein are provided solely for their disclosure prior to the filing date of the present application. Nothing herein is to be construed as an admission that such publications constitute prior art to the claims appended hereto.

Increasing prices of raw material traditionally used as energy source in animal feed, as a feedstock in biofuel production, as an ingredient in brewing or malting, or as a feedstock in wheat gluten-starch separation processes for instance have resulted in inclusion of low-cost fibrous materials in the starting substrates for these industries, particularly the use of low-cost fibrous by-products in animal feed.

Fibre addition may cause several disadvantageous effects. For example in animal feed fibre addition may cause anti-nutritional effects. The presence of un-degraded polymers present in the animal's intestine causes a highly viscous content and impeded diffusion with reduced nutrient absorption as a result. Also, the polymers possess a high water holding capacity hindering an effective re-absorption of water, and the water retention increases the volume of the gut content, which leads to a decrease intestinal transit time (Englyst & Kingman (1993) in Human Nutrition and Dietetics, 9th edition (Garrow J. S., James W. P. T., eds.) p. 53).

In feedstuffs, hemicellulose and cellulose (including insoluble arabinoxylan) also form physical barriers encapsulating (or entrapping) nutrients like starch and protein and thereby retaining access to these nutrients for the animal.

Hemicellulose and cellulose (including insoluble arabinoxylans (AXinsol)) by themselves are also potential energy sources, as they consist of C5- and C6-saccharides. Mono C6-saccharides can be used as energy source by the animal, while oligo C5-saccharides can be transformed into short chain fatty acids by the micro flora present in the animal gut (van den Broek et al., 2008 Molecular Nutrition & Food Research, 52, 146-63), which short chain fatty acids can be taken up and digested by the animal's gut.

Release of nutrients and water from feedstuffs as a consequence of physical barrier degradation is dependent on the ability of the xylanase to degrade insoluble fibre components (e.g. insoluble arabanoxylans (AXinsol)).

Xylanase Enzymes of the Invention

As used herein, the xylanase enzyme includes an enzyme, a polypeptide or a protein exhibiting a xylan degrading capability such as a capability of degrading a linear polysaccharide beta-1,4-xylan into xylooligosaccharides or xylose, thus breaking down hemicellulose, one of the major components of plant cell walls.

As discussed above, the xylanase of the present invention is preferably a GH10 xylanase. In other words the xylanase may have a molecular weight in the range of 32-39 kDa and/or the catalytic domain of the xylanase consists of an eightfold β/α barrel structure (as taught in Harris et al 1996—Acta. Crystallog. Sec. D 52, 393-401).

In one aspect of the invention, the xylanase of the invention is a xylanase of Glycoside Hydrolase (GH) Family 10. The term "of Glycoside Hydrolase (GH) Family 10" means that the xylanase in question is or can be classified in the GH family 10.

Protein similarity searches (e.g. protein blast at http://blast.ncbi.nlm.nih.gov/Blast.cgi?CMD=Web&PAGE_TYPE=BlastHome) may determine whether an unknown sequence falls under the term of a GH10 xylanase family member, particularly the GH families may be categorised based on sequence homology in key regions. In addition or alternatively, to determine whether an unknown protein sequence is a xylanase protein within the GH10 family, the evaluation can be done, not only on sequence similarity/homology/identity, but also on 3D structure similarity. The classification of GH-families is often based on the 3D fold. Software that will predict the 3D fold of an unknown protein sequence is HHpred (http://toolkit.tuebingen.mpg.de/hhpred). The power of this software for protein structure prediction relies on identifying homologous sequences with known structure to be used as template. This works so well because structures diverge much more slowly than primary sequences. Proteins of the same family may have very similar structures even when their sequences have diverged beyond recognition.

In practice, an unknown sequence can be pasted into the software (http://toolkit.tuebingen.mpg.de/hhpred) in FASTA format. Having done this, the search can be submitted. The output of the search will show a list of sequences with known 3D structures. To confirm that the unknown sequence indeed is a GH10 xylanase, GH10 xylanases may be found within the list of homologues having a probability of >90. Not all proteins identified as homologues will be characterised as GH10 xylanases, but some will. The latter proteins are proteins with a known structure and biochemically characterisation identifying them as xylanases. The former have not been biochemically characterised as GH10 xylanases. Several references describes this protocol such as Söding J. (2005) Protein homology detection by HMM-HMM comparison—Bioinformatics 21, 951-960 (doi: 10.1093/bioinformatics/bti125) and Söding J, Biegert A, and Lupas A N. (2005) The HHpred interactive server for protein homology detection and structure prediction—Nucleic Acids Research 33, W244-W248 (Web Server issue) (doi: 10.1093/nar/gki40).

According to the Cazy site (http://www.cazy.org/), Family 10 glycoside hydrolases can be characterised as follows:

Known Activities: endo-1,4-β-xylanase (EC 3.2.1.8); endo-1,3-β-xylanase (EC 3.2.1.32); tomatinase (EC 3.2.1.-)

Mechanism: Retaining

Clan: GH-A

Catalytic Nucleophile/Base: Glu (experimental)

Catalytic Proton Donor: Glu (experimental)

3D Structure Status: $(\beta/\alpha)_8$

The GH10 xylanase of the present invention may have a catalytic domain with molecular weights in the range of 32-39 kDa. The structure of the catalytic domain of the GH10 xylanase of the present invention consists of an eightfold (β/α barrel (Harris et al 1996—Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously *Pseudomonas fluorescens* subsp. xylanase A) (Harris et al Structure 1994 Nov. 15; 2(11) 1107-16.). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al Proc Natl Acad Sci USA 1995 Jul. 18; 92(15) 7090-4).

The term "GH10 xylanase" as used herein means a polypeptide having xylanase activity and having a $(\alpha/\beta)_8$ TIM barrel fold with the two key active site glutamic acids located at the C-terminal ends of beta-strands 4 (acid/base) and 7 (nucleophile).

Productive Positions of Xylanase Enzymes

The invention provide amino acid positions in a xylanase enzyme, where favourable modifications result in a minimum performing index for specific activity, pepsin resistance and expression while having the thermostability improved compared to a parent xylanase enzyme. These position are referred herein as "Productive positions" and can further be described as those positions within a molecule that are most useful for making combinatorial variants exhibiting an improved characteristic, where the position itself allows for at least one combinable mutation. Thus, productive positions according to the present invention are positions which have shown a certain degree of tolerance for multiple substitutions, while at the same time meeting a set of criteria for combinability as describe below. These modifications are considered suitable modifications of the invention.

"Combinable mutations" or "combinable substitutions" are defined as the mutations or substitutions in a molecule that can be used to make combinatorial variants. Combinable mutations are those that improve at least one desired property of the molecule, without significantly reducing or decreasing other properties of the enzyme such as expression, activity and stability. In the present context, the expression "without significantly reducing or decreasing other properties of the enzyme such as expression, activity, and stability" means that the performance index for the specific activity in at least one of the two activity assays I and II (described below) is greater than 0.5, preferably greater than 0.8, more preferably greater than 0.9, the performance index for pepsin resistance (described below) is greater than 0.8, preferably greater than 0.9, and performance index for expression, expressed as unstressed activity assay 1 (described below), is greater than 0.057.

Accordingly, the present invention provides productive amino acid positions in a GH10 xylanase enzyme, which when modified, makes the xylanase variant able to be useful in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, where favourable modification results in an increased thermostability compared to the parent GH10 xylanase enzyme. These modifications are considered suitable modifications of the invention.

The terms "parent" and "backbone" are used interchangeably, and means a xylanase, preferably a GH10 xylanase, to which an alteration is made to produce a variant enzyme of the present invention. In one embodiment the parent enzyme is a GH10 xylanase. In further embodiments, the parent is selected from the group consisting of SEQ ID NO:2, SEQ ID NO:4, SEQ ID NO:16, SEQ ID NO:7, SEQ ID NO:8, SEQ ID NO:9, SEQ ID NO:12, and SEQ ID NO:13. Suitably the parent enzyme may be a naturally occurring (wild-type) polypeptide or a variant or fragment thereof. In a preferred embodiment the parent enzyme is a naturally occurring (wild-type polypeptide).

The thermostability of the xylanase variant of the invention can be compared to the stability of a standard, for example, the GH10 xylanase isolated from *Fusarium verticilloides* having the polypeptide sequence shown in SEQ ID NO:2.

The term "thermostability" is the ability of an enzyme to resist irreversible inactivation (usually by denaturation) at a relatively high temperature. This means that the enzyme retains a specified amount of enzymatic activity after exposure to an identified temperature over a given period of time.

There are many ways of measuring thermostabiliy. By way of example, enzyme samples maybe incubated without substrate for a defined period of time (e.g. 10 min or 1 to 30 min) at an elevated temperature compared to the temperature at which the enzyme is stable for a longer time (days). Following the incubation at elevated temperature the enzyme sample is assayed for residual activity at the permissive temperature of e.g. 30° C. (alternatively 25-50° C. or even up to 70° C.). Residual activity is calculated as relative to a sample of the enzyme that has not been incubated at the elevated temperature.

Thermostability can also be measured as enzyme inactivation as function of temperature. Here enzyme samples are incubated without substrate for a defined period of time (e.g. 10 min or 1 to 30 min) at various temperatures and following incubation assayed for residual activity at the permissive temperature of e.g. 30° C. (alternatively 25-70° C. or even higher). Residual activity at each temperature is calculated as relative to a sample of the enzyme that has not been incubated at the elevated temperature. The resulting thermal denaturation profile (temperature versus residual activity) can be used to calculate the temperature at which 50% residual activity is obtained. This value is defined as the Tm value.

Even further, thermostability can be measured as enzyme inactivation as function of time. Here enzyme samples are incubated without substrate at a defined elevated temperature (e.g. 76° C.) for various time periods (e.g. between 10 sec and 30 min) and following incubation assayed for residual activity at the permissive temperature of e.g. 30° C. (alternatively 25-70° C. or even higher). Residual activity at each temperature is calculated as relative to an enzyme sample that has not been incubated at the elevated temperature. The resulting inactivation profile (time versus residual activity) can be used to calculate the time at which 50% residual activity is obtained. This is usually given as T½.

These are examples of how to measure thermostability. Thermostability can also be measured by other methods. Preferably thermostability is assessed by use of the "Assay for measurement of thermostability" as taught herein.

In contradistinction to thermostability, thermoactivity is enzyme activity as a function of temperature. To determine thermoactivity enzyme samples may be incubated (assayed) for the period of time defined by the assay at various temperatures in the presence of substrate. Enzyme activity is obtained during or immediately after incubation as defined by the assay (e.g. reading an OD-value which reflects the amount of formed reaction product). The temperature at which the highest activity is obtained is the temperature optimum of the enzyme at the given assay conditions. The activity obtained at each temperature can be calculated relative to the activity obtained at optimum temperature. This will provide a temperature profile for the enzyme at the given assay conditions.

In the present application thermostability is not the same as thermoactivity.

In some embodiments, the xylanase of the present invention retain at least about 50%, about 60%, about 70%, about 75%, about 80%, about 85%, about 90%, about 92%, about 95%, about 96%, about 97%, about 98%, or about 99% activity after exposure to altered temperatures over a given time period, for example, at least about 60 sec, about 120 sec, about 180 sec, about 240 sec, about 300 sec, etc.

Combinable mutations in a xylanase enzyme can be determined using relative performance index (PI) values resulting from the assays described below under "Screening assays": Thermostability I, Thermostability II, Specific activity I, Specific activity II, Pepsin Resistance and protein expression being defined by a minimum of activity in Activity assay I.

Combinable mutations can be grouped according to the following criteria (A-G):

A. Performance index (PI) relative to xylanase parent for specific activity in at least one of the two activity assays I and II is greater than 0.8, PI for Pepsin resistance is greater than 0.9, and PI for Thermostability assay 1 is greater than 1.2. In addition, PI for Activity assay 1 is greater than 0.057 (Group A);

B. Performance index (PI) relative to xylanase parent for specific activity in at least one of the two activity assays I and II is greater than 0.5, PI for Pepsin resistance is greater than 0.8, and PI for Thermostability assay 1 is greater than 1.2. In addition, PI for Activity assay 1 is greater than 0.057 (Group B);

C. Performance index (PI) relative to xylanase parent for specific activity in at least one of the two activity assays I and II is greater than 0.9, PI for Pepsin resistance is greater than 0.9, and PI for Thermostability assay 1 is greater than 1.0. In addition, PI for Activity assay 1 is greater than 0.057 (Group C);

D. Performance index (PI) relative to xylanase parent for specific activity in at least one of the two activity assays I and II is greater than 0.8, PI for Pepsin resistance is greater than 0.9, and PI for Thermostability assay 2 is greater than 1.5. In addition, PI for Activity assay 1 is greater than 0.057 (Group D);

E. Performance index (PI) relative to xylanase parent for specific activity in at least one of the two activity assays I and II is greater than 0.5, PI for Pepsin resistance is greater than 0.8, and PI for Thermostability assay 2 is greater than 1.5. In addition, PI for Activity assay 1 is greater than 0.057 (Group E);

F. Performance index (PI) relative to xylanase parent for specific activity in at least one of the two activity assays I and II is greater than 0.5, PI for Pepsin resistance is greater than 0.8, and PI for Thermostability assay 2 is greater than 1.3. In addition, PI for Activity assay 1 is greater than 0.057 (Group F), or G. Performance index (PI) relative to xylanase parent for specific activity in at least one of the two activity assays I and II is greater than 0.9, PI for Pepsin resistance is greater than 0.9, and PI for Thermostability assay 2 is greater than 1.0. In addition, PI for Activity assay 1 is greater than 0.057 (Group G).

Xylanase enzyme amino acid positions found to be a useful or a productive position can have different modifications that render or make the enzyme suitable for use in various applications as mentioned above. Modifications can include an insertion, deletion or substitution at the particular position. In one embodiment, a modification is a substitution.

For each position, greater numbers of possible suitable modifications results in a higher productivity score for the position as shown in the Examples below. For example, an amino acid position can have at least 2 out of 20, at least 4 out of 20, or at least 8 out of 20 of the possible modifications (i.e. the 20 standard amino acids involved in translation) tested at a productive position as suitable modifications or substitutions, wherein the modification or substitution makes the xylanase variant able to meet at least one of the following suitability criteria:

a. Relative performance (Performance Index, PI) for specific activity in at least one of the two activity assays I and II is greater than 0.8, PI for pepsin resistance is greater than 0.9, PI for expression (unstressed activity assay 1) is greater than 0.057, and PI for thermostability assay 1 is greater than 1.2 or PI for thermostability assay 2 is greater than 1.5;

b. Relative performance (Performance Index, PI) for specific activity in at least one of the two activity assays I and II is greater than 0.5, PI for pepsin resistance is greater than 0.8, PI for expression (unstressed activity assay 1) is greater than 0.057, and PI for Thermostability assay 1 is greater than 1.2 or PI for thermostability assay 2 is greater than 1.3; or c. Relative performance (Performance Index, PI) for specific activity in at least one of the two activity assays I and II is greater than 0.9, PI for pepsin resistance is greater than 0.9, PI for expression (unstressed activity assay 1) is greater than 0.057, and PI for Thermostability assay 1 is greater than 1.0 or PI for thermostability assay 2 is greater than 1.0.

Thus, the combinable mutations that fall within the above groups A, B, C, D, E, F or G will make the variant able to meet the above criteria a) to c).

The Productive positions are assigned a "Productivity Score" based on the number of amino acid substitutions at a given position that fall within the groups A, B, C, D, E, F, or G using the criteria for determination of Productivity Score set forth below. Thus, in the present context, the term "productivity score" means suitability of a position for modifications that will improve certain properties of the enzyme.

The criteria to determine the Productivity Score for productive positions are as follows:

Positions where at least 15 out of 20 possible substitutions at a given position fall within the above groups A, B, C, D, E, F or G are given a Productivity Score of "4". (Below Table 2.1)

Productive Positions where less than 15, but at least 8 out of 20 possible substitutions at a given position fall within above groups A, B, C, D, E, F or G are given a Productivity Score of "3". (Below Table 2.2)

Productive Positions where less than 8, but at least 4 out of 20 possible substitutions at a given position fall within above groups A, B, C, D, E, F or G are given a Productivity Score of "2". (Below Table 2.3)

Productive Positions where less than 4, but at least 2 out of 20 possible substitutions at a given position fall within above groups A, B, C, D, E, F or G are given a Productivity Score of "1". (Below Table 2.4)

In one embodiment of the present invention at least 2 out of 20 possible amino acid substitutions at the productive position makes the xylanase variant able to meet at least one of the criteria a) to c), and wherein the productive position is selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, wherein the polypeptide set forth in SEQ ID NO:2 is used for numbering.

In one embodiment of the present invention at least 4 out of 20 possible amino acid substitutions at the productive position makes the xylanase variant able to meet at least one of the criteria a) to c), and wherein the productive position is selected from the group consisting of 135, 28, 57, 62, 70, 79, 89, 102, 105, 118, 151, 153, 160, 181, 184, 200, 220, 232, 262 and 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230 and 233, and wherein the polypeptide set forth in SEQ ID NO:2 is used for numbering.

In one embodiment of the present invention at least 8 out of 20 possible amino acid substitutions at the productive position makes the xylanase variant able to meet at least one of the criteria a) to c), wherein the productive position is selected from the group consisting of 135, 28, 57, 62, 70, 79, 89, 102, 105, 118, 151, 153, 160, 181, 184, 200, 220, 232, 262 and 298, and wherein the polypeptide set forth in SEQ ID NO:2 is used for numbering.

In a specific embodiment of the present invention, the xylanase variant is one where the productive position is position 135, and wherein the polypeptide set forth in SEQ ID NO:2 is used for numbering.

These amino acid positions can be considered useful positions for combinatorial modifications to a parent xylanase enzyme. Thus, the invention includes xylanase enzymes having one or more modifications at any of the above positions.

In one embodiment, the xylanase variant comprises or consists of a substitution at a position corresponding to position 7. In another embodiment, the amino acid at a position corresponding to position 7 is substituted with Asp. In another embodiment, the variant comprises or consists of the substitution 7D of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 25. In another embodiment, the amino acid at a position corresponding to position 25 is substituted with Pro. In another embodiment, the variant comprises or consists of the substitution 25D of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 33. In another embodiment, the amino acid at a position corresponding to position 33 is substituted with Val. In another embodiment, the variant comprises or consists of the substitution 33V of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 57. In another embodiment, the amino acid at a position corresponding to position 57 is substituted with Gln. In another embodiment, the amino acid at a position corresponding to position 57 is substituted with Thr. In another embodiment, the amino acid at a position corresponding to position 57 is substituted with Val. In another embodiment, the variant comprises or consists of the substitution 57Q of the mature polypeptide of SEQ ID NO:2. In another embodiment, the variant comprises or consists of the substitution 57T of the mature polypeptide of SEQ ID NO:2. In another embodiment, the variant comprises or consists of the substitution 57V of the mature polypeptide of SEQ ID NO:2. In another embodiment, the amino acid at a position corresponding to position 57 is substituted with Gln, Gln or Val of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 62. In another embodiment, the amino acid at a position corresponding to position 62 is substituted with Ser. In another embodiment, the amino acid at a position corresponding to position 62 is substituted with Thr. In another embodiment, the variant comprises or consists of the substitution 62S of the mature polypeptide of SEQ ID NO:2. In another embodiment, the variant comprises or consists of the substitution 62T of the mature polypeptide of SEQ ID NO:2. In another embodiment, the amino acid at a position corresponding to position 62 is substituted with Ser, or Thr of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 79. In another embodiment, the amino acid at a position corresponding to position 79 is substituted with Phe. In another embodiment, the amino acid at a position corresponding to position 79 is substituted with Val. In another embodiment, the amino acid at a position corresponding to position 79 is substituted with Tyr. In another embodiment, the amino acid at a position corresponding to position 79 is substituted with Ile. In another embodiment, the amino acid at a position corresponding to position 79 is substituted with Leu. In another embodiment, the amino acid at a position corresponding to position 79 is substituted with Met. In another embodiment, the variant comprises or consists of the substitution 79F of the mature polypeptide of SEQ ID NO:2. In another embodiment, the variant comprises or consists of the substitution 79V of the mature polypeptide of SEQ ID NO:2. In another embodiment, the variant comprises or consists of the substitution 79Y of the mature polypeptide of SEQ ID NO:2. In another embodiment, the variant comprises or consists of the substitution 79I of the mature polypeptide of SEQ ID NO:2. In another embodiment, the variant comprises or consists of the substitution 79L of the mature polypeptide of SEQ ID NO:2. In another embodiment, the variant comprises or consists of the substitution 79M of the mature polypeptide of SEQ ID NO:2. In another embodiment, the amino acid at a position corresponding to position 79 is substituted with Phe, Val, Tyr, Ile, Leu or Met of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 89. In another embodiment, the amino acid at a position corresponding to position 89 is substituted with Gly. In another embodiment, the amino acid at a position corresponding to position 89 is substituted with Asn. In another embodiment, the amino acid at a position corresponding to position 89 is substituted with Gln. In another embodiment, the amino acid at a position corresponding to position 89 is substituted with Leu. In another embodiment, the amino acid at a position corresponding to position 89 is substituted with Met. In another embodiment, the variant comprises or consists of the substitution 89G of the mature polypeptide of SEQ ID NO:2. In another embodiment, the variant comprises or consists of the substitution 89N of the mature polypeptide of SEQ ID NO:2. In another embodiment, the variant comprises or consists of the substitution 89Q of the mature polypeptide of SEQ ID NO:2. In another embodiment, the variant comprises or consists of the substitution 89L of the mature polypeptide of SEQ ID NO:2. In another embodiment, the variant comprises or consists of the substitution 89M of the mature polypeptide of SEQ ID NO:2. In another embodiment, the amino acid at a position corresponding to position 89 is substituted with Gly, Asn, Gln, Leu, or Met of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 103. In another embodiment, the amino acid at a position corresponding to position 103 is substituted with Met. In another embodiment, the amino acid at a position corresponding to position 103 is substituted with Lys. In another embodiment, the variant comprises or consists of the substitution 103M of the mature polypeptide of SEQ ID NO:2. In another embodiment, the variant comprises or consists of the substitution 103K of the mature polypeptide of SEQ ID NO:2. In another embodiment, the amino acid at a position corresponding to position 103 is substituted with Met or Lys of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 115. In another embodiment, the amino acid at a position corresponding to position 115 is substituted with Glu. In another embodiment, the amino acid at a position corresponding to position 115 is substituted with Leu. In another embodiment, the variant comprises or consists of the substitution 115E of the mature polypeptide of SEQ ID NO:2. In another embodiment, the variant comprises or consists of the substitution 115L of the mature polypeptide of SEQ ID NO:2. In another embodiment, the amino acid at a position corresponding to position 115 is substituted with Glu or Leu of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 147. In another embodiment, the amino acid at a position corresponding to position 147 is substituted with Gln. In another embodiment, the variant comprises or consists of the substitution 147Q of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 181. In another embodiment, the amino acid at a position corresponding to position 181 is substituted with Ala. In another embodiment, the amino acid at a position corresponding to position 181 is substituted with Asp. In another embodiment, the amino acid at a position corresponding to position 181 is substituted with Pro. In another embodiment, the amino acid at a position corresponding to position 181 is substituted with Gln. In another embodiment, the variant comprises or consists of the substitution 181A of the mature polypeptide of SEQ ID NO:2. In another embodiment, the variant comprises or consists of the substitution 181D of the mature polypeptide of SEQ ID NO:2. In another embodiment, the variant comprises or consists of the substitution 181P of the mature polypeptide of SEQ ID NO:2. In another embodiment, the variant comprises or consists of the substitution 181Q of the mature polypeptide of SEQ ID NO:2. In another embodiment, the amino acid at a position corresponding to position 181 is substituted with Ala, Asp, Pro, or Gln of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 193. In another embodiment, the amino acid at a position corresponding to position 193 is substituted with Tyr. In another embodiment, the amino acid at a position corresponding to position 193 is substituted with Asn. In another embodiment, the variant comprises or consists of the substitution 193Y of the mature polypeptide of SEQ ID NO:2. In another embodiment, the variant comprises or consists of the substitution 193N of the mature polypeptide of SEQ ID NO:2. In another embodiment, the amino acid at a position corresponding to position 193 is substituted with Tyr or Asn of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 217. In another embodiment, the amino acid at a position corresponding to position 217 is substituted with Glu. In another embodiment, the amino acid at a position corresponding to position 217 is substituted with Pro. In another embodiment, the amino acid at a position corresponding to position 217 is substituted with Gln. In another embodiment, the amino acid at a position corresponding to position 217 is substituted with Asp. In another embodiment, the amino acid at a position corresponding to position 217 is substituted with Met. In another embodiment, the variant comprises or consists of the substitution 217E of the mature polypeptide of SEQ ID NO:2. In another embodiment, the variant comprises or consists of the substitution 217P of the mature polypeptide of SEQ ID NO:2. In another embodiment, the variant comprises or consists of the substitution 217Q of the mature polypeptide of SEQ ID NO:2. In another embodiment, the variant comprises or consists of the substitution 217D of the mature polypeptide of SEQ ID NO:2. In another embodiment, the variant comprises or consists of the substitution 217M of the mature polypeptide of SEQ ID NO:2. In another embodiment, the amino acid at a position corresponding to position 217 is substituted with Glu, Pro, Gln, Asp, or Met of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 219. In another embodiment, the amino acid at a position corresponding to position 219 is substituted with Asp. In another embodiment, the amino acid at a position corresponding to position 219 is substituted with Pro. In another embodiment, the variant comprises or consists of the substitution 219D of the mature polypeptide of SEQ ID NO:2. In another embodiment, the variant comprises or consists of the substitution 219P of the mature polypeptide of SEQ ID NO:2. In another embodiment, the amino acid at a position corresponding to position 219 is substituted with Asp or Pro of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

In one embodiment, the xylanase variant comprises or consists of a substitution at a position corresponding to position 298. In another embodiment, the amino acid at a position corresponding to position 298 is substituted with Phe. In another embodiment, the amino acid at a position corresponding to position 298 is substituted with Trp. In another embodiment, the amino acid at a position corresponding to position 298 is substituted with Tyr. In another embodiment, the variant comprises or consists of the substitution 298F of the mature polypeptide of SEQ ID NO:2. In another embodiment, the variant comprises or consists of the substitution 298W of the mature polypeptide of SEQ ID NO:2. In another embodiment, the variant comprises or consists of the substitution 298Y of the mature polypeptide of SEQ ID NO:2. In another embodiment, the amino acid at a position corresponding to position 298 is substituted with Phe, Trp, or Tyr of the polypeptide of SEQ ID NO:2 or of a polypeptide having at least 70% identity (suitably at least 80%, suitably at least 90%, suitably at least 95%, suitably at least 98%, suitably at least 99% identity) with SEQ ID NO:2.

Suitable Modifications of the Xylanase Enzymes

The invention includes enzyme variants of xylanase enzymes having one or more modifications compared to a parent xylanase enzyme, such as a GH10 xylanase parent. The enzyme variants can be useful in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases.

In one embodiment the substitution at the productive position makes the xylanase variant able to have a relative performance (Performance Index, PI) for specific activity in at least one of the two activity assays I and II which is greater than 0.5, a PI for pepsin resistance which is greater than 0.8, a PI for expression (unstressed activity assay 1) which is greater than 0.057, and a PI for thermostability assay 1 which is greater than 1.2 or PI for thermostability assay 2 is greater than 1.5, wherein said substitution is selected from the group consisting of N007D, K011Q, I021A, I021T, I021C, N025P, G028M, A030P, D032P, T033V, N062T, N062F, G064S, G064T, S065G, S065M, V070N, V070E, V070Q, V070S, F072L, Q074R, Q074E, K079I, K079L, K079F, K079V, K079Y, K079M, S089G, S089Q, S089L, S089M, N099Y, D100V, A102K, A102V, T103K, L104V, L104I, T105K, T105F, V107A, V107T, E109Q, V112T, V112L, T113R, T113K, T113N, V115E, V115L, R118F, K120P, V129A, I132P, I132A, E134D, E134G, W135P, W135Q, W135T, W135D, W135N, W135S, W135R, W135E, W135K, W135C, W135G, W135A, W135M, W135L, D136C, L139Q, D142L, D142V, F149M, G150W, G150Y, N151K, N151M, N151H, N151V, D152N, D152Q, D152P, D152W, D153S, D153I, D153T, V155T, V155A, G156W, F159M, A161V, R163M, R163V, G181A, S193N, S199K, T211C, T211H, A217P, A217Q, A217E, A217M, G219P, Q220K, I221V, A227K, A229T, A229N, A229D, S231P, G232K, G232M, G232L, V233T, E235Q, R244K, N260Q, A296F, T298F, T298W, T298Y, and V300P, and wherein the polypeptide set forth in SEQ ID NO:2 is used for numbering.

In one embodiment the substitution at the productive position makes the xylanase variant able to have a relative performance (Performance Index, PI) for specific activity in at least one of the two activity assays 1 and II is greater than 0.5, PI for pepsin resistance is greater than 0.8, PI for expression (unstressed activity assay 1) is greater than 0.057, and PI for thermostability assay 1 is greater than 1.2 and PI for thermostability assay 2 is greater than 1.3, where said substitution is selected from the group consisting of N007D, I021C, N025P, G028M, A030P, D032P, T033V, S065G, F072L, K079I, K079L, K079F, K079V, K079Y, S089G, S089Q, V115E, I132P, W135T, W135D, W135E, D142L, T211C, T211H, A217P, A217Q, A217E, G219P, I221V, V233T, T298F, T298W, and T298Y, and wherein the polypeptide set forth in SEQ ID NO:2 is used for numbering.

In one embodiment the substitution at the productive position makes the xylanase variant able to have a relative performance (Performance Index, PI) for specific activity in at least one of the two activity assays I and II is greater than 0.9, PI for pepsin resistance is greater than 0.9, PI for expression (unstressed activity assay 1) is greater than 0.057, and PI for thermostability assay 1 is greater than 1.0 and PI for thermostability assay 2 is greater than 1.0, wherein said substitution is selected from the group consisting of N007D, N007D, K011Q, I021T, I021V, N025P, G028S, G028Q, D032P, K037L, S057Q, S057V, S057T, G059S, N062T, N062S, G064T, S065N, N071D, F072L, Q074R, Q075E, G077Q, K079F, K079V, S089N, I098V, A102D, T103M, V107T, E109Q, T113Q, V115E, V115L, V115Q, R118K, I132A, W135D, W135G, W135Y, W135I, L139Q, N147Q, D153S, V155A, S180E, G181P, G181D, G181Q, G181A, A183F, S184L, S184I, M190V, S193Y, L198Q, L198M, S199T, S199I, Q200K, Q200T, V202E, A217P, A217Q, A217E, A217M, A217D, G219P, G219D, Q220K, Q220A, G232Q, V233T, P262N, P262T, G266A, A296F, T298F, T298W, T298Y, and V300P, and wherein the polypeptide set forth in SEQ ID NO:2 is used for numbering.

In one embodiment the substitution at the productive position makes the xylanase variant able to have a relative performance (Performance Index, PI) for specific activity in at least one of the two activity assays I and II is greater than 0.8, PI for Pepsin resistance is greater than 0.9, PI for expression (unstressed activity assay 1) is greater than 0.057, and PI for thermostability assay 1 is greater than 1.2 and PI for thermostability assay 2 is greater than 1.5, wherein said substitution is selected from the group consisting of N007D, I021C, N025P, G028M, A030P, D032P, S065G, K079F, K079V, K079Y, S089G, I132P, W135E, T211C, T211H, A217P, A217Q, A217E, T298F, T298W, and T298Y, and wherein the polypeptide set forth in SEQ ID NO:2 is used for numbering.

In one embodiment the substitution at the productive position makes the xylanase variant able to have a relative performance (Performance Index, PI) for specific activity in at least one of the two activity assays I and II is greater than 0.9, PI for pepsin resistance is greater than 0.9, PI for expression (unstressed activity assay 1) is greater than 0.057, and PI for Thermostability assay 1 is greater than 1.2 and PI for thermostability assay 2 is greater than 1.5, wherein said substitution is selected from the group consisting of N007D, N025P, D032P, K079F, K079V, A217P, A217Q, A217E, T298F, T298W, and T298Y, and wherein the polypeptide set forth in SEQ ID NO:2 is used for numbering.

Xylanase Parent of the Xylanase Variant

As described above, the parent of the xylanase variant may be a GH10 xylanase. Suitably, the parent GH10 xylanase may be obtainable (suitably obtained) from a *Fusarium* organism.

In one embodiment the xylanase variant has a backbone or a parent amino acid sequence (before modification) which comprises (or consists of) an amino acid sequence selected from the group consisting of SEQ ID NO:2, SEQ ID NO:4, SEQ ID NO:16, SEQ ID NO:7, SEQ ID NO:8, SEQ ID NO:9, SEQ ID NO:12, or SEQ ID NO:13; or an amino acid sequence having at least 70% identity (suitably at least 80%, suitably at least 90%, suitably at least 95%, suitably at least 98%, suitably at least 99% identity) with SEQ ID NO:2, SEQ ID NO:4, SEQ ID NO:16, SEQ ID NO:7, SEQ ID NO:8, SEQ ID NO:9, SEQ ID NO:12, or SEQ ID NO:13; or an amino acid sequence encoded by a nucleotide sequence comprising the nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or an amino acid sequence encoded by a nucleotide sequence comprising a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or an amino acid sequence encoded by a nucleotide sequence which can hybridize to SEQ ID NO:1, SEQ ID NO:3, SEQ ID NO:6, SEQ ID NO:19, SEQ ID NO:10, SEQ ID NO:11, SEQ ID NO:14, SEQ ID NO:15, SEQ ID NO:17, or SEQ ID NO:18 under high stringency conditions.

In one embodiment the backbone or parent GH10 xylanase (before modification) is:
- a. a xylanase comprising an amino acid sequence selected from the group consisting of SEQ ID NO:2, SEQ ID NO:4, SEQ ID NO:16, SEQ ID NO:7, SEQ ID NO:8, SEQ ID NO:9, SEQ ID NO:12, or SEQ ID NO:13; or
- b. a xylanase enzyme comprising an amino acid sequence having at least 70% identity (suitably at least 80%, suitably at least 90%, suitably at least 95%, suitably at least 98%, suitably at least 99% identity) with SEQ ID NO:2, SEQ ID NO:4, SEQ ID NO:16, SEQ ID NO:7, SEQ ID NO:8, SEQ ID NO:9, SEQ ID NO:12, or SEQ ID NO:13; or
- c. a xylanase enzyme encoded by a nucleotide sequence comprising the nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
- d. a xylanase enzyme encoded by a nucleotide sequence comprising a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
- e. a xylanase enzyme encoded by a nucleotide sequence which can hybridize to SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18 under high stringency conditions.

In one embodiment the parent or backbone amino acid sequence has at least 80% identity with SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

In one embodiment the parent or backbone amino acid sequence has at least 80% identity with SEQ ID NO:2.

In one embodiment the parent or backbone amino acid sequence has at least 90% identity with SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

In one embodiment the parent or backbone amino acid sequence has at least 90% identity with SEQ ID NO:2.

In one embodiment the parent or backbone amino acid sequence has at least 95% identity with SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

In one embodiment the parent or backbone amino acid sequence has at least 95% identity with SEQ ID NO:2.

In one embodiment the parent or backbone amino acid sequence has at least 98% identity with SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

In one embodiment the parent or backbone amino acid sequence has at least 98% identity with SEQ ID NO:2.

In one embodiment the backbone or parent xylanase enzyme may be encoded by a nucleotide sequence comprising a nucleotide sequence having at least 80% identity with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18.

In one embodiment the backbone or parent xylanase enzyme may be encoded by a nucleotide sequence comprising a nucleotide sequence having at least 80% identity with SEQ ID NO:1.

In one embodiment the backbone or parent xylanase enzyme may be encoded by a nucleotide sequence comprising a nucleotide sequence having at least 90% identity with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18.

In one embodiment the backbone or parent xylanase enzyme may be encoded by a nucleotide sequence comprising a nucleotide sequence having at least 90% identity with SEQ ID NO:1.

In one embodiment the backbone or parent xylanase enzyme may be encoded by a nucleotide sequence comprising a nucleotide sequence having at least 95% identity with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18.

In one embodiment the backbone or parent xylanase enzyme may be encoded by a nucleotide sequence comprising a nucleotide sequence having at least 95% identity with SEQ ID NO:1.

In one embodiment the backbone or parent xylanase enzyme may be encoded by a nucleotide sequence comprising a nucleotide sequence having at least 98% identity with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18.

In one embodiment the backbone or parent xylanase enzyme may be encoded by a nucleotide sequence comprising a nucleotide sequence having at least 98% identity with SEQ ID NO:1.

Suitably, the parent or backbone GH10 xylanase may be obtainable (suitably obtained) from a *Fusarium* organism.

In one embodiment the parent or backbone amino acid sequence has the sequence shown in SEQ ID NO:2.

In one embodiment the backbone or parent xylanase enzyme may be encoded by a nucleotide sequence comprising a nucleotide sequence shown in SEQ ID NO:1.

The xylanase variant according to the present invention is preferably an endo-1,4-β-xylanase.

One embodiment of the invention relates to a nucleotide sequence encoding a xylanase variant according to the invention.

A further embodiment relates to a nucleic acid molecule (e.g. an isolated or recombinant nucleic acid molecule) encoding a thermostable xylanase and comprising (or consisting of) a backbone polynucleotide sequence comprising a nucleotide sequence selected from the group consisting of:
 a. a nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
 b. a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
 c. a nucleotide sequence which can hybridize to SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18 under high stringency conditions;

which backbone polynucleotide sequence is modified at, at least one codon encoding an amino acid at a position selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, wherein the polypeptide set forth in SEQ ID NO:2 is used for numbering.

Further Embodiments of the Present Invention

An embodiment of the invention relates to a vector (e.g. a plasmid) or construct comprising (or consisting of) a backbone polynucleotide sequence comprising a nucleotide sequence selected from the group consisting of:
 a) a nucleotide sequence shown herein as SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
 b) a nucleotide sequence having at least 70% identity (suitably at least 80%, suitably at least 90%, suitably at least 95%, suitably at least 98%, suitably at least 99% identity) with SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18; or
 c) a nucleotide sequence which can hybridize to SEQ ID NO:1 or SEQ ID NO:2 under high stringency conditions;

which backbone polynucleotide sequence is modified at, at least one codon encoding an amino acid at a position selected from the group consisting of 135, 28, 57, 62, 70, 79, 89, 102, 105, 118, 151, 153, 160, 181, 184, 200, 220, 232, 262, 298, 4, 21, 25, 30, 56, 59, 64, 65, 71, 74, 77, 98, 99, 100, 103, 104, 106, 113, 115, 117, 120, 134, 141, 142, 148, 150, 152, 156, 161, 163, 167, 176, 180, 193, 198, 199, 201, 202, 215, 217, 227, 229, 230, 233, 3, 6, 7, 11, 12, 16, 18, 29, 32, 33, 37, 38, 52, 53, 58, 67, 72, 75, 92, 93, 94, 96, 97, 107, 109, 110, 112, 114, 116, 125, 129, 132, 133, 136, 138, 139, 146, 147, 149, 155, 159, 162, 164, 168, 169, 182, 183, 188, 190, 191, 194, 196, 206, 209, 211, 219, 221, 231, 235, 236, 238, 244, 249, 260, 266, 268, 269, 274, 296, 300, 302 and 304, wherein the polypeptide set forth in SEQ ID NO:2 is used for numbering.

The host cell of the present invention may be selected from the group consisting of a bacterial cell, fungal cell, a yeast cell, a filamentous fungal cell and a plant cell. Preferably the host cell is a bacterial or fungal cell. Suitable host cells are described later.

In one preferred embodiment the xylanase variant produced in accordance with a method of the present invention is recovered.

In one preferred embodiment the xylanase variant produced in accordance with a method of the present invention is isolated and/or purified.

In some embodiments the xylanase variant may be used directly as a fermentate without isolation and/or purification of the enzyme.

In some embodiments the feed additive composition according to the present invention or the premix according to the present invention further comprises one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

The xylanase variant according to the present invention may be used in a method for degrading arabinoxylan-containing material in a xylan-containing material.

Suitably, the arabinoxylan may be insoluble arabinoxylan (AXinsol).

In one embodiment the xylan-containing material is selected from one or more of the group consisting of: a feed or feedstuff; a feed component; a grain-based material; a mash; a wort; a malt; malted barely; an adjunct, a barley mash; and a cereal flour.

In a preferred embodiment the arabinoxylans are solubilized without increasing viscosity in the reaction medium.

In one embodiment of the present invention the feed or feedstuff or feed component comprises or consists of corn, DDGS (such as cDDGS), wheat, wheat bran or a combination thereof.

In one preferred embodiment the feed or feedstuff is a corn-based feedstuff.

The xylanase variant according to the resent invention may be used in combination with one or more of the enzymes selected from the group consisting: endoglucanases (E.C. 3.2.1.4); celliobiohydrolases (E.C. 3.2.1.91), β-glucosidases (E.C. 3.2.1.21), cellulases (E.C. 3.2.1.74), lichenases (E.C. 3.1.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), amylases, alpha-amylases (E.C. 3.2.1.1), other xylanases (E.C. 3.2.1.8, E.C. 3.2.1.32, E.C. 3.2.1.37, E.C. 3.1.1.72, E.C. 3.1.1.73), glucoamylases (E.C. 3.2.1.3), hemicellulases, proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)), debranching enzymes, cutinases, esterases and/or mannanases (e.g. a β-mannanase (E.C. 3.2.1.78)).

The xylanase variant according to the resent invention may be used in combination with one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

In one embodiment the method or use according to the present invention comprises administering a subject with a xylanase variant enzyme according to the present invention, or a fermentate comprising a xylanase variant enzyme according to the present invention, or an enzyme composition comprising a xylanase variant enzyme according to the present invention, or a feed additive composition comprising a xylanase variant enzyme according to the present invention, or a premix comprising a xylanase variant enzyme according to the present invention or a feedstuff comprising a xylanase variant enzyme according to the present invention.

In one embodiment the method or use of the present invention is (or is part of) a wheat gluten-starch separation process.

In another embodiment, the method or use of the present invention is (or is part of) a biofuel (e.g. bioethanol) or biochemical (e.g. bio-based isoprene) production process.

In another embodiment, the method or use of the present invention is (or is part of) a malting or brewing process.

Suitably, a fermented beverage, e.g. beer, produced by a method according to the present invention in envisaged by the present invention.

In one embodiment the parent xylanase enzyme of the present invention may be referred to herein as FveXyn4 or SEQ ID No.2.

Both the polypeptide sequences and the nucleic acid sequences taught herein are preferably isolated.

The xylanase of the present invention is preferably a GH10 xylanase as defined above The backbone (or parent) xylanase enzyme used herein may be referred to as FveXyn4 (SEQ ID NO:2) or FoxXyn 2 (SEQ ID NO:4) (these terms refer to the active proteins, e.g. the mature proteins).

In one embodiment preferably the xylanase is a fungal xylanase.

In one embodiment, the xylanase variant and/or parent enzyme is a GH10 xylanase.

In one embodiment preferably the xylanase variant (and/or parent xylanase) is a fungal GH10 xylanase.

In one embodiment preferably the xylanase variant (and/or parent xylanase) is an endoxylanase, e.g. an endo-1,4-β-d-xylanase. The classification for an endo-1,4-β-d-xylanase is E.C. 3.2.1.8.

Preferably the xylanase variant of the present invention has an optimum pH at about 6. Preferably the enzyme having xylanase activity retains greater than 70% of maximum activity between pH4 and 8, suitably between pH 4.6 and 7. In some embodiments, e.g. in feed applications, the enzyme having xylanase activity retains greater than 70% of maximum activity between between 5.1 and 7.

Without wishing to be bound by theory, pH may also have an important effect on enzyme efficacy and efficiency. For feed applications in particular the pH profile of the xylanases of the present invention favour activity in the small intestine, under neutral conditions.

In one embodiment, the xylanase variant according to the present invention is capable of degrading (or degrades) a xylan-containing material, particularly arabinoxylans, particularly insoluble arabinoxylans (AXinsol).

In another embodiment the xylanase variant according to the present invention is capable of degrading (or degrades) soluble polymers (e.g. oligomers) that are produced from degradation of AXinsol or that are (naturally) present in grain-based material.

In a further embodiment the xylanase variant is capable of degrading (or degrades) both a xylan-containing material, particularly arabinoxylans, particularly AXinsol, and soluble polymers (e.g. oligomers) that are produced from degradation of AXinsol.

In one embodiment the xylanase variants of the present invention are unaffected by wheat xylanases inhibitors, e.g. proteinaceous inhibitors, e.g. TAXI-like proteinaceous inhibitors in wheat. Prior art fungal xylanases can be inhibited by as much as 70-95% by wheat proteinaceous inhibitors. Preferably the xylanases of the present invention are only inhibited by 20-30% at most in wheat applications.

TAXI are *Triticum aestivum* xylanases inhibitors, present in cereals.

In one embodiment the insoluble arabinoxylan containing material is not wheat straw.

The term "fragment thereof" as used herein means an active fragment. In other words the fragment is one which has xylanase activity. Suitably the fragment may have the same xylanase activity as the full length GH10 xylanase variant enzyme from which the fragment is derived. Alternatively, the fragment may have a modified activity (e.g. enhanced specificity, specific activity, pH or temperature profile) compared with the full length modified GH10 xylanase enzyme from which the fragment is derived. In addition the fragment must retain the thermostable properties of the GH10 variant xylanase enzyme of which it is a fragment.

In one embodiment the fragment is at least 60% of the full length of the GH10 xylanase variant enzyme from which the fragment is derived.

In one embodiment the fragment is at least 75% of the full length of the GH10 xylanase variant enzyme from which the fragment is derived.

In one embodiment the fragment is at least 85% of the full length of the GH10 xylanase variant enzyme from which the fragment is derived.

In one embodiment the fragment is at least 95% of the full length of the GH10 xylanase variant enzyme from which the fragment is derived.

In one embodiment the fragment is at least 98% of the full length of the GH10 xylanase variant enzyme from which the fragment is derived.

The term "variant xylanase(s)" as used herein may be used interchangeably with "modified xylanase(s)" and relates to a polypeptide having xylanase activity comprising a substitution at one, or one or more (e.g., several) positions compared to the parent polypeptide. The term "modifying" as used herein means changing or altering. Furthermore, the term "modifying" as used herein means altering from the naturally occurring. In other words, when modifying the enzyme, one changes the enzyme in such as way that renders the enzyme altered from the parent backbone enzyme. Preferably the variant does not exist itself in nature. Thus the variant enzyme is a non-naturally-occurring enzyme.

The term "modified" as used herein means altered, e.g. from its naturally occurring form. The modified or variant enzymes according to the present are preferably not naturally occurring enzymes or naturally occurring enzymes. In other words, the variant enzymes according to the present invention are preferably modified enzymes that have not been found in nature. The modified enzymes or variant enzymes of the present invention have preferably not occurred spontaneously.

Uses

The xylanase variant of the present invention can be suitably used in any one of the following applications:

a) An additive in animal feedstuffs; and/or b) A feed supplement for an animal; and/or c) Breakdown of grain-based material (e.g. this can be whole grain or part of grain). The breakdown products (e.g. glucose) can be used as a feedstock for any fermentation process, such as in biofuel (e.g. bioethanol) production or in the production of other products such as biochemicals (e.g., bio-based isoprene). Therefore in one embodiment the present invention relates to the production of biofuel (e.g. bioethanol) and to the enhanced utilisation of grain-based material in the biofuel industry; and/or d) Cereal (e.g. wheat) gluten-starch separation industry. The resultant product(s) may be starch (e.g. purified starch) and/or gluten and/or fibres and/or water solubles (such as soluble pentosans). In one embodiment the present invention relates to the production of starch and/or gluten; and/or e) Improving malting and brewing, e.g. by breaking down grain-based material (e.g. malted barley), and/or e) To degrade AXsol or the breakdown products of AXinsol to ensure viscosity is not increased and/or viscosity is reduced in the reaction mixture; and/or f) To reducing viscosity when degrading grain-based materials, e.g. in biofuel (e.g. bioethanol) production processes.

In one embodiment the xylanase variant of the present invention is used in a feedstuff. Preferably a feedstuff comprising corn or is a corn-based feedstuff.

In one embodiment the xylanase variant of the present invention is used in malting or brewing.

In a further embodiment the xylanase variant of the present invention is used in wheat gluten-starch separation.

In a yet further embodiment the xylanase variant of the present invention is used in the breakdown of grain-based material and may be part of the biofuel (e.g. bioethanol) production process.

Advantages

As mentioned above, the parent xylanase of the present invention is superior for solubilisation of wheat and corn fiber, both water-unextractable arabinoxylans (WU-AX) and the water extractable arabinoxylans (WE-AX). In addition to that the parent xylanase has excellent biochemical properties relevant for e.g. feed production and feed application. The variants of the present invention are all derived from such a parent xylanase and were selected by specifically looking for amino acid positions which when substituted will improve the thermostability, while keeping the biochemical properties of the parent xylanase as unchanged.

Accordingly, the novel xylanase variant taught herein has many advantages compared with known xylanases.

The xylanase variant is thermostable. For example the xylanase variant is significantly more stable than the parent (backbone) xylanase before modification. Suitably the xylanase variant has a Tm value of more than 70° C. (preferably more than 75° C.), wherein the Tm value is measured as the temperature at which 50% residual activity is obtained after 10 min incubation.

The xylanase variants as taught herein and of the present invention are also unexpectedly good at solubilising pentosans.

The xylanase variants as taught herein and of the present invention are unexpectedly good at solubilising AXinsol.

Surprisingly it has been found that the xylanase variant of the present invention is particularly good at degrading xylan-containing materials, such as arabinoxylans, e.g. AXinsol, in a broad spectrum of substrates, corn, wheat, DDGS, etc, in particular corn and corn based substrates, in particular both wheat (including wheat-based) products and corn (including corn-based products). Compared with the benchmark xylanases which are all commercially produced and marketed xylanases, the novel xylanase taught herein was capable of much more efficient degradation and pentosan release from more plant based materials (in particular corn-based substrates) compared with the marketed xylanases. This was completely unexpected. This contrasts with prior-known enzymes, which are often inferior at solubilising AXinsol in corn or corn-based substrates or which are not as efficient in both wheat- and corn-based substrates.

In addition, the xylanase variant of the present invention is particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol) a reduction in viscosity is obtained. This latter effect is essential in some of the claimed applications.

Typically, conventional xylanases may breakdown AXinsol, but will lead to an increase is the polymer production products which will lead to an increase in viscosity of the mixture. This increased viscosity is disadvantageous in many applications.

The xylanase variants of the present invention and as described herein have been found to not only breakdown (solubilise) insoluble arabinoxylans (AXinsol) from a wide range of substrates, including corn, wheat, DDGS, etc, in particular corn and corn-based substrates, in particular both wheat (including wheat-based) products and corn (including corn-based products), but also efficiently breakdown the thus solubilised polymers to ensure viscosity is not raised and/or to reduce viscosity.

The xylanase variants of the present invention and as described herein are capable of degrading AXsol or the breakdown products of AXinsol to ensure viscosity is not increased and/or viscosity is reduced in the reaction mixture.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the novel xylanase variant(s) disclosed herein which is a/are GH10 xylanase(s) is/are particularly good at solubilizing AXinsol in a broad spectrum of substrates, including corn based substrates. Surprisingly, the present inventors have found that the GH10 xylanase variants of the present invention (and taught herein) outperform commercial GH11 xylanases in their ability to solubilize pentosans.

The fact that the present enzymes efficiently solubilize AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-soy diet for example.

It was completely unexpected for a GH10 xylanase to be so good on solubilizing AXinsol in cereals, particularly in corn or corn-based substrates.

The enzymes of the present invention are able to efficiently (and quickly) degrade the polymers and/or oligomers that are produced from solubilisation of AXinsol or that are present in grain-based materials. This leads to an unexpected advantage for the GH10 xylanase variants taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g., bio-based isoprene); or in the wheat gluten-starch separation industry for the production of starch for example.

In addition, the GH10 xylanase variants of the present invention are particularly thermostable. This provides significant advantages in some applications. In particular, in feed applications, enzymes can be subject to heat treatment, e.g. during pelleting processes. Thus the enzymes need to be able to maintain their activity after such processing. The xylanase variants of the present invention are particularly and unexpectedly thermostable.

Furthermore, an improved thermostability is also very beneficial during degradation of starch, which takes place at elevated temperatures during liquefaction (around 85-95 C). Being thermostable allows the addition of the enzyme during this step.

Notably it has been found that the degradation product from use of the xylanase variant on average is shorter for the GH10 enzymes tested herein compared with GH11 enzymes. This enhances the lowering of viscosity effect.

In addition, a further advantage of the GH10 xylanase variants of the present invention (unlike many GH11 xylanases) are unaffected by wheat xylanase inhibitors, e.g. TAXI like proteinaceous inhibitors, which occur in wheat.

One advantage of the present invention is that it improves wheat gluten-starch separation.

The enzyme of the present invention is particularly effective at enhancing the performance of a subject or improving the digestibility of a raw material in a feed and/or for improving feed efficiency in a subject.

Xylan-Containing Material

The xylanase variant of the present invention (or composition comprising the xylanase variant of the present invention) may be used to degrade any xylan-containing material.

In one embodiment the xylan-containing material is any plant material comprising arabinoxylan.

In one embodiment the xylan-containing material is any plant material comprising insoluble arabinoxylan (AXinsol).

In one embodiment the xylan-containing material is a feedstuff or feed component.

In one embodiment the xylan-containing material is a grain-based material (including whole grains or partial grains or malted grains, e.g. malted barley). When the method relates to biofuel production (e.g. bioethanol production) then preferably the xylan-containing material is a grain-based material.

In another embodiment the xylan-containing material may be a barley malt or mash, or malted barley or combinations thereof.

In a yet further embodiment the xylan-containing material may be a cereal flour (e.g. wheat, oat, rye or barley flour). When the method relates to a gluten-starch separation process preferably the xylan-containing material is a cereal flour (e.g. wheat oat, rye or barley flour).

Breakdown or Degradation

The xylanase variants (or composition comprising the variants) of the present invention or as disclosed herein may be used to breakdown (degrade) AXinsol or AXsol or degradation products of AXinsol.

The term "breakdown" or "degrade" in synonymous with hydrolyses.

Solubilisation/Degradation

The present invention relates to a method of degrading a xylan-containing material (preferably an arabinoxylan-containing material, preferably an insoluble arabinoxylan (AXinsol)-containing material) to produce soluble pentosans (which can be polymeric, oligomeric or monomeric).

This method may be described herein as pentosan solubilisation or arabinoxylan solubilisation or AXinsol solubilisation or degradation of AXinsol.

In one embodiment, the present invention relates to a method of degrading (or breaking down) insoluble arabinoxylan (AXinsol). This can also be referred to as solubilisation of insoluble arabinoxylan and/or solubilisation of pentosans.

In a further embodiment of the present invention the method relates to degrading (e.g. breaking down) polymers derived from the degradation of insoluble arabinoxylans.

Arabinoxylan (AX)

The term "arabinoxylans" (AX) as used herein means a polysaccharide consisting of a xylan backbone (1,4-linked xylose units) with L-arabinofuranose (L-arabinose in its 5-atom ring form) attached randomly by 1α→2 and/or 1α→3 linkages to the xylose units throughout the chain. Arabinoxylan is a hemicellulose found in both the primary and secondary cell walls of plants. Arabinoxylan can be found in the bran of grains such as wheat, maize (corn), rye, and barley.

Arabinoxylan (AX) is found in close association with the plant cell wall, where it acts as a glue linking various building blocks of the plant cell wall and tissue, give it both structural strength and rigidity.

The term "pentosan" as used herein is any of a group of carbohydrates which yield pentoses on complete hydrolysis.

Since xylose and arabinose (the constituents of arabinoxylans) are both pentoses, arabinoxylans are usually classified as pentosans.

AX is the principal Non Starch Polysaccharide (NSP)-fraction in several of the most important feed raw material, including wheat and corn.

Its abundance, location within vegetable material and molecular structure cause AX to have a severe, negative impact on feed digestibility, effectively reducing the nutritional value of the raw materials in which it is present. This makes AX an important anti-nutritional factor, reducing animal production efficiency.

In addition AX can have a severe, negative impact when trying to breakdown plant material for example in processes such as brewing, malting, biofuel manufacture, effectively reducing the amount of substrate accessible in the raw plant material.

AXs can also hold substantial amounts of water (which can be referred to as their water holding capacity)—this can cause soluble arabinoxylans to result in (high) viscosity—which is a disadvantage in many applications.

The term "hemicellulose"—as used herein means the polysaccharide components of plant cell walls other than cellulose. The term "hemicellulose" as used herein may mean polysaccharides in plant cell walls which are extractable by dilute alkaline solutions. Hemicelluloses comprise almost one-third of the carbohydrates in woody plant tissue. The chemical structure of hemicelluloses consists of long chains of a variety of pentoses, hexoses, and their corresponding uronic acids. Hemicelluloses may be found in fruit, plant stems, and grain hulls. Xylan is an example of a pentosan consisting of D-xylose units with $1\beta \rightarrow 4$ linkages.

Water Insoluble Arabinoxylan (AXinsol)

Water-insoluble arabinoxylan (AXinsol) also known as water-unextractable arabinoxylan (WU-AX) constitutes a significant proportion of the dry matter of plant material.

In wheat AXinsol can account for 6.3% of the dry matter. In wheat bran and wheat DDGS AXinsol can account for about 20.8% or 13.4% of the dry matter (w/w).

In rye AXinsol can account for 5.5% of the dry matter.

In corn AXinsol can account for 3.5-6% (e.g. 5.1%) of the dry matter. In corn DDGS AXinsol can account for 10-20% (e.g. 12.6%) of the dry matter.

AXinsol causes nutrient entrapment in feed. Large quantities of well digestible nutrients such as starch and proteins remain either enclosed in clusters of cell wall material or bound to side chains of the AX. These entrapped nutrients will not be available for digestion and subsequent absorption in the small intestine.

Water-Soluble Arabinoxylan (AXsol)

Water-soluble arabinoxylan (AXsol) also known as water extractable arabinoxylan (WE-AX) can cause problems in biofuel production, biochemical production, carbohydrate processing and/or malting and/or brewing and/or in feed as they can cause increased viscosity due to the water-binding capacity of AXsol.

In feed AXsol can have an anti-nutritional effect particularly in monogastrics as they cause a considerable increase of the viscosity of the intestinal content, caused by the extraordinary water-binding capacity of AXsol. The increase viscosity can affect feed digestion and nutrient use as it can prevent proper mixing of feed with digestive enzymes and bile salts and/or it slows down nutrient availability and absorption and/or it stimulates fermentation in the hindgut.

In wheat AXsol can account for 1.8% of the dry matter. In wheat bran and wheat DDGS AXsol can account for about 1.1% or 4.9% of the dry matter (w/w).

In rye AXsol can account for 3.4% of the dry matter.

In barley AXsol can account for 0.4-0.8% of the dry matter.

In corn AXsol can account for 0.1-0.4% (e.g. 0.1%) of the dry matter. In corn DDGS AXinsol can account for 0.3-2.5% (e.g. 0.4%) of the dry matter.

In addition, however, to the amount of AXsol present in plant material, when a xylanase solubilises AXinsol in the plant material this can release pentosans and/or oligomers which contribute to AXsol content of the plant material.

One significant advantage of the xylanase variants disclosed herein is that they have the ability to solubilise AXinsol without increasing viscosity. It is presently believed that high molecular weight products are not formed A breakdown of AXsol can decrease viscosity.

A breakdown of AXsol can release nutrients.

Viscosity

The present invention can be used to ensure that the viscosity is not increased and/or to reduce viscosity in any process where the water-binding capacity of AXsol causes an undesirable increase in viscosity.

The present invention relates to ensuring that viscosity is not increased and/or to reducing viscosity by breaking down (degrading) AXsol or by breaking down (degrading) the polymers and/or oligomers produced by solubilising AXinsol.

Without wishing to be bound by theory, by being able to efficiently (quickly) breakdown (degrade) the solubilized polymers (e.g. oligomers) obtained from dissolving AXinsol an undesirable increase in viscosity can be avoided and/or a reduction in viscosity can be obtained. The term "efficiently" as used herein means that the enzyme is capable of degrading the polymers (e.g. oligomers) being formed by solubilisation of the AXinsol faster than the speed with which the AXinsol is degraded (or solubilized).

Reducing viscosity has advantages in many applications as taught herein.

An in vitro assay which attempts to mimic the environment in the small intestine of a chicken was originally described by Bedford & Classen (1993, Poultry Sci., 72, 137-143). The assay consists of a two steps incubation of the feed first at low pH with pepsin followed by incubation with pancreatin at neutral pH. It is generally accepted that the viscosity of the supernatant after end incubation correlates with the viscosity created in vivo in broilers.

Without increasing viscosity and/or a reduction in viscosity as taught herein for feed applications means that addition of the xylanase will result in an unchanged or lower viscosity measured by the method described below. By unchanged it is meant that the measured value, being the average of three repetitions, falls within two standard deviation of the measured value for a wheat sample without xylanase addition.

Viscosity can be measured using the following devices: Rapid ViscoAnalyzer (RVA) (e.g. in bioethanol processing) and Haake VT550 viscometer (Thermofisher) (e.g. is wheat-gluten starch processing). Both devices can monitor viscosity profiles of fuel ethanol processes and wheat starch separation processes.

In the present invention a reduction in viscosity can be calculated by comparing one sample comprising the xylanase of the present invention (or taught herein) compared with another comparable sample without the xylanase of the present invention (or taught herein). Comparing the viscosity reduction profiles of the xylanase of the present invention with those of the market benchmark xylanase(s) demonstrates the enzyme performance. The aim is to improve enzyme performance compared to the market benchmark. The benchmark enzyme(s) for the individual applications are provided in the examples below.

The benchmark enzyme for comparing viscosity reduction in feed applications may be Econase® XT.

An example of a xylanase used in the Bioethanol Industry is Xylathin™.

An example of a Xylanase used in the wheat gluten-starch separation Industry is Shearzyme™.

The benchmark enzyme for review of thermostability may be the parent (backbone) xylanase (e.g. before modification).

In one embodiment of the present invention the xylanases taught herein are viscosity reducers.

Generally, wheat (or other cereal) is first dry-milled to separate the bran and germ from the endosperm, which is ground into flour. This endosperm flour is then further fractionated through a wheat starch separation process into several product streams of varying commercial value. The major aim is to produce a refined grade of A-starch, consisting of large, lenticular granules of 15-40 µm. The second stream B-starch consists of less purified starch granules, which are spherical and small (1-10 µm). (C. C. Maningat, P. A. Seib, S. D. Bassi, K. S. Woo, G. D. Lasater, Chapter 10 from the book "*Starch*" (2009) 441-451, *Wheat starch: production, properties, modification and uses*). Isolated wheat starch forms the starting material for modified starch production with applications in both food- and nonfood-applications. Vital gluten is the third product of added-value in wheat separation processes. The vitality of the isolated wheat gluten is determined by the ability to form viscoelastic networks, required for breadmaking. Vital gluten encapsulate the carbon dioxide formed in dough preparation during baking, and consequently increase the bread volume. (Anne van der Borght, Hans Goesaert, Wim S. Veraverbeke, Jan A. Delcour, *Journal of Cereal Science* 41 (2005) 221-237, *Fractionation of wheat and wheat flour into starch and gluten: overview of the main processes and the factors involved*). It is therefore often used to enrich flours for bread making, to achieve improved bread products. Other markets for gluten include as an additive in vegetarian, meat, fish or poultry products, including those in pet-food industry; in cereal breakfast; or in soy sauce. Due to its thermoplasticity and good film-forming properties, gluten is also used in non-food markets as adhesives. (L. Day, M. A. Augustin, I. L. Batey, C. W. Wrigley, *Trends in Food Science & Technology* 17 (2006) 82-90, *Wheat-gluten uses and industry needs*.).

The xylanase variants taught herein can be used to reduce the viscosity (or not increase viscosity) in processes for separating cereal flour (e.g. wheat, oat, rye or barley flour) into starch and gluten fractions and to improve the separation by degrading oligosaccharides that hinder gluten agglomeration.

Wort viscosity, and the viscosity of barley mash and barley malt in brewing and malting can cause significant disadvantages during brewing and/or malting. The present invention relates to reducing the viscosity (or not increase the viscosity) of wort, barley mash, barley malt or a combination thereof.

Feed or Feedstuff

The xylanase variant or feed additive composition of the present invention may be used as—or in the preparation of—a feed.

The term "feed" is used synonymously herein with "feedstuff".

Preferably the arabinoxylan-containing material of the present invention is a feedstuff, or a constituent of a feedstuff, or a feed component.

The feed may be in the form of a solution or as a solid or as a semi-solid—depending on the use and/or the mode of application and/or the mode of administration.

When used as—or in the preparation of—a feed—such as functional feed—the xylanase variant or composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the xylanase variant or feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term "fodder" as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In one embodiment the feedstuff comprises or consists of corn, DDGS (such as cDDGS), wheat, wheat bran or a combination thereof.

In one embodiment the feed component may be corn, DDGS (e.g. cDDGS), wheat, wheat bran or a combination thereof.

In one embodiment the feedstuff comprises or consists of corn, DDGS (such as cDDGS) or a combination thereof.

In one embodiment a feed component may be corn, DDGS (such as cDDGS) or a combination thereof.

A feedstuff of the present invention may contain at least 30%, at least 40%, at least 50% or at least 60% by weight corn and soybean meal or corn and full fat soy, or wheat meal or sunflower meal.

A feedstuff of the present invention may contain between about 5 to about 40% corn DDGS. For poultry—the feedstuff on average may contain between about 7 to 15% corn DDGS. For swine (pigs)—the feedstuff may contain on average 5 to 40% corn DDGS.

A feedstuff of the present invention may contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grain (DDG), Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wet-cake, Distillers Dried Grain (DDG)—particularly cDDG, wheat bran, and wheat for example.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wheat bran, and wheat for example.

In the present invention the feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" in the present invention encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term "feed" in the present invention encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term "feed" in the present invention encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the xylanase variant (or composition comprising the enzyme) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The xylanase variant (or composition comprising the xylanase variant) of the present invention may be applied to intersperse, coat and/or impregnate a product (e.g. feedstuff or raw ingredients of a feedstuff) with a controlled amount of said enzyme.

In a particularly preferred embodiment the xylanase variant (or composition comprising the xylanase variant) of the present invention is homogenized to produce a powder.

In an alternative preferred embodiment, the enzyme (or composition comprising the enzyme) of the present invention is formulated to granules as described in WO2007/044968 (referred to as TPT granules) or WO1997/016076 or WO1992/012645 incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a Na$_2$SO$_4$.

The method of preparing an enzyme (or composition comprising the enzyme) of the present invention may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the xylanase variant (or composition comprising the xylanase variant) of the present invention is suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for poultry.

Corn Based Feedstuff

In a preferred embodiment the feedstuff may be a corn based feedstuff. The term "corn based feedstuff" as used herein means a feedstuff which comprises or consists of corn (maize) or a by-product of corn.

Preferably the corn based feedstuff comprises corn or a by-product of corn as the major constituent. For example the corn based feedstuff may comprise at least 35% corn or a by-product of corn, such as at least 40% corn or a by-product of corn, such as at least 50% corn or a by-product of corn, such as at least 60% corn or a by-product of corn, such as at least 70% corn or a by-product of corn, such as at least 80% or a by-product of corn, such as at least 90% corn or a by-product of corn, for example 100% corn or a by-product of corn.

In some embodiments the corn based feedstuff may comprise corn or a by-product of corn as a minor constituent; in which case the feedstuff may be supplemented with corn or a by-product of corn. By way of example only the feedstuff may comprise for example wheat supplemented with corn or a by-product of corn.

When corn or the by-product of corn is a minor constituent of the feedstuff, the corn or by-product of corn is at least 5%, preferably at least 10%, preferably at least 20%, preferably at least 30% of the feedstuff.

For the avoidance of doubt the term "corn" as used herein is synonymous with maize, e.g. *Zea mays*.

In one embodiment the by-product of corn may be corn Distillers Dried Grain Solubles (cDDGS) or corn wet-cake or corn Distillers Dried Grain (DDG) or corn gluten meal or corn gluten feed or combinations thereof.

In one embodiment preferably the arabinoxylan-containing material of the present invention comprises a by-product of corn, such as corn Distillers Dried Grain Solubles (cDDGS) or corn wet-cake or corn Distillers Dried Grain (DDG) or corn gluten meal or corn gluten feed or combinations thereof.

Wheat Based Feedstuff

In a preferred embodiment the feedstuff may be a wheat based feedstuff. The term "wheat based feedstuff" as used herein means a feedstuff which comprises or consists of wheat or a by-product of wheat.

Preferably the wheat based feedstuff comprises wheat or a by-product of wheat as the major constituent. For example the wheat based feedstuff may comprise at least 40% wheat or a by-product of wheat, such as at least 60% wheat or a by-product of wheat, such as at least 80% or a by-product of wheat, such as at least 90% wheat or a by-product of wheat, for example 100% wheat or a by-product of wheat.

In some embodiments the wheat based feedstuff may comprise wheat or a by-product of wheat as a minor constituent; in which case the feedstuff may be supplemented with wheat or a by-product of wheat. By way of example only the feedstuff may comprise for example wheat supplemented with wheat or a by-product of wheat.

When wheat or the by-product of wheat is a minor constituent of the feedstuff, the wheat or by-product of wheat is at least 5%, preferably at least 10%, preferably at least 20%, preferably at least 30% of the feedstuff.

In one embodiment the by-product of wheat may be wheat bran, wheat middlings, wheat fibres for example.

Bran is the hard outer layer of grain and consists of combined aleurone and pericarp. Along with germ, it is an integral part of whole grains, and is often produced as a by-product of milling in the production of refined grains. When bran is removed from grains, the grains lose a portion of their nutritional value. Bran is present in and may be milled from any cereal grain, including rice, corn (maize), wheat, oats, barley and millet. Bran is particularly rich in dietary fiber and essential fatty acids and contains significant quantities of starch, protein, vitamins and dietary minerals.

Wheat middlings is coarse and fine particles of wheat bran and fine particles of wheat shorts, wheat germ, wheat flour and offal from the "tail of the mill".

Wheat middlings is an inexpensive by-product intermediate of human food and animal feed. In one embodiment preferably the arabinoxylan-containing material of the present invention comprises wheat bran and/or wheat middlings.

Wet-Cake, Distillers Dried Grains (ddq) and Distillers Dried Grain Solubles (ddgs)

Wet-cake, Distillers Dried Grains and Distillers Dried Grains with Solubles are products obtained after the removal of ethyl alcohol by distillation from yeast fermentation of a grain or a grain mixture by methods employed in the grain distilling industry.

Stillage coming from the distillation (e.g. comprising water, remainings of the grain, yeast cells etc.) is separated into a "solid" part and a liquid part.

The solid part is called "wet-cake" and can be used as animal feed as such.

The liquid part is (partially) evaporated into a syrup (solubles).

When the wet-cake is dried it is Distillers Dried Grains (DDG).

When the wet-cake is dried together with the syrup (solubles) it is Distillers Dried Grans with Solubles (DDGS).

Wet-cake may be used in dairy operations and beef cattle feedlots.

The dried DDGS may be used in livestock, e.g. dairy, beef and swine) feeds and poultry feeds.

Corn DDGS is a very good protein source for dairy cows.

Corn Gluten Meal

In one aspect, the by-product of corn may be corn gluten meal (CGM). CGM is a powdery by-product of the corn milling industry. CGM has utility in, for example, animal feed. It can be used as an inexpensive protein source for feed such as pet food, livestock feed and poultry feed. It is an especially good source of the amino acid cysteine, but must be balanced with other proteins for lysine.

Feed Additive Composition

The feed additive composition of the present invention and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions of the present invention may be mixed with feed or administered in the drinking water.

In one aspect the present invention relates to a method of preparing a feed additive composition, comprising admixing a xylanase as taught herein with a feed acceptable carrier, diluent or excipient, and (optionally) packaging.

Premix

The feedstuff and/or feed additive composition may be combined with at least one mineral and/or at least one vitamin. The compositions thus derived may be referred to herein as a premix.

Malting and Brewing

The xylanase variant (or composition comprising the xylanase variant) of the present invention may be used in malting and brewing.

Barley grains contain 1.7 to 4.1% (w/w) water-extractable and 3.6 to 6.4% (w/w) total beta-glucan (Anderson, M. A., Cook, J. A., & Stone, B. A., Journal of the Institute of Brewing, 1978, 84, 233-239; Henry, J., Journal of the Science of Food and Agriculture, 1985, 36, 1243).

Wheat grains contain 0.1 to 0.8% (w/w) water-extractable and 0.6 to 1.4% (w/w) total beta-glucan (Anderson, M. A. et al (1978) supra).

Efficient hydrolysis of arabinoxylans (AXsol) and beta-glucan is important because such compounds can be involved in production problems such as wort viscosity (Ducroo, P. & Frelon, P. G., Proceedings of the European Brewery Convention Congress, Zurich, 1989, 445; Viëtor, R. J. & Voragen, A. G. J., Journal of the Institute of Brewing, 1993, 99, 243) and filterability and haze formation (Coote, N. & Kirsop, B. H. 1976., Journal of the Institute of Brewing, 1976, 82, 34; Izawa, M., Kano, Y. & Kanimura, M. 1991. Proceedings Aviemore Conference on Malting, brewing and Distilling, 1990, 427).

The present invention provides a method of hydrolysing arabinoxylans (e.g. AXinsol and AXsol) during malting and brewing wherein wheat grains, barley grains or a combination thereof, or portions of the wheat and/or barley grains, are admixed with the xylanase variant of the present invention.

In one aspect of the present invention may relate to a food composition that is a beverage, including, but not limited to, a fermented beverage such as beer and wine, comprising a xylanase variant according to the present invention.

In another aspect of the present invention may relate to a food composition that is a beverage, including, but not limited to, a fermented beverage such as beer and wine, comprising a xylanase variant according to the present invention.

In the context of the present invention, the term "fermented beverage" is meant to comprise any beverage produced by a method comprising a fermentation process, such as a microbial fermentation, such as a bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e.g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing a fermented beverage such as beer comprising mixing the xylanase variant of the present invention with malt or adjunct.

Examples of beers comprise: full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e.g. citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

Breakdown of Grain-Based Material e.g. for Biofuel Production

The xylanase variant (or composition comprising the xylanase variant) of the present invention or as disclosed herein may be used to breakdown (degrade) AXinsol and AXsol during grain processing from e.g. grain-based material. The grain-based material may be whole grains (e.g. whole wheat, barley, rye, triticale or corn grains or mixtures thereof) or portions of the whole grains, or mixtures thereof.

In one embodiment the xylanase variant (or composition comprising the xylanase variant) of the present invention or as disclosed herein may be used to breakdown (degrade) AXinsol and AXsol in grain-based materials or whole grains.

For the avoidance of doubt the whole grains can be mechanically broken.

The grain-based material may be broken down or degraded to glucose. The glucose may subsequently be used as a feedstock for any fermentation process, e.g. for biofuel (e.g. bioethanol) production and/or biochemicals (e.g., bio-based isoprene) production.

The grain-based material may be feedstock for a biofuel (e.g. bioethanol) production process.

Today most fuel ethanol is produced from corn (maize) grain, which is milled or grinded, treated with amylase enzymes to hydrolyse starch to sugars, fermented, and distilled. While substantial progress has been made in reducing costs of ethanol production, substantial challenges remain. Improved techniques are still needed to reduce the cost of biofuel feedstocks for ethanol production. For example, in grain-based ethanol production degradation of arabinoxylans may increase accessibility of starch.

The present invention provides a xylanase variant for use in the breakdown of hemicelluloses, e.g. arabinoxylan—particularly AXinsol and AXsol.

By way of example only, in the European fuel alcohol industry, small grains like wheat, barley and rye are common raw materials, in the US corn is mainly used. Wheat, barley and rye contain, next to starch, high levels of non-starch polysaccharide polymers (NSP), like cellulose, beta-glucan and hemicellulose.

The ratio in which the different NSPs are represented differ for each feedstock. The table below shows the different amounts of NSPs in wheat, barley and rye compared to some other feedstocks.

TABLE 1

Non-starch Polysaccharides present in different feedstocks (g kg$^{-1}$ dry matter)

| | Corn | Wheat | Rye | Barley Hulled | Barley Hulless | Oats Hulled | Oats Hulless |
|---|---|---|---|---|---|---|---|
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[1] | 75 | 89-99 | 116-136 | 144 | 114 | 150 | 113 |
| Total NSP | 97 | 107-119 | 132-152 | 186 | 124 | 232 | 116 |

[1]Non Cellulosic Polysaccharides: pentosans, (arabino)xylans and other hemicelluloses NSPs can give high viscosity to grain mashes due to their large water-binding capacity. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step.

In one embodiment of the present invention the method for degrading grain-based material comprises admixing the xylanase variant as disclosed herein as early as possible in the biofuel (e.g. bioethanol) production process, e.g. preferably during mixing of the grain-based material at the start of the process. One advantage of adding the xylanase variants as disclosed herein at an early stage in the process is that the enzymes breakdown initial viscosity.

In one embodiment of the present invention the method for degrading grain-based material comprises admixing the xylanase variant as disclosed herein prior to or during liquefaction, saccharification, fermentation, simultaneous saccharification and fermentation, and post fermentation, or a combination thereof.

Therefore in one embodiment the present invention relates to reducing viscosity when degrading grain-based materials, e.g. in biofuel (e.g. bioethanol) production processes.

The benefits of using the xylanase variants taught herein to reduce viscosity when degrading grain-based materials, e.g. in biofuel (e.g. bioethanol) production processes are multiple:

Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS (by-product)
Better separation between the solid and liquid part during stillage separation (after distillation). The lower viscosity increases separation efficiency.

A further significant advantage of the present invention is that use of the xylanase variant described herein in biofuel production can also result in improved (by)products from that process such as wet-cake, Distillers Dried Grains (DDG) or Distillers Dried Grains with Solubles (DDGS). Therefore one advantage of the present invention is since the wet-cake, DDG and DDGS are (by)products of biofuel (e.g.

bioethanol) production the use of the present invention can result is improved quality of these (by)products. For example the arabinoxylans in the (by)products can be already dissolved during the biofuel production process.

Cereal (e.g. Wheat) Gluten-Starch Separation

The xylanase variant (or composition comprising the xylanase variant) of the present invention or as disclosed herein may be used to breakdown (degrade) AXinsol and AXsol during wheat starch and gluten separation.

After initial separation of the wheat bran and germ from the endosperm, fractionation of wheat endosperm flour into starch and gluten fractions is industrially applied on large scale to obtain high quality A-starch and byproducts B-starch and vital gluten.

The product of the degradation of the cereal flour (e.g. wheat flour) in the present invention is starch (high quality A-starch).

In addition, by-products B-starch and vital gluten are also produced. Each individual product is then further processed to supplement or modify food product characteristics to the market needs.

There are several wheat separation processes used by industry described in literature. These industrial processes differ mainly in the forms of the flour-water mixtures presented to the fractionation equipment (centrifuge, hydrocyclone, or screen) or in the initial reaction conditions as temperature and applying of shear (Abdulvahit Sayaslan, Lebensm.-Wiss. U.-Technol 37 (2004) 499-515, *Wetmilling of wheat flour: industrial processes and small-sacale test methods*).

In the method for separating a cereal flour (e.g. wheat flour) into starch and gluten fractions the method comprises admixing a cereal flour (e.g. wheat flour), water and a xylanase variant. The cereal flour, water and xylanase variant may be mixed simultaneously or sequentially. In some embodiments the cereal flour (e.g. wheat flour) and water may be admixed before admixing with the xylanase variant.

In general, cereal flour (e.g. wheat flour) is either mixed to a dough or batter, varying between 35 to 63% Dry solids, at temperatures of ~20-45° C. The mixture is then further processed either by:

1) letting the mixture rest for some time (~30 minutes) and sequentially washing out the starch from the mixture using a screen, centrifuge or hydrocyclone to separate the starch milk from the gluten, or
2) applying shear to the mixture, optionally diluting the mixture further and then separating the wheat flour by a hydrocyclone, or a 2- or 3-phase decanter centrifuge.

The term "dry solids" as used herein means total solids (dissolved and undissolved) of a slurry (in %) on a dry weight basis.

In one embodiment of the present invention the method or use as claimed may include the steps of mixing wheat flour to form a dough or batter between 35-63% dry solids, at a temperature of about 20 to about 45° C. and separating the starch from the gluten.

The method of the present invention may further comprise: a) resting the mixture for about 30 minutes and sequentially washing out the starch from the mixture using either a screen, a centrifuge or a hydrocyclone to separate the starch milk from the gluten; or b) applying shear to the mixture and optionally diluting the mixture further, separating the starch from the gluten using a hydrocyclone or a 2- or 3-phase decanter centrifuge.

The present invention provides for improving the separation of the starch and the gluten by adding a xylanase variant as taught herein suitably during the initial mixing step of flour and water in the various processes described above used for wheat starch separation. Separation is improved by adding a xylanase variant during the initial mixing step due to viscosity reduction and the hydrolysis of AXsol and/or AXinsol interfering with the gluten particles. By degrading these poly- and oligosaccharides, gluten agglomeration is enhanced, improving the gluten yield. (S. A. Frederix, C. M. Courtin, J. A. Delcour, J. *Cereal Sci.* 40 (2004) 41-49, *Substrate selectivity and inhibitor sensitivity affect xylanase functionality in wheat flour gluten-starch separation*).

One advantage of the present invention is that it results in higher A-starch yields and/or better quality gluten (e.g. better quality vital gluten).

One advantage of the present invention is that it improves wheat gluten-starch separation.

One of the ways to evaluate gluten quality is by monitoring gluten agglomeration. When a certain amount of friction through kneading of the dough or mixing of the batter is applied, gluten particles tend to agglomerate into larger particles that form a polymeric network, called "vital gluten". "Vital gluten" can be added to food products to improve properties of baked goods such as dough strength, shelf-life and bread volume (L. Day, M. A. Augustin, I. L. Batey and C. W. Wrigley; *Wheat-gluten uses and industry needs; Trends in Food Science & Technology* 17 (2006) 82-90).

In the bakery industry, the quality and quantity of the gluten in a wheat flour is determined by the ICC standard assay NO:155 (AACC 38-12) using a Glutomatic. In this device, a dough is formed from wheat flour (10.0 gr) mixed with a small amount of 2% NaCl solution (4.2-4.8 ml). After 20 seconds of mixing step, the dough is continuously kneaded while being washed for 5 minutes with a 2% NaCl solution at room temperature (~22° C.) pumped through the mixing cup at a flow rate of ~70 ml/minute. During this washing step, the wash water containing starch is collected and the gluten particles form a gluten ball within the Glutomatic sieve holder.

The quality of the gluten is measured by evaluating the gluten agglomeration. This is done by centrifuging the gluten ball in a special centrifuge containing a small sieve. The gluten particles that pass this sieve are weighed (small gluten) and the total amount of gluten is weighed. The gluten index is calculated by (total wet gluten—small wet gluten)/total wet gluten. The more gluten agglomeration is improved, the smaller the small gluten fraction will be and the higher the gluten index value is. A high gluten index, with a theoretical maximum of 100%, indicates a high quality gluten ball.

Another value to quantify the amount of gluten is the dried gluten yield (%). This value is calculated by dividing the grams of total dried gluten by the total amount of dry flour which was used in the experiment. The more dried gluten is recovered, the better the separation is.

This industrial assay is currently under adaptation to simulate a dough separation process used in industry.

Dosages

Preferably, the xylanase variant is present in the xylan-containing material (e.g. feedstuff) in the range of about 500 XU/kg to about 16,000 XU/kg xylan-containing material (e.g. feed), more preferably about 750 XU/kg feed to about 8000 XU/kg xylan-containing material (e.g. feed), preferably about 1500 XU/kg feed to about 3000 XU/kg xylan-containing material (e.g. feed), preferably about 2000 XU/kg feed to about 2500 XU/kg xylan-containing material (e.g. feed), and even more preferably about 1000 XU/kg xylan-containing material (e.g. feed) to about 4000 XU/kg xylan-containing material (e.g. feed).

In one embodiment the xylanase variant is present in the xylan-containing material (e.g. feedstuff) at more than about 500 XU/kg xylan-containing material (e.g. feed), suitably more than about 600 XU/kg xylan-containing material (e.g. feed), suitably more than about 700 XU/kg xylan-containing material (e.g. feed), suitably more than about 800 XU/kg xylan-containing material (e.g. feed), suitably more than about 900 XU/kg xylan-containing material (e.g. feed), suitably more than about 1000 XU/kg xylan-containing material (e.g. feed), suitably more than about 2000 XU/kg, suitably more than about 2500 XU/kg, suitably more than about 3000 XU/kg xylan-containing material (e.g. feed), In one embodiment the xylanase variant is present in the xylan-containing material (e.g. feedstuff) at a concentration of between about 2000 XU/kg to about 2500 XU/kg.

In one embodiment the xylanase variant is present in the xylan-containing material (e.g. feedstuff) at less than about 16,000 XU/kg xylan-containing material (e.g. feed), suitably less than about 8000 XU/kg xylan-containing material (e.g. feed), suitably less than about 7000 XU/kg xylan-containing material (e.g. feed), suitably less than about 6000 XU/kg xylan-containing material (e.g. feed), suitably less than about 5000 XU/kg xylan-containing material (e.g. feed), suitably less than about 4000 XU/kg xylan-containing material (e.g. feed).

Preferably, the xylanase variant may be present in a feed additive composition in range of about 100 XU/g to about 320,000 XU/g composition, more preferably about 300 XU/g composition to about 160,000 XU/g composition, and even more preferably about 500 XU/g composition to about 50,000 XU/g composition, and even more preferably about 500 XU/g composition to about 40,000 XU/g composition.

In one embodiment the xylanase variant is present in the feed additive composition at more than about 100 XU/g composition, suitably more than about 200 XU/g composition, suitably more than about 300 XU/g composition, suitably more than about 400 XU/g composition, suitably more than about 500 XU/g composition.

In one embodiment the xylanase variant is present in the feed additive composition at less than about 320,000 XU/g composition, suitably less than about 160,000 XU/g composition, suitably less than about 50,000 XU/g composition, suitably less than about 40,000 XU/g composition, suitably less than about 30000 XU/g composition.

The xylanase activity can be expressed in xylanase units (XU) measured at pH 5.0 with AZCL-arabinoxylan (azurine-crosslinked wheat arabinoxylan, Xylazyme tablets, Megazyme) as substrate. Hydrolysis by endo-(1-4)-β-D-xylanase (xylanase) produces water soluble dyed fragments, and the rate of release of these (increase in absorbance at 590 nm) can be related directly to enzyme activity. The xylanase units (XU) are determined relatively to an enzyme standard (Danisco Xylanase, available from Danisco Animal Nutrition) at standard reaction conditions, which are 40° C., 5 min reaction time in McIlvaine buffer, pH 5.0.

The xylanase activity of the standard enzyme is determined as amount of released reducing sugar end groups from an oat-spelt-xylan substrate per min at pH 5.3 and 50° C. The reducing sugar end groups react with 3,5-Dinitrosalicylic acid and formation of the reaction product can be measured as increase in absorbance at 540 nm. The enzyme activity is quantified relative to a xylose standard curve (reducing sugar equivalents). One xylanase unit (XU) is the amount of standard enzyme that releases 0.5 μmol of reducing sugar equivalents per min at pH 5.3 and 50° C.

In one embodiment suitably the enzyme is classified using the E.C. classification above, and the E.C. classification designates an enzyme having that activity when tested in the assay taught herein for determining 1 XU.

Preferably, the xylanase variant is present in the mixing step of a wheat starch separation process in the dough or batter in the range of about 0.01 kg/MT DS dough or batter to about 0.60 kg/MT DS, more preferably about 0.05 kg/MT DS to about 0.45 kg/MT DS dough or batter, and even more preferably about 0.10 kg/MT DS to about 0.25 kg/MT DS dough or batter.

In some embodiments (particularly in the wheat starch separation embodiment) the xylanase variant may be dosed in the range of about 0.019 g protein/MT DS wheat flour (which is equivalent to 0.019 mg/kg DS) to about 119 g protein/MT DS wheat flour (which is equivalent to 119 mg/kg DS—where DS means dry solids content and MT means metric ton.

In some embodiments (particularly in the wheat starch separation embodiment) the xylanase variant may be dosed at about 1.19 g protein/MT DS wheat flour (which is equivalent to about 1.19 mg/kg DS)—where DS means dry solids content and MT means metric ton.

In some embodiments (particularly in the wheat starch separation embodiment) the xylanase variant may be dosed in the range of about 9 to about 120000 units/kg wheat flour, suitably between about 500-2400 units/kg wheat flour, suitably between about 900-1200 units/kg wheat flour (wherein 1 unit is defined as the amount of enzyme required to generate 1 micromole of xylose reducing sugar equivalents per minute under the conditions of the birch wood assay: The beta 1-4 xylanase activity of FveXyn4 is measured using 1% xylan from birch wood (Sigma 95588) or 1% arabinoxylan from wheat flour (Megazyme P-WAXYM) as substrates. The assay is performed in 50 mM sodium citrate pH 5.3, 0.005% Tween-80 buffer at 50° C. for 10 minutes. The released reducing sugar is quantified by reaction with 3,5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

In some embodiments (particularly in degrading grain-based material) the xylanase variant may be dosed in the range of about 0.29 g/protein/MT DS wheat (which is equivalent to 0.29 mg/kg DS) to about 0290 g/protein/MT DS wheat (which is equivalent to 290 mg/kg DS).

In some embodiments (particularly in degrading grain-based material) the xylanase may be dosed at 2.9 g/protein/MT DS wheat (which is equivalent to 2.9 mg/kg DS).

In some embodiments (particularly in degrading grain-based material) the xylanase may be dosed in the range of about 22 to about 285000 units/kg, suitably about 1100 to about 5700 units/kg, suitably about 2200 to about 2850 units/kg (wherein 1 unit is defined as the amount of enzyme required to generate 1 micromole of xylose reducing sugar equivalents per minute under the conditions of the birch wood assay discussed above).

The xylanase variant and/or composition comprising the xylanase variant according to the present invention may be designed for one-time dosing or may be designed for use (e.g. feeding) on a daily basis.

The optimum amount of the xylanase variant and/or composition comprising the xylanase variant to be used in the present invention will depend on the product to be treated and/or the method of contacting the product with the composition and/or the intended use for the same.

The amount of xylanase variant used in the compositions should be a sufficient amount to be effective.

The amount of xylanase variant used in the compositions should be a sufficient amount to be effective and to remain sufficiently effective in for example improving the performance of an animal fed feed products containing said composition. This length of time for effectiveness should extend up to at least the time of utilisation of the product (e.g. feed additive composition or feed containing same).

Formulation

In one embodiment the xylanase variant may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the xylanase variant may be coated, for example encapsulated.

In one embodiment the coating protects the xylanase variant from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

In some embodiments the enzyme may be diluted using a diluent, such as starch powder, lime stone or the like.

In one embodiment, the xylanase variant or composition comprising the xylanase variant is in a liquid formulation suitable for consumption preferably such liquid consumption contains one or more of the following: a buffer, salt, sorbitol and/or glycerol.

In another embodiment the xylanase variant or composition comprising the xylanase variant may be formulated by applying, e.g. spraying, the enzyme(s) onto a carrier substrate, such as ground wheat for example.

In one embodiment the xylanase variant or composition comprising the xylanase variant according to the present invention may be formulated as a premix. By way of example only the premix may comprise one or more feed components, such as one or more minerals and/or one or more vitamins.

In one embodiment the xylanase variant for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the xylanase variant and/or composition comprising same (e.g. feed additive composition) and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Forms

The xylanase variant or composition comprising the xylanase variant (e.g. the feed additive composition) of the present invention and other components and/or the feedstuff comprising same may be used in any suitable form.

The xylanase variant or composition comprising same (e.g. feed additive composition) of the present invention may be used in the form of solid or liquid preparations or alternatives thereof. Examples of solid preparations include powders, pastes, boluses, capsules, pellets, tablets, pills, capsules, ovules, solutions or suspensions, dusts, and granules which may be wettable, spray-dried or freeze-dried. Examples of liquid preparations include, but are not limited to, aqueous, organic or aqueous-organic solutions, suspensions and emulsions.

The composition comprising the xylanase variant may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Subject

The term "subject", as used herein, means an animal that is to be or has been administered with a xylanase variant according to the present invention or a feed additive composition according to the present invention or a feedstuff comprising said feed additive composition according to the present invention.

The term "subject", as used herein, means an animal.

In one embodiment, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of ruminants such as cattle (e.g. cows or bulls (including calves)), monogastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain per unit of feed when the animal is fed ad-libitum or a specified amount of feed during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Combination with Other Components

The xylanase variant of the present invention may be used in combination with other components.

In one embodiment the xylanase variant of the present invention may be used in combination with a probiotic or a direct fed microbial (DFM), e.g. a direct fed bacteria.

The combination of the present invention comprises the xylanase variant of the present invention or a composition comprising the xylanase variant, e.g. a feed additive composition, and another component which is suitable for human or animal consumption and is capable of providing a medical or physiological benefit to the consumer.

In one embodiment the "another component" may be one or more further enzymes (e.g. further feed enzymes or brewing or malting enzymes, or grain processing enzymes or wheat gluten-starch separation enzymes).

Suitable additional enzymes for use in the present invention may be one or more of the enzymes selected from the group consisting of: endoglucanases (E.C. 3.2.1.4); cellobiohydrolases (E.C. 3.2.1.91), β-glucosidases (E.C. 3.2.1.21), cellulases (E.C. 3.2.1.74), lichenases (E.C. 3.1.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), amylases, alpha-amylases (E.C. 3.2.1.1), other xylanases (E.C. 3.2.1.8, E.C. 3.2.1.32, E.C. 3.2.1.37, E.C. 3.1.1.72, E.C. 3.1.1.73), glucoamylases (E.C. 3.2.1.3), hemicellulases, proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)), debranching enzymes, cutinases, esterases and/or mannanases (e.g. a β-mannanase (E.C. 3.2.1.78)).

In one embodiment (particularly for feed applications) the other component may be one or more of the enzymes selected from the group consisting of an amylase (including α-amylases (E.C. 3.2.1.1), G4-forming amylases (E.C. 3.2.1.60), β-amylases (E.C. 3.2.1.2) and γ-amylases (E.C. 3.2.1.3)); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or a phytase (e.g. a 6-phytase (E.C.3.1.3.26) or a 3-phytase (E.C. 3.1.38)).

In one embodiment (particularly for feed applications) the other component may be a combination of an amylase (e.g. α-amylases (E.C. 3.2.1.1)) and a protease (e.g. subtilisin (E.C. 3.4.21.62)).

In one embodiment (particularly for feed applications) the other component may be a β-glucanase, e.g. an endo-1,3 (4)-β-glucanases (E.C. 3.2.1.6).

In one embodiment (particularly for feed applications) the other component may be a phytase (e.g. a 6-phytase (E.C.3.1.3.26) or a 3-phytase (E.C. 3.1.38).

In one embodiment (particularly for feed applications) the other component may be a mannanases (e.g. a β-mannanase (E.C. 3.2.1.78)).

In one embodiment (particularly for feed applications) the other component may be a lipase lipase (E.C. 3.1.1.3), a lipid acyltransferase (generally classified as E.C. 2.3.1.x), or a phospholipase (E.C. 3.1.1.4, E.C. 3.1.1.32 or E.C. 3.1.1.5), suitably a lipase (E.C. 3.1.1.3).

In one embodiment (particularly for feed applications) the other component may be a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment the additional component may be a stabiliser or an emulsifier or a binder or carrier or an excipient or a diluent or a disintegrant.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others. Examples of granulation binders include one or more of: polyvinylpyrrolidone, hydroxypropylmethylcellulose (HPMC), hydroxypropylcellulose (HPC), sucrose, maltose, gelatin and acacia.

"Carriers" mean materials suitable for administration of the enzyme and include any such material known in the art such as, for example, any liquid, gel, solvent, liquid diluent, solubilizer, or the like, which is non-toxic and which does not interact with any components of the composition in a deleterious manner.

The present invention provides a method for preparing a composition (e.g. a feed additive composition) comprising admixing an enzyme of the present invention with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of "excipients" include one or more of: microcrystalline cellulose and other celluloses, lactose, sodium citrate, calcium carbonate, dibasic calcium phosphate, glycine, starch, milk sugar and high molecular weight polyethylene glycols.

Examples of "disintegrants" include one or more of: starch (preferably corn, potato or tapioca starch), sodium starch glycollate, croscarmellose sodium and certain complex silicates.

Examples of "diluents" include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes) to the xylanase of the present invention.

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Isolated

In one aspect, preferably the amino acid sequence, or nucleic acid, or enzyme according to the present invention is in an isolated form. The term "isolated" means that the sequence or enzyme or nucleic acid is at least substantially free from at least one other component with which the sequence, enzyme or nucleic acid is naturally associated in nature and as found in nature. The sequence, enzyme or nucleic acid of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the sequence, enzyme or nucleic acid according to the present invention is in a purified form. The term "purified" means that the given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

Nucleotide Sequence

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In one embodiment the term "nucleotide sequence" means cDNA.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) Nuc Acids Res Symp Ser 215-23 and Horn T et al., (1980) Nuc Acids Res Symp Ser 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. xylose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) Tetrahedron Letters 22, p 1859-1869, or the method described by Matthes et al., (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (Science (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology or identity with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, in some embodiments a homologous sequence is taken to include an amino acid or a nucleotide sequence which may be at least 97.7% identical, preferably at least 98 or 99% identical to the subject sequence.

In some embodiments a homologous sequence is taken to include an amino acid or a nucleotide sequence which may be at least 85% identical, preferably at least 90 or 95% identical to the subject sequence.

Typically, the homologues will comprise the same active sites etc. as the subject amino acid sequence for instance. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In the present context, "the subject sequence" relates to the nucleotide sequence or polypeptide/amino acid sequence according to the invention.

Preferably, the % sequence identity with regard to a polypeptide sequence is determined using SEQ ID NO:2 as the subject sequence in a sequence alignment. In one embodiment, the polypeptide subject sequence is selected from the group consisting of SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

Preferably, the % sequence identity with regard to a nucleotide sequence is determined using SEQ ID NO:1 as the subject sequence in the sequence alignment. In one embodiment, the subject sequence for nucleotide sequences may be selected from the group consisting of SEQ ID NO:1, SEQ ID NO:3, SEQ ID NO:5, SEQ ID NO:6, SEQ ID NO:19, SEQ ID NO:10, SEQ ID NO:11, SEQ ID NO:14, SEQ ID NO:15, SEQ ID NO:17, or SEQ ID NO:18.

A "parent nucleic acid" or "parent amino acid" means a nucleic acid sequence or amino acid sequence, encoding or coding for the parent polypeptide, respectively.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids, preferably over at least 200 contiguous amino acids.

In one embodiment the present invention relates to a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, in one embodiment a homologous sequence or foreign sequence is taken to include a nucleotide sequence which may be at least 97.7% identical, preferably at least 98 or 99% identical to a nucleotide sequence encoding a polypeptide of the present invention (the subject sequence).

In another embodiment, a homologous sequence is taken to include a nucleotide sequence which may be at least 85% identical, preferably at least 90 or 95% identical to a nucleotide sequence encoding a polypeptide of the present invention (the subject sequence).

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology or % identity between two or more sequences.

% homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology or % identity when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology or % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60), such as for example in the GenomeQuest search tool (www.genomequest.com).

Although the final % homology or % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 9 |
| GAP EXTENSION | 2 |

| FOR CLUSTAL | DNA | PROTEIN |
|---|---|---|
| Weight Matrix | IUB | Gonnet 250 |
| GAP OPENING | 15 | 10 |
| GAP EXTEND | 6.66 | 0.1 |

In one embodiment, CLUSTAL may be used with the gap penalty and gap extension set as defined above.

Suitably, the degree of identity with regard to a nucleotide sequence or protein sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least contiguous nucleotides/amino acids, preferably over at least 100 contiguous nucleotides/amino acids.

Suitably, the degree of identity with regard to a nucleotide sequence sequence is determined over at least 100 contiguous nucleotides, preferably over at least 200 contiguous nucleotides, preferably over at least 300 contiguous nucleotides, preferably over at least 400 contiguous nucleotides, preferably over at least 500 contiguous nucleotides, preferably over at least 600 contiguous nucleotides, preferably over at least 700 contiguous nucleotides, preferably over at least 800 contiguous nucleotides.

Suitably, the degree of identity with regard to a nucleotide sequence may be determined over the whole sequence taught herein.

Suitably, the degree of identity with regard to a nucleotide sequence may be determined over the whole sequence taught herein as the mature sequence, e.g. SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

Suitably, the degree of identity with regard to a nucleotide sequence may be determined over the whole sequence as taught herein as SEQ ID NO:2.

Suitably, the degree of identity with regard to a protein (amino acid) sequence is determined over at least 100 contiguous amino acids, preferably over at least 200 contiguous amino acids, preferably over at least 300 contiguous amino acids.

Suitably, the degree of identity with regard to an amino acid or protein sequence may be determined over the whole sequence taught herein.

Suitably, the degree of identity with regard to an amino acid or protein sequence may be determined over the whole sequence taught herein as the mature sequence, e.g. SEQ ID NO:2, SEQ ID NO:4, SEQ ID NO:16, SEQ ID NO:7, SEQ ID NO:8, SEQ ID NO:9, SEQ ID NO:12, or SEQ ID NO:13.

Suitably, the degree of identity with regard to an amino acid or protein sequence may be determined over the whole sequence taught herein as SEQ ID NO:2.

In the present context, the term "query sequence" means a homologous sequence or a foreign sequence, which is aligned with a subject sequence in order to see if it falls within the scope of the present invention. Accordingly, such query sequence can for example be a prior art sequence or a third party sequence.

In one preferred embodiment, the sequences are aligned by a global alignment program and the sequence identity is calculated by identifying the number of exact matches identified by the program divided by the length of the subject sequence.

In one embodiment, the degree of sequence identity between a query sequence and a subject sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the subject sequence.

In yet a further preferred embodiment, the global alignment program is selected from the group consisting of CLUSTAL and BLAST (preferably BLAST) and the sequence identity is calculated by identifying the number of exact matches identified by the program divided by the length of the subject sequence.

The sequences may also have deletions, insertions or substitutions of amino acid residues result in a functionally equivalent substance. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, ß-alanine*, L-α-amino butyric acid*, L-γ-amino butyric acid*, L-α-amino isobutyric acid*, L-ε-amino caproic acid$^#$, 7-amino heptanoic acid*, L-methionine sulfone$^{#*}$, L-norleucine*, L-norvaline*, p-nitro-L-phenylalanine*, L-hydroxyproline$^#$, L-thioproline*, methyl derivatives of phenylalanine (Phe) such as 4-methyl-Phe*, pentamethyl-Phe*, L-Phe (4-amino)$^#$, L-Tyr (methyl)*, L-Phe (4-isopropyl)*, L-Tic (1,2,3,4-tetrahydroisoquinoline-3-carboxyl acid)*, L-diaminopropionic acid$^#$ and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

In one embodiment the xylanase for use in the present invention may comprise a polypeptide sequence shown as SEQ ID NO:2, SEQ ID NO:4, SEQ ID NO:16, SEQ ID NO:7, SEQ ID NO:8, SEQ ID NO:9, SEQ ID NO:12, or SEQ ID NO:13 with a conservative substitution of at least one of the amino acids.

Suitably there may be at least 2 conservative substitutions, such as at least 3 or at least 4 or at least 5.

Suitably there may be less than 15 conservative substitutions, such as less than 12, less than 10, or less than 8 or less than 5.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Amino Acid Numbering

In the present invention, a specific numbering of amino acid residue positions in the xylanases used in the present invention may be employed. By alignment of the amino acid sequence of a sample xylanases with the xylanase of the present invention (particularly SEQ ID NO:2) it is possible to allot a number to an amino acid residue position in said sample xylanase which corresponds with the amino acid residue position or numbering of the amino acid sequence shown in SEQ ID NO:2 of the present invention.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringency conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Preferably hybridisation is analysed over the whole of the sequences taught herein.

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein. In one embodiment the organism is an expression host.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal or yeast cells.

Examples of suitable bacterial host organisms are gram positive or gram negative bacterial species.

In one embodiment the xylanases taught herein are expressed in the expression host *Trichoderma reesei*.

In some embodiments the expression host for the xylanases taught herein may be one or more of the following fungal expression hosts: *Fusarium* spp. (such as *Fusarium oxysporum*); *Aspergillus* spp. (such as *Aspergillus niger, A. oryzae, A. nidulans,* or *A. awamori*) or *Trichoderma* spp. (such as *T. reesei*).

In some embodiments the expression host may be one or more of the following bacterial expression hosts: *Streptomyces* spp. or *Bacillus* spp. (e.g. *Bacillus subtilis* or *B. licheniformis*).

The use of suitable host cells—such as yeast and fungal host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

In one embodiment the organism is an expression host.

Suitable organisms may include a prokaryote, fungus, yeast or a plant. The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism. The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

Transformation of Host Cells/Organism

As indicated earlier, the host organism can be a prokaryotic or a eukaryotic organism. Examples of suitable prokaryotic hosts include E. coli, Streptomyces spp. and Bacillus spp., e.g. Bacillus subtilis.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of Aspergillus as a host microorganism is described in EP 0 238 023.

Transformation of prokaryotes, fungi and yeasts are generally well known to one skilled in the art.

A host organism may be a fungus—such as a mould. Examples of suitable such hosts include any member belonging to the genera Trichoderma (e.g. T. reesei), Thermomyces, Acremonium, Fusarium, Aspergillus, Penicillium, Mucor, Neurospora and the like.

In one embodiment, the host organism may be a fungus. In one preferred embodiment the host organism belongs to the genus Trichoderma, e.g. T. reesei).

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Large Scale Application

In one preferred embodiment of the present invention, the amino acid sequence is used for large scale applications.

Preferably the amino acid sequence is produced in a quantity of from 1 g per liter to about 100 g per liter of the total cell culture volume after cultivation of the host organism.

Suitably the amino acid sequence may be produced in a quantity of from 30 g per liter to about 90 g per liter of the total cell culture volume after cultivation of the host organism.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The present invention is further described by the following examples which should not be construed as limiting the scope of the invention.

EXAMPLES

Media and Solutions—Abbreviations

In the experimental disclosure which follows, the following abbreviations apply: PI (Performance Index); M (molar); mM (millimolar); µM (micromolar); µmol (micromoles); g (grams); mg (milligrams); µg (micrograms); L (liters); ml and mL (milliliters); µl and µL (microliters); nm (nanometers); U (units); sec (seconds); min(s) (minute/minutes); ° C. (degrees Centigrade); rpm (revolutions per minute); $H_2O$ (water); $dH_2O$ (deionized water); HCl (hydrochloric acid); cDNA (copy or complementary DNA); DNA (deoxyribonucleic acid); RNA (ribonucleic acid); BSA (Bovine serum albumin); NaCl (sodium chloride); v/v (volume to volume); w/w (weight to weight); g (gravity); OD (optical density); ppm (parts per million); $OD_{280}$ (optical density at 280 nm); $OD_{600}$ (optical density at 600 nm); $A_{595}$ (absorbance at 595 nm); PAGE (polyacrylamide gel electrophoresis); PEG (polyethylene glycol); PCR (polymerase chain reaction); SDS (sodium dodecyl sulfate); SEL (Site Evaluation Libraries); CL (combinatorial libraries); Tris (tris(hydroxymethyl) aminomethane); Tris-HCl (tris[Hydroxymethyl]aminomethane-hydrochloride); MES (4-Morpholineethanesulfonic acid); WE-AX (water extractable arabinoxylan); WU-AX (water unextractable arabinoxylan); PAHBAH (4-Para-Hydroxybenzoic Acid Hydrazide); DTT (1,4-dithio-DL-threitol); HPLC (high pressure liquid chromatography); SEC (Size Exclussion Chromatography); MTP (Microtiter plate); GE Healthcare (GE Healthcare, Chalfont St. Giles, United Kingdom); DNA2.0 (DNA2.0, Menlo Park, Calif.); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); Sigma (Sigma Chemical Co., St. Louis, Mo.); NCBI (National Center for Biotechnology Information); Applied Biosystems (Applied Biosystems, Foster City, Calif.); Millipore (Millipore, Billerica, Mass.); Bio-Rad (Bio-Rad, Hercules, Calif.); Invitrogen (Invitrogen Corp., San Diego, Calif.); Pierce (Pierce Biotechnology, Rockford, Ill.); Molecular Devices (Molecular Devices, Corp., Sunnyvale, Calif.); Baseclear (Baseclear BV, Inc., Leiden, the Netherlands); Geneart (Geneart GmbH, Regensburg, Germany); Waters (Waters, Inc., Milford, Mass.); Dionex (Dionex, Corp., Sunnyvale, Calif.); Fluka Chemie AG (Fluka Chemie AG, Buchs, Switzerland); Beckman (Beckman Coulter, USA); Agilent (Agilent Technologies, Calif., USA) and Eppendorf (Eppendorf AG, Germany).

Screening Assays

The following assays were used to screen the variants of FveXyn4 obtained from the site evaluation libraries described in Example 1. Data from each assay and for each variant is calculated as a relative Performance Index (PI) value. The PI value compares the measured performance of the variant and the standard enzyme at the same protein concentration and is calculated as the ratio between variant performance and standard enzyme performance. A performance index (PI) that is greater than 1 (PI>1) indicates improved performance by a variant as compared to the standard enzyme (e.g., FveXyn4), while a PI of 1 (PI=1) identifies a variant that performs the same as the standard enzyme, and a PI that is less than 1 (PI<1) identifies a variant that performs worse than the standard enzyme.

Activity Assay I

The xylanase activity of enzyme samples was determined by measuring amount of reducing sugars released from hydrolysed wheat WE-AX (water extractable arabinoxylan). The amount of reducing sugars was measured by PAHBAH-method. Briefly, by heat and alkaline conditions the reducing end groups react with the colorless PAHBAH (4-Para-Hydroxybenzoic Acid Hydrazide), whereby PAHBAH is oxidized and absorbance is measured at 410 nm (Lever, 1972, Analytical Biochemistry. 47, 273-279). 0.5% WE-AX substrate, pH 5.0 was prepared by moisterising 0.25 g soluble wheat arabinoxylan (e.g. Megazyme, high viscosity ~43 cSt, P-WAXYH) with 2.5 ml 96% Ethanol, before adding 50 ml 0.1 M sodium acetate, pH 5.0. The solution is heated under stirring to boiling, and is cooled under stirring to RT. The solution may be stored for up to 1 week at 4° C.

PAHBAH working solution was prepared by mixing 5% (w:v) PAHBAH (4-Hydroxybenzhydrazide, e.g. Sigma-Aldrich H9882) stock solution in 0.5 M HCl with 0.5 M NaOH at a 1:4 (v/v) ratio. The solution was prepared on the day of analysis and protected from light.

Enzyme samples were diluted in 0.1 M sodium acetate, pH 5.0, 0.1% BSA to a concentration of 1 ug/ml prior to analysis. 25 µL diluted enzyme sample was mixed with 150 µL 0.5% WE-AX substrate, pH 5.0 and incubated at 30° C. for 15 min with shaking. After incubation, 45.4 µL reaction sample was mixed with 135 µL PAHBAH working solution and incubated at 95° C. for 5 min before cooled to 20° C. for 10 sec. 100 µL sample was transferred to a microtiter plate well and the plate was read at 410 nm.

The activity (Activity I) of all variants was calculated as the mean of three replicates subtracted blank including 0.1 M sodium acetate, pH 5.0, 0.1% BSA buffer instead of enzyme. Specific activity I was calculated based on Activity I and the protein concentration determined by HPLC (see procedure below). The performance index for Specific activity I of each variant was calculated as the ratio between specific activity for the variant and standard enzyme so that PI for Specific activity I of FveXyn4 was 1. Performance index for Activity I of each variant was calculated as the ratio between activity for the variant and standard enzyme so that PI for Activity I of FveXyn4 was 1.

Activity Assay II

The FveXyn4 variants were assayed for xylanase activity as described in activity assay I; however 0.1 M sodium acetate, pH 5.0, 0.1% BSA was substituted with 25 mM MES buffer, pH 6.0.

The activity (Activity II) of all variants was calculated as the mean of three replicates subtracted blank including 25 mM MES buffer, pH 6.0 instead of enzyme. Specific activity II was calculated based on Activity II and the protein concentration determined by HPLC (see procedure below). The performance index for Specific activity II of each variant was calculated as the ratio between specific activity for the variant and standard enzyme so that PI for Specific activity II of FveXyn4 was 1. Performance index for Activity II of each variant was calculated as the ratio between activity for the variant and standard enzyme so that PI for Activity II of FveXyn4 was 1.

Thermostability Assay I

Thermostability of the FveXyn4 variants was measured by diluting and pre-incubating the variants in 0.1 M sodium acetate, pH 5.0, 0.1% BSA at 63 C° for 10 min. Subsequently the residual activity was measured by the Xylanase activity assay I described above. The residual activity (Stressed activity I) of all stressed variants was calculated as the mean of three replicates subtracted blank including 0.1 M sodium acetate, pH 5.0, 0.1% BSA buffer instead of enzyme. The activity (ThermoStab I) of each variant was calculated as the ratio between Stressed activity I and Activity I measured in Activity assay I. The performance index for Thermostability I of each variant was calculated as the ratio between ThermoStab I for the variant and standard enzyme so that PI for Thermostability I of FveXyn4 was 1.

Thermostability Assay II

Thermostability of the FveXyn4 variants was measured by diluting and pre-incubating the variants in 25 mM MES buffer, pH 6.0 at 61° C. for 10 min. Subsequently the residual activity was measured by the Xylanase activity assay II described above.

The activity (Stressed activity II) of all stressed variants was calculated as the mean of three replicates subtracted blank including 25 mM MES buffer, pH 6.0 instead of enzyme. The residual activity (ThermoStab II) of each variant was calculated as the ratio between Stressed activity II and Activity II measured in Activity assay II. The performance index for Thermostability II of each variant was calculated as the ratio between ThermoStab II for the variant and standard enzyme so that PI for Thermostability II of FveXyn4 was 1.

Pepsin Resistance Assay

The ability of FveXyn4 variants to withstand pepsin degradation was measured by diluting and incubating the variants in 0.2 mg/ml Pepsin solution at 40° C. for 2 hours. Subsequently the residual activity was measured by the Xylanase activity assay II described above.

0.2 mg/ml Pepsin solution was prepared by dissolving 0.2 g Pepsin (e.g. Sigma-Aldrich, P-7000) in 1000 ml 0.1 M Glycine buffer, pH 3.5 and always prepared fresh on the day of analysis.

The activity (Pepsin stressed activity) of all stressed variants was calculated as the mean of three replicates subtracted a blank including 0.2 mg/ml Pepsin solution buffer instead of enzyme. The pepsin resistance (Pepsin res) of each variant was calculated as the ratio between the Pepsin stressed activity and Activity II measured in activity assay II. The Performance index for Pepsin resistance of each variant was calculated as the ratio between Pepsin resistance for the variant and standard enzyme so that PI for Pepsin resistance of FveXyn4 was 1.

Bradford Analysis

Culture supernatants were diluted 6.5 times on the Biomek robot (Beckman Coulter, USA) with buffer B (25 mM Na Acetate, 250 mM NaCl, pH 4.0). 175 µL of Quick Start Bradford 1× Dye Reagent (BioRad cat #500-0205) was mixed with 5 µL of the diluted sample in MTPs (Costar, 9017) and incubated at 20° C. for 10 minutes in an iEMS shaker (750 rpm shaking) (Thermo Scientific). The absorbance was measured at 595 nm in a MTP-reader with 5 sec. pre-shaking ( ). Protein concentrations were calculated according to a FveXyn4 standard curve (0-0.8 mg/ml), see Table A.

TABLE A

| Protein standards: 52 µL FveXyn4 solution in selected wells | | | | | | | | |
|---|---|---|---|---|---|---|---|---|
| C6 | D6 | C12 | D12 | G6 | H6 | G12 | H12 | |
| 0.8 | 0.6 | 0.4 | 0.2 | 0.1 | 0.05 | 0.01 | 0 | mg/ml |

A280 nm Measurements and Normalization

The samples from the protein purification step (see below) were diluted 4 times (3:1 v:v) with buffer C (25 mM Na Acetate, 400 mM NaCl, pH 4.0) to a final volume of 60 µl in MTPs (Costar, 3635) using the Biomek robot (Beckman Coulter, USA). Absorbance was measured at 280 nm ($A_{280\,nm}$). Protein concentrations were calculated according to a FveXyn4 standard curve (0-0.8 mg/ml), see Table B.

TABLE B

| Protein standards: 60 µl FveXyn4 solution in selected wells | | | | | | | | |
|---|---|---|---|---|---|---|---|---|
| C6 | D6 | C12 | D12 | G6 | H6 | G12 | H12 | |
| 0.8 | 0.6 | 0.4 | 0.2 | 0.1 | 0.05 | 0.01 | 0 | mg/ml |

Using the concentrations determined by $A_{280\,nm}$ measurements all samples were diluted to 50 ppm using the Biomek robot (Beckman Coulter, USA). These normalised samples were used as enzyme stock solution in assays described above Protein Determination by HPLC A MTP (Agilent Part NO:5042-1385) containing 100 µL enzyme stock solution with an approximate concentration of 50 ppm per well was used for the High Performance Liquid Chromatography (HPLC) protein determination method. An Agilent 1260 or 1290 (Hewlett Packard) HPLC equipped with an Acuity UPLC BEH 125 SEC (Waters) column was used to separate remaining contaminants. Sample was eluted from the column using 25 mM sodium phosphate buffer pH 6.8 containing 250 mM sodium chloride. Absorbance was measured at 220 nm, integrated using ChemStation software (Agilent Technologies) and the protein concentration of samples was determined based on a standard curve of purified FveXyn4 protein/enzyme having the amino acid sequence of SEQ ID NO:2

Example 1

Generation of *Fusarium verticilliodes* Xylanase 4 (FveXyn4) Site Evaluation Libraries The *Fusarium verticilliodes* FveXyn4 xylanse gene is shown SEQ ID NO:2 (FIG. 6).

Plasmid and Library Construction

A DNA sequence containing the coding region for xylanase FveXyn4 (the family GH10) from the filamentous fungus *Fusarium verticilloides* was amplified from the genomic DNA with the gene specific primers extended with the attB1 and attB2 sites to allow for the Gateway® BP recombination cloning into the pDonor221 vector (Invitrogen, USA) (SEQ ID NO:5, FIG. 9). The coding cDNA sequence of FveXyn4 xylanase is given in SEQ ID NO:6 (FIG. 10). Phusion DNA polymerase (Finnzymes OY, Finland) was used for PCR amplification to minimize sequence errors. A PCR fragment obtained was verified by sequence analysis. The pEntry-FveXyn4 plasmid, as shown in FIG. 1, was used by BaseClear (Netherlands) and Geneart GmH (Germany) as templates for construction of both Site Evaluation Libraries (SELs) or Combinatorial (CLs) libraries.

Site Evaluation Libraries were made for 302 amino acid positions of the FveXyn4 mature polypeptide (SEQ ID NO:2, FIG. 6). The number of mutant variants per each site evaluation library varied, with some exceptions, between 14 and 19. Each variant was confirmed by DNA sequencing analysis prior to protein activity evaluation. All variants were recombined via the Gateway® LR technology with the destination vector pTTTpyr2 resulting in final expression plasmids pTTTpyr2-FveXyn4. Plasmids were generated in the *Escherichia coli* DH5a strain, purified, sequenced, arrayed individually in 96 MTPs and used for fungal transformation as described further.

The expression vector contains the *T. reesei* cbhl promoter and terminator regions allowing for a strong inducible expression of a gene of interest, the *Aspergillus nidulans* amdS and *T. reesei* pyr2 selective markers conferring growth of transformants on minimal medium with acetamide in the absence of uridine (FIG. 2). The plasmids are maintained autonomously in the fungal cell due to *T. reesei* derived telomere regions. Usage of replicative plasmids results in increased frequencies of transformation and circumvents problems of locus-dependent expression observed with integrative fungal transformation.

Fungal Strains, Growth Media and Transformation

Using a PEG-Protoplast method plasmids (5-10 μl) from SEL libraries were transformed in a *T. reesei* strain deleted for major cellulases and xylanase 2 (Δcbh1 Δcbh2 Δegl1 Δegl2 Δegl3 Δegl4 Δegl5 Δegl6 Δbgl1 Δman1 Δxyn2 pyr2-). All high throughput transformations were performed robotically in a 24 well MTP format using Biomek robots (Beckman Coulter, USA). Plasmids with variants were received from the vendors in 96 well MTPs arrayed according to a predetermined layout. Transformation mixtures containing approximately 1 μg of DNA and $5\times10^6$ protoplasts in a total volume of 50 μl were treated with 200 ul of 25% PEG solution, diluted with 1 volumes of 1.2M sorbitol/10 mM Tris, pH7.5/10 mM $CaCl_2$ solution, rearranged robotically into 24 well MTPs and mixed with 1 ml of 3% agarose Minimal Medium containing 1M sorbitol and 10 mM NH4Cl. After growth of transformants, spores from each well were pooled and repatched on fresh 24 well MTPs with MM containing acetamide for additional selective pressure. Once sporulated, spores were harvested and used for inoculation of liquid cultures either in a 24-well MTP format (for screening) or shake flasks (for validation studies) in the following production medium: 37 g/L glucose, 1 g/L sophorose, 9 g/L casmino acids, 10 g/L $(NH_4)_2SO_4$, 5 g/L $KH_2PO_4$, 1 g/L $CaCl_2x2H_2O$, 1 g/L $MgSO_4x7H_2O$, 33 g/L 1,4-Piperazinebis(propanesulfonic acid), pH 5.5, 2.5 ml/L of 400× *T. reesei* trace elements (175 g/L citric acid, 200 g/L $FeSO_4x7H_2O$, 16 g/L $ZnSO_4x7H_2O$, 3.2 g/L $CuSO_4x5H_2O$, 1.4 g/L $MnSO_4xH_2O$, 0.8 g/L boric acid). 1 ml of production medium was added to produce variants in 24 well MTPs. For shake flasks, volumes were scaled up.

Protein Expression

Figure 3:
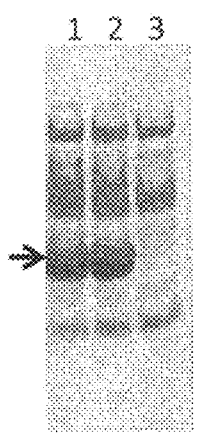
FIG. 3 shows the expression of FveXyn4 xylanase in *T. reesei*. SDS PAGE analysis of *T. reesei* culture samples expressing FveXyn4 xylanase. 10 µl of culture grown for 6 days in MTP was loaded per lane, as indicated: Lane 1 and 2, containing the pTTTpyr2-FveXyn4 plasmid; Lane 3, the host strain. FveXyn4 specific band is indicated by an arrow.

Plates were grown for 6 days at 28° C. and 80% humidity with constant rotational mixing at 200 rpm. Cells were harvested by centrifugation at 2500 rpm for 10 minutes and filtered through Millipore Multiscreen filterplate using a Millipore vacuum system. The culture supernatants were used to assay their performance as well as expression level (FIG. 3). Protein profile of the whole broth samples was determined by PAGE electrophoresis on NuPAGE® Novex 10% Bis-Tris Gel with MES SDS Running Buffer (Invitrogen, Carlsbad, Calif., USA). Polypeptide bands were visualized with SimplyBlue SafeStain (Invitrogen, Carlsbad, Calif., USA). Total protein content was measured by Bradford analysis.

Protein Purification

Culture supernatants were diluted 1:2 with sample buffer (25 mM Na Acetate, 50 mM NaCl, pH 4.0) and loaded on top of SP Sepharose FF resin (GF Healthcare, 17-0729) equilibrated with buffer A (25 mM Na Acetate, 100 mM NaCl, pH 4.0) in a MTP filter plate (Millipore, #MDRPN0410) pre-wetted with 90% ethanol. Fractions were collected in a MTP (Agilent Part NO:5042-1385) during 1 min of centrifugation (50×g). Subsequently, fractions were eluted in five steps; (step 1-3) addition of buffer A followed by centrifugation, (step 4) addition of buffer B (25 mM Na Acetate, 250 mM NaCl, pH 4.0) followed by centrifugation, (step 5) addition of buffer C (25 mM Na Acetate, 400 mM NaCl, pH 4.0) followed by centrifugation. Total protein concentration of fractions eluted with buffer C was determined using A280 nm measurements.

Example 2

Productive Positions and Combinable Mutations

Productive positions are described above as those positions within a molecule that are most useful for making combinatorial variants exhibiting an improved characteristic, where the position itself allows for at least one combinable mutation. Combinable mutations, as described above, can be described as the substitutions in a molecule that can be used to make combinatorial variants. Combinable mutations are those that improve at least one desired property of the molecule, while not significantly decreasing other properties such as expression, activity, or stability.

Combinable mutations in FveXyn4 were determined using relative performance index (PI) values resulting from the assays described above under "Screening assays": Thermostability I, Thermostability II, Specific activity I, Specific activity II, Pepsin Resistance and protein expression being defined by a minimum of activity in Activity assay I.

Combinable mutations have been grouped according to the following criteria:

Performance index (PI) relative to FveXyn4 parent for specific activity in at least one of the two activity assays I and II is greater than 0.8, PI for Pepsin resistance is greater than 0.9, and PI for Thermostability assay 1 is greater than 1.2. In addition, PI for Activity assay 1 is greater than 0.057 (Group A).

Performance index (PI) relative to FveXyn4 parent for specific activity in at least one of the two activity assays I and II is greater than 0.5, PI for Pepsin resistance is greater than 0.8, and PI for Thermostability assay 1 is greater than 1.2. In addition, PI for Activity assay 1 is greater than 0.057 (Group B).

Performance index (PI) relative to FveXyn4 parent for specific activity in at least one of the two activity assays I and II is greater than 0.9, PI for Pepsin resistance is greater than 0.9, and PI for Thermostability assay 1 is greater than 1.0. In addition, PI for Activity assay 1 is greater than 0.057 (Group C).

Performance index (PI) relative to FveXyn4 parent for specific activity in at least one of the two activity assays I and II is greater than 0.8, PI for Pepsin resistance is greater than 0.9, and PI for Thermostability assay 2 is greater than 1.5. In addition, PI for Activity assay 1 is greater than 0.057 (Group D).

Performance index (PI) relative to FveXyn4 parent for specific activity in at least one of the two activity assays I and II is greater than 0.5, PI for Pepsin resistance is greater than 0.8, and PI for Thermostability assay 2 is greater than 1.5. In addition, PI for Activity assay 1 is greater than 0.057 (Group E).

Performance index (PI) relative to FveXyn4 parent for specific activity in at least one of the two activity assays I and II is greater than 0.5, PI for Pepsin resistance is greater than 0.8, and PI for Thermostability assay 2 is greater than 1.3. In addition, PI for Activity assay 1 is greater than 0.057 (Group F).

Performance index (PI) relative to FveXyn4 parent for specific activity in at least one of the two activity assays I and II is greater than 0.9, PI for Pepsin resistance is greater than 0.9, and PI for Thermostability assay 2 is greater than 1.0. In addition, PI for Activity assay 1 is greater than 0.057 (Group G).

Combinable mutations that fall within groups A, B, C, D, E, F or G will make the variant able to meet at least one of the following criteria for performance a) to c):

a. Relative performance (Performance Index, PI) for specific activity in at least one of the two activity assays I and II is greater than 0.8, PI for Pepsin resistance is greater than 0.9, PI for Expression (Activity assay 1) is greater than 0.057, and PI for Thermostability assay 1 is greater than 1.2 or PI for Thermostability assay 2 is greater than 1.5;

b. Relative performance (Performance Index, PI) for specific activity in at least one of the two activity assays I and II is greater than 0.5, PI for Pepsin resistance is greater than 0.8, PI for Expression (Activity assay 1) is greater than 0.057, and PI for Thermostability assay 1 is greater than 1.2 or PI for Thermostability assay 2 is greater than 1.3;

c. Relative performance (Performance Index, PI) for specific activity in at least one of the two activity assays I and II is greater than 0.9, PI for Pepsin resistance is greater than 0.9, PI for Expression (Activity assay 1) is greater than 0.057, and PI for Thermostability assay 1 is greater than 1.0 or PI for Thermostability assay 2 is greater than 1.0.

Positions represented by at least one combinable mutation in groups A, B, C, D, E, F, or G are productive positions. The Productive positions are assigned a Productivity Score based on the number of amino acid substitutions at a given position that fall within the groups A, B, C, D, E, F, or G using the criteria for determination of Productivity Score set forth below.

The criteria to determine the Productivity Score for productive positions are as follows: Positions where at least 15 out of 20 possible substitutions at a given position fall within groups A, B, C, D, E, F or G are given a Productivity Score of "4". (Table 2.1)

Productive Positions where less than 15, but at least 8 out of 20 possible substitutions at a given position fall within groups A, B, C, D, E, F or G are given a Productivity Score of "3". (Table 2.2)

Productive Positions where less than 8, but at least 4 out of 20 possible substitutions at a given position fall within groups A, B, C, D, E, F or G are given a Productivity Score of "2". (Table 2.3)

Productive Positions where less than 4, but at least 2 out of 20 possible substitutions at a given position fall within groups A, B, C, D, E, F or G are given a Productivity Score of "1". (Table 2.4)

Table 2.1 shows the productive positions in FveXyn4 that fall within the previously described Productivity Score of "4" and the substitutions within those positions that are combinable. Position numbering based on mature FveXyn4 shown in SEQ ID NO: 2.

| POS | Substitutions, FveXyn4 (SEQ ID NO: 2) | Productivity Score |
|---|---|---|
| 135 | W, P, Q, T, D, N, S, R, E, K, C, G, A, M, L, Y, F, I | 4 |

Table 2.2 shows the productive positions in FveXyn4 that fall within the previously described Productivity Score of "3" and the substitutions within those positions that are combinable. Position numbering based on mature FveXyn4 shown in SEQ ID NO: 2.

| POS | Substitutions, FveXyn4 (SEQ ID NO: 2) 1ST | Productivity Score |
|---|---|---|
| 28 | G, M, S, R, Q, T, E, V, I | 3 |
| 57 | S, Q, V, T, R, A, G, E, I, L, C | 3 |
| 62 | N, T, K, Q, S, H, C, F, W | 3 |
| 70 | V, N, E, Q, M, S, H, Y, W | 3 |
| 79 | K, I, L, F, V, Y, K, M, W | 3 |
| 89 | S, G, Q, N, L, D, M, S, E, A, I, V | 3 |
| 102 | A, K, D, P, G, E, T, V, I, C | 3 |
| 105 | T, K, T, F, M, N, D, I, H | 3 |
| 118 | R, H, K, N, Q, W, Y, G, F | 3 |
| 151 | N, K, A, M, Q, H, V, R | 3 |
| 153 | D, S, Q, L, M, I, T, V, Y | 3 |
| 160 | R, Q, M, N, S, T, V, Y | 3 |
| 181 | G, S, P, D, Q, A, K, T, R, H, N | 3 |
| 184 | S, L, Q, I, H, S, M, V, G | 3 |
| 200 | Q, K, R, T, S, H, G, E, I, N, L, D | 3 |
| 220 | Q, K, N, S, A, E, G, T | 3 |
| 232 | G, K, Q, P, R, S, M, L, T, Y, F, W | 3 |
| 262 | P, W, Q, K, N, L, T, I, S, H, V, R | 3 |
| 298 | T, F, W, Y, M, V, I, L, C, T | 3 |

Table 2.3 shows the productive positions in FveXyn4 that fall within the previously described Productivity Score of "2" and the substitutions within those positions that are combinable. Position numbering based on mature FveXyn4 shown in SEQ ID NO: 2.

| POS | Substitutions, FveXyn4 SEQ ID NO: 2) 1ST | Productivity Score |
|---|---|---|
| 4 | D, I, V, P | 2 |
| 21 | I, A, T, C, V | 2 |
| 25 | N, P, D, K, C | 2 |
| 30 | A, P, Q, K | 2 |
| 56 | P, N, G, Q, D | 2 |
| 59 | G, A, S, D, L, F | 2 |
| 64 | G, S, T, Q, D, W, C | 2 |
| 65 | S, G, N, Q, M | 2 |
| 71 | N, D, E, T | 2 |
| 74 | Q, R, N, E | 2 |
| 77 | G, Q, H, N, D, E | 2 |
| 98 | I, V, T, Y | 2 |
| 99 | N, T, Y, G | 2 |
| 100 | D, K, A, V, R, Q | 2 |
| 103 | T, K, M, L, S, H | 2 |
| 104 | L, V, I, F, A | 2 |
| 106 | K, N, T, P, F | 2 |
| 113 | T, R, K, N Q, H | 2 |
| 115 | V, E, L, Q | 2 |
| 117 | G N, V, W, F | 2 |
| 120 | K, P, L, N, G, D | 2 |
| 134 | E, D, G, Q, E | 2 |
| 141 | K, P, Q, S, L | 2 |
| 142 | D, L, C, V | 2 |
| 148 | V, I, M, Q | 2 |
| 150 | G, H, L, W, Y, F | 2 |
| 152 | D, E, N, Q, P, M, W | 2 |
| 156 | G, K, T, R, W | 2 |
| 161 | A, S, M, T, V | 2 |
| 163 | R, M, S, C, V | 2 |
| 167 | P, L, Q, I, F | 2 |
| 176 | Y, H, A, G, D | 2 |
| 180 | S, K, E, D, T | 2 |
| 193 | S, N, R, Y, W | 2 |
| 198 | L, Q, M, K, I | 2 |
| 199 | S, K, T, N, I | 2 |
| 201 | G, T, F, E, M | 2 |
| 202 | V, M, I, T, E, L, Q | 2 |
| 215 | P, K, F, L | 2 |
| 217 | A, P, Q, E, M, D | 2 |
| 227 | A, K, R, Q, I | 2 |
| 229 | A, T, V, N, D | 2 |
| 230 | N, K, Q, G, T | 2 |
| 233 | V, T, Y, S | 2 |

Table 3.4 shows the productive positions in FveXyn4 that fall within the previously described Productivity Score of "1" and the substitutions within those positions that are combinable. Position numbering based on mature FveXyn4 shown in SEQ ID NO: 2.

| POS | Substitutions, FveXyn4 (SEQ ID NO: 2) | Productivity Score |
|---|---|---|
| 3 | A, K, T | 1 |
| 6 | I, Q | 1 |
| 7 | N, D | 1 |
| 11 | K, Q, I | 1 |
| 12 | N, K, H | 1 |
| 16 | L, Q | 1 |
| 18 | Y, F | 1 |
| 29 | V, I | 1 |
| 32 | D, P | 1 |
| 33 | T, V | 1 |
| 37 | K, L, I | 1 |
| 38 | A, T | 1 |
| 52 | D, Q | 1 |
| 53 | A, P, H | 1 |
| 58 | Q, K | 1 |
| 67 | D, Q, G | 1 |
| 72 | F, L | 1 |
| 75 | Q, E, M | 1 |
| 92 | P, H | 1 |
| 93 | Q, T, V | 1 |
| 94 | W, Y | 1 |

-continued

| POS | Substitutions, FveXyn4 (SEQ ID NO: 2) | Productivity Score |
|---|---|---|
| 96 | K, S | 1 |
| 97 | N, T | 1 |
| 107 | V, A, T | 1 |
| 109 | E, Q | 1 |
| 110 | N, D, S | 1 |
| 112 | V, T, L | 1 |
| 114 | Q, K | 1 |
| 116 | V, C, T | 1 |
| 125 | A, G | 1 |
| 129 | V, A, T | 1 |
| 132 | I, P, A | 1 |
| 133 | F, L | 1 |
| 136 | D, C, A | 1 |
| 138 | T, K, I | 1 |
| 139 | L, Q, A | 1 |
| 146 | N, L | 1 |
| 147 | N, D, Q | 1 |
| 149 | F, M | 1 |
| 155 | V, T, A | 1 |
| 159 | F, M | 1 |
| 162 | A, S | 1 |
| 164 | K, V | 1 |
| 168 | N, I, F | 1 |
| 169 | A, T, S | 1 |
| 182 | S, N, K | 1 |
| 183 | A, F, Y | 1 |
| 188 | K, N, Q | 1 |
| 190 | M, V, A | 1 |
| 191 | V, N | 1 |
| 194 | V, T | 1 |
| 196 | K, R, Q | 1 |
| 206 | G, A | 1 |
| 209 | S, L | 1 |
| 211 | T, C, H | 1 |
| 219 | G, P, D | 1 |
| 221 | I, V | 1 |
| 231 | S, P | 1 |
| 235 | E, Q | 1 |
| 236 | V, M | 1 |
| 238 | I, S | 1 |
| 244 | R, K | 1 |
| 249 | N, D, Q | 1 |
| 260 | N, Q, Y | 1 |
| 266 | G, A | 1 |
| 268 | T, F | 1 |
| 269 | V, G, D | 1 |
| 274 | D, G | 1 |
| 296 | A, F, P | 1 |
| 300 | V, P | 1 |
| 302 | N, Q | 1 |
| 304 | L, R | 1 |

Example 3

Combinable Mutations and Suitability Scores

As shown in Example 2, combinable mutations in FveXyn4 were determined using relative performance index (PI) values resulting from the assays described above: Thermostability I, Thermostability II, Specific activity I, Specific activity II, Pepsin Resistance and protein expression being defined by a minimum of activity in Activity assay I.

Combinable mutations were assigned to groups A, B, C, D, E, F or G according to criteria set forth in Example 2. These substitutions are further assigned a Suitability Score based on the group(s) (A, B, C, D, E, F, G) where the substitution appears, and where a higher suitability score represents a substitution more suitable for use in making combinatorial variants. Suitability scores are defined in Table 3.1.

Table 3.1 defines each Suitability Score as it relates to groups of combinable mutations and productive positions in FveXyn4 (SEQ ID NO:2).

| Substitutions appear in Group(s): | Suitability Score |
|---|---|
| A, B, C, D, E, F, and G | 5 |
| A and D | 4 |
| C and G | 3 |
| B and E or (B and F) | 2 |
| B or E | 1 |

Substitutions that appear in groups A, B, C, D, E, F and G will meet the following criteria:

Relative performance (Performance Index, PI) for specific activity in at least one of the two activity assays I and II is greater than 0.9, PI for Pepsin resistance is greater than 0.9, PI for Expression (unstressed activity assay 1) is greater than 0.057, and PI for Thermostability assay 1 is greater than 1.2 and PI for Thermostability assay 2 is greater than 1.5

Substitutions that appear in groups A and D will meet the following criteria:

Relative performance (Performance Index, PI) for specific activity in at least one of the two activity assays I and II is greater than 0.8, PI for Pepsin resistance is greater than 0.9, PI for Expression (unstressed activity assay 1) is greater than 0.057, and PI for Thermostability assay 1 is greater than 1.2 and PI for Thermostability assay 2 is greater than 1.5

Substitutions that appear in groups C and D will meet the following criteria:

Relative performance (Performance Index, PI) for specific activity in at least one of the two activity assays I and II is greater than 0.9, PI for Pepsin resistance is greater than 0.9, PI for Expression (unstressed activity assay 1) is greater than 0.057, and PI for Thermostability assay 1 is greater than 1.0 and PI for Thermostability assay 2 is greater than 1.0

Substitutions that appear in groups B and E, or B and F will meet the following criteria:

Relative performance (Performance Index, PI) for specific activity in at least one of the two activity assays I and II is greater than 0.5, PI for Pepsin resistance is greater than 0.8, PI for Expression (unstressed activity assay 1) is greater than 0.057, and PI for Thermostability assay 1 is greater than 1.2 and PI for Thermostability assay 2 is greater than 1.3

Substitutions that appear in groups B or E will meet the following criteria:

Relative performance (Performance Index, PI) for specific activity in at least one of the two activity assays I and II is greater than 0.5, PI for Pepsin resistance is greater than 0.8, PI for Expression (unstressed activity assay 1) is greater than 0.057, and PI for Thermostability assay 1 is greater than 1.2 or PI for Thermostability assay 2 is greater than 1.5

Suitability scores for individual substitutions of FveXyn4 that fit the above criteria are reported in Table 3.2.

Table 3.2 identifies the Suitability Score of individual substitutions in FveXyn4. Position numbering based on mature FveXyn4 shown in SEQ ID NO: 2

| Substitution | Suitability Score |
|---|---|
| N007D, N025P, D032P, K079F, K079V, A217P, A217Q, A217E, T298F, T298W, T298Y | 5 |
| N007D, I021C, N025P, G028M, A030P, D032P, S065G, K079F, K079V, K079Y, S089G, I132P, W135E, T211C, T211H, A217P, A217Q, A217E, T298F, T298W, T298Y | 4 |
| N007D, N007D, K011Q, I021T, I021V, N025P, G028Q, G028Q, D032P, K037L, S057Q, S057V, S057T, G059S, N062T, N062S, G064T, S065N, N071D, F072L, Q074R, Q075E, G077Q, K079F, K079V, S089N, I098V, A102D, T103M, V107T, E109Q, T113Q, V115E, V115L, V115Q, R118K, I132A, W135D, W135G, W135Y, W135I, L139Q, N147Q, D153S, V155A, S180E, G181P, G181D, G181Q, G181A, A183F, S184L, S184I, M190V, S193Y, L198Q, L198M, S199T, S199I, Q200K, Q200T, V202E, A217P, A217Q, A217E, A217M, A217D, G219P, G219D, Q220K, Q220A, G232Q, V233T, P262N, P262T, G266A, A296F, T298F, T298W, T298Y, V300P | 3 |
| N007D, I021C, N025P, G028M, A030P, D032P, T033V, S065G, F072L, K079I, K079L, K079F, K079V, K079Y, S089G, S089Q, V115E, I132P, W135T, W135D, W135E, D142L, T211C, T211H, A217P, A217Q, A217E, G219P, I221V, V233T, T298F, T298W, T298Y | 2 |
| N007D, K011Q, I021A, I021T, I021C, N025P, G028M, A030P, D032P, T033V, N062T, N062F, G064S, G064T, S065G, S065M, V070N, V070E, V070Q, V070S, F072L, Q074R, Q074E, K079I, K079L, K079F, K079V, K079Y, K079M, S089G, S089Q, S089L, S089M, N099Y, D100V, A102K, A102V, T103K, L104V, L104I, T105K, T105F, V107A, V107T, E109Q, V112T, V112L, T113R, T113K, T113N, V115E, V115L, R118F, K120P, V129A, I132P, I132A, E134D, E134G, W135P, W135Q, W135T, W135D, W135N, W135S, W135R, W135E, W135K, W135C, W135G, W135A, W135M, W135L, D136C, L139Q, D142L, D142V, F149M, G150W, G150Y, N151K, N151M, N151H, N151V, D152N, D152Q, D152P, D152W, D153S, D153I, D153T, V155T, V155A, G156W, F159M, A161V, R163M, R163V, G181A, S193N, S199K, T211C, T211H, A217P, A217Q, A217E, A217M, G219P, Q220K, I221V, A227K, A229T, A229N, A229D, S231P, G232K, G232M, G232L, V233T, E235Q, R244K, N260Q, A296F, T298F, T298W, T298Y, V300P | 1 |

Example 5

This example shows an example of how the different values are calculated and how the conclusions are drawn.

Figure 4:
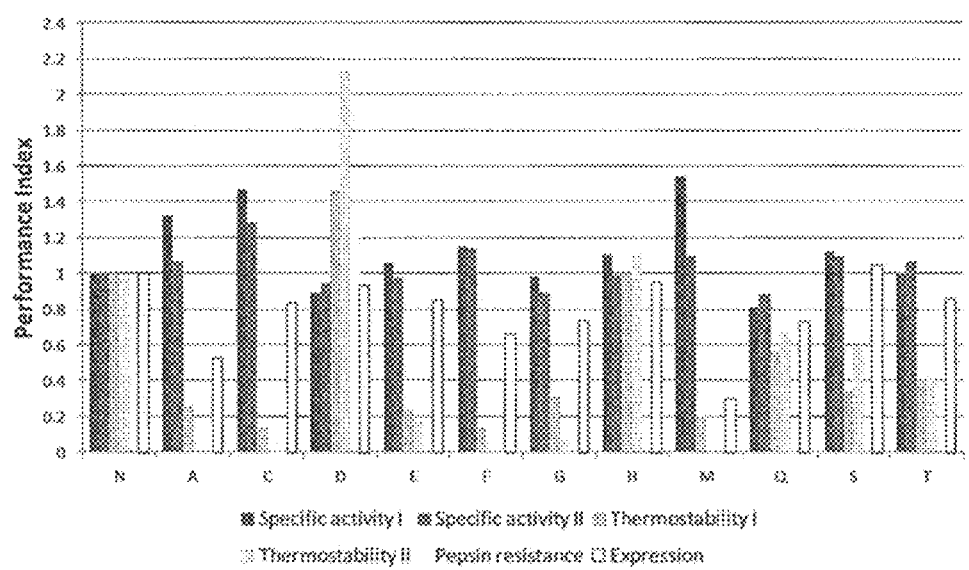
FIG. 4 shows relative Performance Index (PI) values resulting from screening of the variants from the site evaluation library in position 7 of the FveXyn4 mature polypeptide (SEQ ID NO:4)
Figure 24:
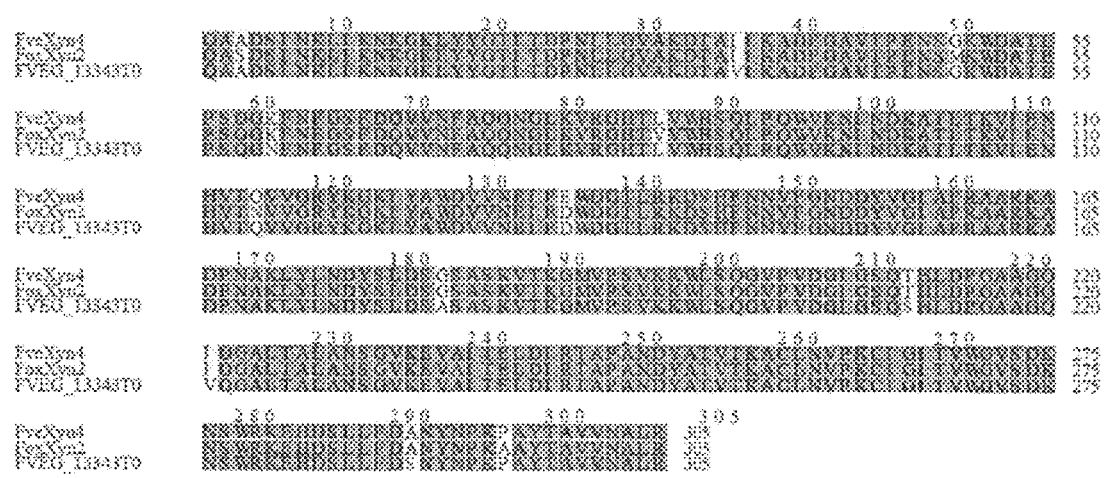
FIG. 24 shows an alignment of the mature proteins for FveXyn4 (SEQ ID NO:2), FoxXyn2 (SEQ ID NO:4) and the xylanase shown herein as SEQ ID NO:16 (FVEG_13343T0).

FIG. 4 shows relative Performance Index (PI) values resulting from screening of the variants from the site evaluation library in position 7 of the FveXyn4 mature polypeptide (SEQ ID NO:2). Data included values for Specific activity I, Specific activity II, Thermostability I, Thermostability II, Pepsin resistance, and Expression. The assays and calculation of the Performance Index values are described above. Substitutions in position 7 where PI for Expression is below 0.057 are not included.

The data in FIG. 4 shows that the substitution N007D makes the variant able to meet the criteria for all the groups A, B, C, D, E, F, and G as defined in Example 2. Therefore this position is given a Suitability score "5", and the substitution N007D makes the variant able to meets the following criteria:

Relative performance (Performance Index, PI) for specific activity in at least one of the two activity assays I and II is greater than 0.9, PI for Pepsin resistance is greater than 0.9, PI for Expression (unstressed activity assay 1) is greater than 0.057, and PI for Thermostability assay 1 is greater than 1.2 and PI for Thermostability assay 2 is greater than 1.5

As only the wild type and N007D, allowing the variant to, meet any of the criteria for groups A, B, C, D, E, F or G, position 007 can only be given Productivity score "1", defined by less than 4, but at least 2 out of 20 possible substitutions fall within groups A, B, C, D, E, F or G.

Conclusively, the N007D substitution makes the variant able to have high PI in both Thermostability I and II, without significant negative influence (PI close to 1) on Specific activity I and II, Pepsin resistance and Expression. Therefore the N007D substitution is very suitable for increasing the thermostability of the FveXyn4 without significantly reducing the specific activity, pepsin resistance and expression.

Example 6

Comparison of FveXyn4 to Related Molecules

A. Identification of Related Molecules by Sequence Analysis.

Homologs were obtained by BLAST search (Altschul S F, Madden T L, Schaffer A A, Zhang J, Zhang Z, Miller W, Lipman D J., 1997). Gapped BLAST and PSI-BLAST: a new generation of protein database search programs. Nucleic Acids Res. 25:3389-402) against the NCBI non-redundant protein database, nr, using the mature protein amino acid sequence for FveXyn4 as the query sequence (SEQ ID NO: 2). Only sequences which have percent identity of 50% or higher were retained. Percent identity (PID) is defined as the number of identical residues divided by the number of aligned residues (length) in the pairwise alignment. Table 6.1 provides the list of sequences which have percent identity of 60% or higher to FveXyn4. The table provides accession numbers to each identified homolog; the identified organism, the length (number of amino acids) of the alignment; and the PID (percent identity).

B. Alignment of Sequences for Homologous Molecules.

The sequences of FveXyn4 and selected homologs were multiply aligned with COBALT software (Papadopoulos, J S. and Agarwala R. (2007), COBALT: Constraint-based alignment tool for multiple protein sequences, Bioinformatics 23:1073-79.) using default parameters: Gap penalties; −11, −1, End-Gap penalties; −5, −1, RPS BLAST enabled, E-value; 0.003 and Max cluster distance; 0.8. For homologous sequences the full region that correspond to seed sequences are shown. Table 6.2 shows the alignment of FveXyn4 and homolog sequences.

TABLE 6.1

List of FveXyn4 Homologs with Percent Identity of 60% or Greater

| Accession Number | Organism | Length | PID (%) |
|---|---|---|---|
| gb\|EGU87360.1\| | Fusarium oxysporum Fo5176 | 305 | 98 |
| gb\|AAC06240.1\| | Fusarium oxysporum f. sp. lycopersici | 305 | 98 |
| ref\|XP_003045671.1\| | Nectria haematococca | 305 | 77 |
| gb\|EKJ71807.1\| | Fusarium pseudograminearum | 305 | 76 |
| ref\|XP_391663.1\| | Gibberella zeae | 305 | 75 |
| gb\|AAT84258.1\| | Gibberella zeae | 305 | 75 |
| ref\|XP_003000315.1\| | Verticillium alboatrum | 304 | 66 |
| gb\|AEN99940.1\| | Chrysosporium lucknowense | 299 | 65 |
| gb\|ABA40421.1\| | Aspergillus fumigatus | 302 | 64 |
| gb\|EFQ33770.1\| | Glomerella graminicola | 305 | 64 |
| gb\|ADM34973.1\| | Penicillium oxalicum | 305 | 64 |
| gb\|ADW66245.1\| | Paecilomyces aerugineus | 305 | 64 |
| sp\|O59859.1\|XYNA_ASPAC | Aspergillus aculeatus | 305 | 64 |
| sp\|C5J411.2\|XYNC_ASPNG | Aspergillus niger | 305 | 64 |
| sp\|Q0H904.2\|XYNC_ASPFU | Aspergillus fumigatus | 325 | 63 |
| gb\|EFQ32887.1\| | Glomerella graminicola | 304 | 63 |
| f\|XP_003714516.1\| | Magnaporthe oryzae | 305 | 63 |
| f\|XP_001271831.1\| | Aspergillus clavatus | 300 | 63 |
| dbj\|BAA92882.1\| | Aspergillus sojae | 304 | 63 |
| sp\|Q96VB6.1\|XYNF3_ASPOR | Aspergillus oryzae | 304 | 63 |
| dbj\|BAG12101.1\| | Penicillium citrinum | 305 | 63 |
| dbj\|BAG12101.1\| | Penicillium citrinum | 305 | 63 |
| sp\|P33559.2\|XYNA_ASPKW | Aspergillus kawachii | 305 | 63 |
| ref\|XP_001267063.1\| | Neosartorya fischeri | 304 | 62 |
| ref\|XP_001267063.1\| | Neosartorya fischeri | 304 | 62 |
| pdb\|1TUX\|A | Thermoascus Aurantiacus | 303 | 62 |
| emb\|CCF41074.1\| | Colletotrichum higginsianum | 306 | 62 |
| sp\|Q0CBM8.2\|XYNC_ASPTN | Aspergillus terreus | 304 | 62 |
| gb\|ABY71931.1\| | Trichoderma pseudokoningii | 312 | 61 |
| sp\|P23360.4\|XYNA THEAU | Thermoascus aurantiacus | 305 | 61 |
| gb\|AAF24127.1\|AF127529 1 | Thermoascus aurantiacus | 305 | 61 |
| gb\|AFD63136.1\| | Aspergillus terreus | 304 | 61 |
| gb\|EJT78966.1\| | Gaeumannomyces graminis | 305 | 61 |
| sp\|Q4JHP5.1\|XYNC_ASPTE | Aspergillus terreus | 304 | 61 |
| pdb\|1\|1W\|A | Thermoascus Aurantiacus | 304 | 61 |
| gb\|EHK21815.1\| | Trichoderma virens | 305 | 60 |

TABLE 6.2

Multiple alignment of FveXyn4 and homolog sequences

```
                                            1         10        20        30        40        50        60
                                            |         |         |         |         |         |         | gi|342887934|gb|EGU87360.1|                 MK-----LSSF----LYT-------------------------------------
gi|2981137|gb|AA006240.1|                   MK-----LSSF----LYT-------------------------------------
gi|408392452|gb|EKJ71807.1|                 MK-----FSSL----LFT-------------------------------------
gi|46135945|ref|XP_391663.1|                MK-----FSSL----LFT-------------------------------------
gi|50844272|gb|AAT84258.1|                  MK-----FSSL----LFT-------------------------------------
gi|302893580|ref|XP_003045671.1|            MK-----FSSF----LFA-------------------------------------
gi|302404956|ref|XP_003000315.1|            MK-----FSQIHIALLIA--PL-------------------------------------
gi|76160900|gb|ABA40421.1|                  MVVLSKLVSSI----LFA-------------------------------------
gi|346979854|gb|EGY23306.1|                 MK-----LSQAHLALLLA--PL-------------------------------------
gi|292495638|sp|Q0H904.2|XYNC_ASPFU         MVVLSKLVSSI----LFV-------------------------------------
gi|310798877|gb|EFQ33770.1|                 MK-----FSMS-LVCLLA--PI-------------------------------------
gi|310797994|gb|EFQ32887.1|                 MK-----FSTS-LVCLLA--PI-------------------------------------
gi|389633727|ref|XP_003714516.1|            MK-----ASSV--LLGLA--PL-------------------------------------
gi|304442663|gb|ADM34973.1|                 MVQIKAAAIAL----IFA-------------------------------------
gi|321150383|gb|ADW66245.1|                 MVQIKAAAIAL----IFA-------------------------------------
gi|121707433|ref|XP_001271831.1|            MVVLSKIFSCA----LFL-------------------------------------
gi|292495637|sp|B0Y6E0.2|XYNC_ASPFC         MVVLSKLVSSI----LFV-------------------------------------
gi|7328942|dbj|BAA92B82.1|                  MVHLKSLAGIL----LYT-------------------------------------
```

TABLE 6.2-continued

Multiple alignment of FveXyn4 and homolog sequences

```
                                          1         10        20        30        40        50        60
                                          |         |         |         |         |         |         | gi|74664704|sp|Q96VB6.1|XYNF3_ASPOR       MVHLKSLAGIL----LYT---------------------------------------
gi|165906534|gb|ABY71931.1|               MK-----ANV--ILCLLA--PLIA-------------------------ALPTEPIP
gi|169159203|dbj|BAG12101.1|              MVQIKMAALAA----LFA---------------------------------------
gi|119500612|ref|XP_001267063.1|          MVVLSKLISSI----LFA---------------------------------------
gi|402083948|gb|EJT78966.1|               MR-----GLFA--LL-LL--PL-----------------------------------
gi|121818962|sp|Q4JHP5.1|XYNC_ASPTE       MVRLTVLAGFL----LTS---------------------------------------
gi|292495633|sp|Q0CBM8.2|XYNC_ASPTN       MVALTVLAGFL----LTS---------------------------------------
gi|6690415|gb|AAF24127.1|AF127529_1       MVRPTILLTSL-LLAPFA---------------------------------------
gi|380719871|gb|AFD63136.1|               MVRLTVLAGFL----LTS---------------------------------------
gi|345505465|gb|AEN99940.11               MRTLTFVLAAA-PVAVLAQSPLWGQCGGQGWTGPTTCVSGAVCQFVNDWYSQCVPGSSNP
gi|157634036|pdb|1TUX|A                   ---------------------------------------------------------
gi|380482707|emb|CCF41034.1|              MK-----FFSE-R--RLP--PG-----------------------------------
gi|13432255|sp|P23360.4|XYNA_THEAU        MVRPTILLTSL-LLAPFA---------------------------------------
gi|3915310|sp|O59859.1|XYNA_ASPAC         MVQIKAAALAV----LFA---------------------------------------
gi|28373360|pdb|1I1W|A                    ---------------------------------------------------------
gi|358384163|gb|EHK21815.1|               MK-----ANV--IFCLLA--PLVA-------------------------ALPTEFIQ
gi|292495278|sp|A2QFV7.1|XYNC_ASPNC       MVQIKVAALAM----LFA---------------------------------------
gi|292495635|sp|C5J411.2|XYNC_ASPNG       MVQIKVAALAM----LFA---------------------------------------
gi|342887934|gb|EGU87360.1|               -----ASLVAAIPT---AIEPRQASDSINKLIKNKGKLYYGTITDPNLLGVAKDT-AIIK
gi|2981137|gb|AAC06240.1|                 -----ASLVAAIPT---AIEPRQASDSINKLIKNKGKLYYCTITDPNLLGVAKDT-AIIK
gi|408392452|gb|EKJ71807.1|               -----ASLVAAMPA---SIEPRQAQNSINKLIKNKGKLYYGTITDPNLLQSQQNN-AIIK
gi|46139945|ref|XP_391663.1|              -----ASLVAAMRA---SIEPRQAQESINKLIKAKCKLYYGTITDPNLLQSQQNN-AVIK
gi|50844272|gb|AAT84258.1|                -----ASLVAAMPA---SIEPRQAQESINKLIKAKGKLYYSTITDPNLLQSQQNN-AVIK
gi|302893580|ref|XP_003045671.1|          -----ASLVAAAPA---NVEPRQSPNSINKLIINKGKKYYGTITDPNLLSNQKNN-AIIK
gi|302404956|ref|XP_003000315.1|          -----AAVASPVPEAASHVESRQAAASIDKLFKAKGKLYIGVATDRGLLQTGKNA-AIIQ
gi|76160900|gb|ABA40421.1|                -----SLVSAGV------IEEERQA-ASINQAFTSHGKRYFGTASDQALLQKSQNE-AIVR
gi|846919854|gb|EGY23306.1|               -----AAVASPVPEAASHVEPRQAATSIDRLFKAKGKLYIGVATDRGLLQTGKNA-AIIQ
gi|292495638|sp|Q0H904.2|XYNC_ASPFU       -----SLVSAGV------IEEERQA-ASINQAFTSHGRKYFGTASDQALLQKSQNE-AIVR
gi|810798877|gb|EFQ33770.1|               -----TVLAAPLEG---GLEQRQAAQSVDRLINAKGRKYFGTCSDOGRLTSGKNA-AIIN
gi|310797994|gb|EFQ32887.1|               -----TALAAPI-------EERQASQSIDKLFKAKGKQYYGNIADPNLINNAKNA-AILK
gi|889633727|ref|XP_003714516.1|          -----AALAAPTPE-A-ELSARQAQQSIDALMKAKGKLYFGTATDOGLLNTGKNS-AIIK
gi|304442663|gb|ADM34973.1|               -----GSAIAAPAE---TLESRQAATSIDAKFKAEGKKYFGNIADQYTLIKSRKPAAIIK
gi|321150383|gb|ADW66245.1|               -----GSAIAAPAE---TLESROAATSIDAKFKAHGKKYFCNIADQYTLTKSPKPAAIIK
gi|121707433|ref|XP_001271831.1|          -----SLGSAAA------IDIRQT-SSINNAFKSHGKKYEGTCGDQNTLSIPQNS-AIIK
gi|292495637|sp|B0Y6E0.2|XYNC_ASPFC       -----SLVSAGV------IFERQA-ASINQAFTSHGKKYFGTASDQALLQKSQNE-AIVR
gi|7328942|dbj|BAA92882.1|                --------SLCI------ASSQQAPASINNAEVTKGKKYEGICADQGTLSDGTNS-GIIK
gi|74664704|sp|Q96VB6.1|XYNF3_ASPOR       --------SLCI------ASSQQAPASINNAFVAKGKKYFCICADQGTLSDGTNS-GIIK
```

TABLE 6.2-continued

Multiple alignment of FveXyn4 and homolog sequences

```
                                        1         10        20        30        40        50        60
                                        |         |         |         |         |         |         | gi|165906534|gb|ABY71931.1|             LDPELAALRANLTERTPDLWDRQAAQSIDQLIKRRGKLYEGTATDRGLLQREKNA-AIIQ
gi|169159203|dbj|BAG12101.1|             -----GQVLSTP------LEPRQASVSIDAKFKAHCKKYFCNIGEQYTENRNAKTPAIIK
gi|119500612|ref|XP_001267063.1|         -----SLVSAAV------IE-RQA-TSINQAFTSHGKKYEGTASDQRLLQNSQNE-AIVR
gi|402083948|gb|EJT78966.1|              -----A-LAAPTPE-ACELVERQAAQSIDRLMKAKGKLYYGTATDQGRLGQGKNA-AVIQ
gi|121818962|sp|Q4JHP5.1|XYNC_ASPTE      -----AACSACV------IGERQAASSINNAFKAKGKKITGICGDOGILSDSTNS-AIVK
gi|292495633|sp|Q0CBM8.2|XYNC_ASPTN      -----AACSACV------IGERQAAASINNAFKAKGKKYFGTCGDOGTLSDSTNS-AIVK
gi|6690415|gb|AAF24127.1|AF127529_1      -----A---ASPI-----LEERQAASVDQLIKARGKVYFGVATDQNRLITG-KNAAIIQ
gi|380719871|gb|AFD63136.1|              -----AACSACV------ICFROAAASINNAFKAKGKKYFGTCGDQGTLSDSTNS-AIVK
gi|345505465|gb|AEN99940.1|              PTGITSSITGSTPA---PTGGGGSGTGLHDKFKAKGKLYEGTEIDHYHLNNNALT-NIVK
gi|157834036|pdb|1TUX|A                  ---------------------AAAQSVDQLIDARGKVYFGVATDQNRLTTG-KNAAIIQ
gi|380482707|emb|CCF41074.1|             -----GPTHRPSRR---PSEERQASQSIDRLIKAKGKQYYGTCSDQCRLTSGRNA-DIIK
gi|13432255|sp|P23360.4|XYNA_THEAU       -----A---ASPI-----LEPRQAAQSVDQLIKARCKVYFGVATDQNRLTIC-KNAAIIQ
gi|3915310|sp|O59859.1|XYNA_ASPAC        -----SNVLANP------IEPRQASVSIDAKFKAHGRKYLGTIGDQYTLNKNAKTPAIIK
gi|28373360|pdb|1I1W|A                   ---------------------XAAQSVDQLIKARGKVYEGVATDQNRLTTG-KNAAIIQ
gi|358384163|gb|EHK21815.1|              LEPNLAARRVNITERMADLEDRQASVSIDQLFKKKGKVYFGTATDRGLLQRERNA-AIIQ
gi|292495278|sp|A2QFV7.1|XYNC_ASPNC      -----SQVLSEP------IEPRQASVSIDTKFKAHGKKYLGNICDQYTLTKNSKTPAIIK
gi|292495635|sp|C5J411.2|XYNC_ASPNG      -----SQVLSEP------IDPRQASVSIDTKFKAHGKKYLGNIGDQYTLTKNSKTPATTK
gi|342887934|gb|EGU87360.1|              ADF-GAVTPENSGKWDATEPSQGKFNFGSFDQVVNFAQQNGLKVRGHTLVWKSQLPQWVK
gi|2981137|gb|AAC06240.1|                ADF-GAVTPENSMKWDATEPSQGKENFGSEDQVVNFAQQNGLKVRGHTVVWHSQLPQWVK
gi|408392452|gb|EKJ71807.1|              ADF-GQVITENSMKWDATEPQQGKFNFGGGDQVVNFASQNGLKVRGHALVWHLQLPQWVH
gi|46139945|ref|XP_391663.1|             ADF-GQVTPENSMKWDATEPQQGKENFGGGDQVVNFAAQNGLKVRGRALVWHSQLPQWVH
gi|50844272|gb|AAT84258.1|               ADF-GQVTPENSMKWDATEPQQNKFNFGGGDQVVNEASQNCLKVRGHALVWKSQLPQWVH
gi|302893580|ref|XP_003045671.1|         ANF-GQVTAENSMKWDATEPQRGQFNFAGADQVVNFAQQNGLKVRGHTLLWHSQLPQWVQ
gi|302404956|ref|XP_003000315.1|         QDF-GQVIPENSMKWDALEPSRGSFNFAGADFLVDWAQINSKSIRGHTLVWKSQLPQWVK
gi|76160900|gb|ABA40421.1|               KDF-GQLTPENSMKWDATEPSQGRFNFAGADFLVNYAKQNGKKVRGHTLVWKSQLPSWVS
gi|346979854|gb|EGY23306.1|              QDF-GQVIPENSMKWDALEPSRGSFSFAGADFLVDWAQINSKSIRGHTLVWKSQLPQWVK
gi|292495638|sp|Q0H904.2|XYNC_ASPFU      KDF-GQLTPENSMKWDATEPSQGRENFAGADFLVNYAKQNGKKVRGHTLVWHSQLPSWVS
gi|310798877|gb|EFQ33770.1|              ADF-GQLTPENSMKWDQIQPNNGQFNWAGADYLVNFAQQNCKLVRGHTLVWHSQLASYVQ
gi|310797994|gb|EFQ32887.1|              ADE-GVLIPENSMKWQSIEPTQGKENWAGADALVDEATKNGQKVRGHTLVWHSQLASYVS
gi|389633727|ref|XP_003714516.1|         ADF-GQVIPENSMKWQSLENIRCQYNWAPADALVNFAVSNNKSIRGHTLIWKSQLPGWVN
gi|304442663|gb|ADM34973.1|              ADE-GQLIPENSMKWDATEPSRGKFNEGGSDYLVNFATQNNKMIRGHTLVWHSQLPQWVQ
gi|321150383|gb|ADW66245.1|              ADF-GQLTPENSMKWDATEPSRGKENFCGSDYLVNFATQNNKMIRGHTLVWHSQLPQWVQ
gi|121707433|ref|XP_001271831.1|         ADE-GALTPENSMKWDATEPSRGKENFAGADHLVNYAKQNGKLVRGHTLVWYSQLPAWVK
gi|292495637|sp|B0Y6E0.2|XYNC_ASPFC      KDF-GQLTPENSMKWDATEPSQGRFNFAGADFLVNYAKQNGKKVRGHTLVWHSQLPSWVS
gi|7328942|dbj|BAA92882.1|               ADE-GQLTPENSMKWDATEPSQGKFSESGADYLVNYAATNNKLIRGHTLVWHSQLPSWVQ
gi|74664704|sp|Q96VB6.1|XYNF3_ASPOR      ADE-GQLTPENSMKWDATEPSQGKFSFSGADYLVNYAATNNKLIRGHTLVWHSQLPSWVQ
gi|165900534|gb|ABY71931.1|              ADL-GQVTPENSMKWQSLENNQGQYNWGDADYLVNFAQQNGKLIRGHTLIWHSQLPAWVN
gi|169159203|dbj|BAG12101.1|             ADE-GQITPENSMKWDATEENQGQFSFSGSDYLVNFAQSNGKLIRGHTLVWHSQLPSWVS
```

TABLE 6.2-continued

Multiple alignment of FveXyn4 and homolog sequences

```
                                           1         10        20        30        40        50        60
                                           |         |         |         |         |         |         | gi|119500612|ref|XP_001267063.1|           KDF-GQLTPENSMKWDATEPSRGSFNFAGADELVNYAKQNGMRVRCHTLVWHSQLPSWVS
gi|402083948|gb|EJT78966.11                GNE-GQVTPENSMKWESIERSKGQYNWGQADYLVDWATKNDKSIRGHTLVWHSQLPGWVS
gi|121818962|sp|Q4JHP5.1|XYNC_ASPTE        ADE-GQLTPENSMKWDATEPNRGQFSFGGADYLVNYAASNGKMIRCHTLVWHSQLPGWVQ
gi|292495633|sp|Q0CBM8.2|XYNC_ASPTN        ADF-GQLTPENSMKWDATEPNRGQFSFGGADYLVNYATSNGKMIRGHTLVWHSQLPGWVQ
gi|6690415|gb|AAF24127.1|AF127529_1        ADF-GQVTPENSMKWDATEPSQGNFNFAGADYLVNWAQQNGKLIRGHTLVKHSQLPSWVS
gi|380719871|gb|AFD63136.1|                ADF-GQLTPENNMKWDATEPNRGQFSEGGADYLVNYATSNGKMIRGHTLVWESQLPGWVQ
gi|345505465|gb|AEN99940.1|                KDF-GQVTHENSLKWDATEPSRNQFNEANADAVVNFAQANGKLIRGHTLLWHSQLPQWVQ
gi|157834036|pdb|1TUX|A                    ADF-GQVTPENSMKWDATEPSQGNFNFAGADYLVNWAQQNGKLIRGHTLVKHSQLPSWVV
gi|380482707|emb|CCF41074.1|               ANFRAQITPENSMKWDQIEPSRGQFNWAGPDYLVEFAQKNGKLVRGHTLVWHSQLAGWVN
gi|13432255|sp|P23360.4|XYNA_THEAU         ADF-GQVTPENSMKWDATEPSQGNENEAGADYLVNWAQQNGKLIRGHTLVWHSQLPSWVS
gi|3915310|sp|O59859.1|XYNA_ASPAC          ADE-GQLTPENSMKWDATEPNRGQFSESGSDYLVNFAQSNGKLIRGHTLVWHSQLPSWVQ
gi|28373360|pdb|1I1W|A                     ANF-GQVTPENSMKNDATEPSQGNFNFAGADYLVNWAQQNGKLIRGHTLVWHSQLPSWVS
gi|358384163|gb|EHK21815.1|                ANE-GQVTPENSMKWQSLNPNQGQYNNADADYLVNFAQQNGKTIRGHTLVWHSQLPSWVN
gi|292495278|sp|A2QFV7.1|XYNC_ASPNC        ADF-GALTPENSMKWDATEPSRGQFSFGSDYLVNFAQSNNKLIRGHTLVWHSQLPSWVQ
gi|292495635|sp|C5J411.2|XYNC_ASPNC        ADF-GALTPENSMKWDATEPSEGQFSFGSDYLVNFAQSNNKLIRGHTLVWHSQLPSWVQ
gi|342887934|gb|EGU87360.1|                NINDKATLTKVIENHVTNVVGRYKGKIYANDVVNEI--------FDWDGSLRKDSHFNNV
gi|2981137|gb|AAC06240.1|                  NINDKATLTKVIENHVTNVVGRYKGKIYAWDVVNEI--------FDWDGTLARDSHFNNV
gi|408392452|gb|EKJ71807.1|                VIRDKTQMKNAIENHIKNVAGHEKGRVYAWDVLNEI--------EDWDGSLRKDSPFTQV
gi|46139945|ref|XP_391663.1|               NIKDKTQMKNAIENHIKYVAGHEKGKVYANDVLNEI--------ETWEGSLRKDSPFTQV
gi|50844272|gb|AAT84258.1|                 NIKDKTQMKNAIENHIKNVAGHFKGRVYAWDVINEI--------FDWDGSLAKDSPFTQV
gi|302893580|ref|XP_003045671.1|           SINDRNTLTQVIENHIKTVAGRYKGKIYAWDVVNEI--------FEWSGRLR-DSVFSRV
gi|302404956|ref|XP_003000315.1|           DIKDRDDLINVIENHVKTIVTRYKGKIRAWDVVNEI--------FNEDGTMR-SSVFSDI
gi|76160900|gb|ABA40421.1|                 ATSDKNTLTSVLKNHITTVMTRYKGQIYANDVVNEI--------FNEDGSLR-DSVFSRV
gi|346979854|gb|EGY23306.1|                DIKDRDDLTTVISNHVKTIVTRYKGKIRAWDVVNEI--------FNEDGTMR-SSVESDV
gi|292495638|sp|Q0H904.2|XYNC_ASPFU        AISDKNTLTSVLKNHITTVMTRYKGQIYAWDVVNEI--------FNEDGSLR-DSVFSRV
gi|310798877|gb|EFQ33770.1|                NIRDKATLTKTIQDHISAVVGRYKGKIYAWDVVNEI--------FDESGNLR-SSVESQV
gi|310797994|gb|EFQ32887.1|                NIKDKATLTKAIFEHISAVVGRYKGKIMHWDVVNEM--------FNEDGSLR-PSVFSNV
gi|389633727|ref|XP_003714526.1|           NINDRNQLTTVIQNHVATVEGRWRGKIRAWDVVNEI--------FNEDGTMR-QSVFSRV
gi|304442663|gb|ADM34973.1|                NINDRNTLTQVLKDHITNVMGRYKGKIYAWDVVNEI--------FNEDGSLR-NSVFYRV
gi|1321150383|gb|ADW66245.1|               NINDRNTLTQVLKDHITNVMGRYKGKIYAWDVVNEI--------FNEDGSLR-NSVFYRV
gi|121707433|ref|XP_001271831.1|           AISDKqtLTSVLKNHITTVMSRYKGQVYANDVVNEI--------FEENGSLR-NSVFYRV
gi|292495637|sp|B0Y6E0.2|XYNC_ASPFC        AISDKNTLTSVLKNHITTVMTRYKGQIYANDVVNEI--------FNEDGSLR-DSVFSRV
gi|7328942|dbj|BAA92882.1|                 GITDKNTLTSVLKNHITTVMNRYKGRVYAWDVVNEI--------FNEDGTLR-SSVFYKV
gi|74664704|sp|Q96VB6.1|XYNF3_ASPOR        GITDKNTLTSVLKNHITTVMNRYKGKVYAWDVVNEI--------FNEDGTLR-SSVFYNV
gi|165906534|gb|ABY71931.1|                NINNADTLRQVIRTHVSTVVGRYKGKIRAWDVVNEIFNEDGTIVFNEDGTLR-SSVFSRL
gi|169159203|dbj|BAG12101.1|               SISDKNTLINVMKNHITTVMNRYKGKIYAWDVVNEI--------FNEDGSLR-DSVFSRV
gi|119500612|ref|XP_001267063.1|           AITDKNTLTSVLKNEITTVMTRYKGQIYHWDVVNEI--------FNEDGSLR-DSVFSRV
```

TABLE 6.2-continued

Multiple alignment of FveXyn4 and homolog sequences

```
                                         1         10        20        30        40        50        60
                                         |         |         |         |         |         |         | gi|402083948|gb|EJT78966.1|              NINNKAELTKVIQDHVAAVVGRYKGKIRAWDVLNEI--------FNEDGSLR-SSVFSRV
gi|121818962|sp|Q4JHP5.1|XYNC_ASPTE      GITDKNTLTSVLRNHITTVMQRYKGKVYAWDVVNEI--------FNEDGSLR-KSVFYNV
gi|292495633|sp|Q0CBM8.2|XYNC_ASPTN      GITDKNTLTSVLRNHITTVMQRYNGKIYANDVVNEI--------FNEDGSLR-KSVFYNV
gi|6690415|gb|AAF24127.1|AF127529_1      SITDKNTLTNVMKNHITTLMTRYRGKIRAWDVVNEA--------FNEDGSLR-QTVELNV
gi|380719871|gb|AFD63136.1|              GITDKNTLTSTERNHITTVMQRYKGKIYANDVVNEI--------FNEDGSLR-KSVFYNV
gi|345505465|gb|AEN99940.1|              NINDRNTLTQVIENHVTTLVTRYKGKILHWDVVNEI--------FAEDGSLR-DSVFSRV
gi|157834036|pdb|1TUX|A                  SITDKNTLTNVMENHITTIMTRYIGKIRAWDVVNEA--------FNEDGSLR-QTVFNNV
gi|360482707|emb|CCF41074.1|             NVADRAGLTQVIESHIKAIVGRYKGKIYHWDVVNEI--------FNEDGSLR-SSVFSQV
gi|13432255|sp|P23360.4|XYNA_THEAU       SITDKNTLTNVMKNHITTLMTRYKGKIRAWDVVNEA--------FNEDGSLR-QTVFLNV
gi|3915310|sp|O59859.1|XYNA_ASPAC        STYDRGTLIQVMQNHIATVMQRYKGKVYAWDVVNEI--------FNEDGSLR-QSHFYNV
gi|28373360|pdb|1I1W|A                   SITDKNTLTNVMKNHITTLMTRYKGKIRAWDVVNEA--------FNEDGSLR-QTVFLNV
gi|358384163|gb|EHK21815.1|              NINNADTLRQVIRTHVLTVVGRYKGKIRAWDVVNEI--------FNEDGTLR-SSVFSRL
gi|292495278|sp|A2QFV7.1|XYNC_ASPNC      SITDKNTLIEVMKNHITTVMQHYKGKIYAWDVVNEI--------FNEDGSLR-DSVFYKV
gi|292495635|sp|C5J411.2|XYNC_ASPNG      SITDKNTLIEVMKNHITTVMQHYKGKIYAWDVVNEI--------FNEDGSIR-DSVEYKV
gi|342887934|gb|EGU87360.1|              FGNDDYVGIAFRAARKADPNAKLYINDYSLDSGSASKVTKGMVPSVKKWLSQGVPVDGIG
gi|2981137|gb|AAC06240.1|                FGNDDYVGIAFRAARKADPNAKLYINDYSIDSGSASKVTKGMVPSVKKWLSQGVPVDGIG
gi|408392452|gb|EKJ71807.1|              LG-EEFVGIAFRAARAADPNAKLYINDYSIDDPNAAELKAGMVAHVKKWVSQGIFIDGIG
gi|46139945|ref|XP_391663.1|             LG-EEFVGIAFRAARAADPNAKLYINDYSIDDPNAAKLKAGMVAHVKKWVSQGIPIDGIG
gi|50844272|gb|AAT84258.1|               LG-EEFVGIAERAARAADPNAKLYINDYSIDDPNAARLKAGMVAHVKKWVSQGIPIDGIG
gi|302893580|ref|XP_003045671.1|         LG-EDFVGIAFRAARAADPNAKLYINDYSLDSANAAKVTTGMVAHVKKWIAAGIPIDGIG
gi|302404956|ref|XP_003000315.1|         LG-EDFVGIAFRAARAADPNAKLYINDINLDRANYKV-NGLVSKVEKWITAGVPIDGIG
gi|76160900|gb|ABA40421.1|               LG-EDFVRTAFETARSVDPSAKLYINDYNLDSASYGK-TQGMVRCVKKWLAAGIPIDGIG
gi|346979854|gb|EGY23306.1|              LG-EDFVGIAFRAARAADPNAKLYINDYLDRANYKV-NGLVSKVEKWITAGVPIDGIG
gi|292495638|sp|Q0H904.2|XYNC_ASPFU      LG-EDFVRIAFETARSVDPSAKLYINDYNLDSASYGK-TQGMVRYVKKWIAAGTPIDGIG
gi|310798877|gb|EFQ33770.1|              LG-EDFVGIAFRAARAADPNAKLYINDYNLDQASYAKT-QAMARKVKQWIGQGIPIDGIG
gi|310797994|gb|FFQ32867.1|              LG-EDFVRIAFKAAKAADPNALLFINDFNLDSANSAKT-KAMANKVKQWIAQGIPTDGIG
gi|389633727|ref|XP_003714516.1|         LG-EDFVRIAFEAARKADPNAKLYINDYNLDSPNAAKLTKGMVAHVKKWLAAGVPIDGIG
gi|304442663|gb|ADM34973.1|              LG-EDFVRIAFETARATDPNAKLYINDYNLDNANYGR-TKGMISHVKKWISQGIPIDGIG
gi|321150383|gb|ADW66245.1|              LG-EDFVRIAFETAKATDPNAKLYINDYNLDNANIGK-TKGMISHVKKWISQGIPIDGIG
gi|121707433|ref|XP_001271831.1|         LG-FDFVRIAFFTARAVDPHAKLYINDYNLDSANIGK-TQAMVKHVKKWLAAGIPIDGIG
gi|292495637|sp|B0Y6E0.2|XYNC_ASPFC      LG-EDFVRIAFETARSVDPSAKLYINDYNLDSASYGK-TQGMVRYVKKWLAAGIPIDGIG
gi|7323942|dbj|BAA92882.1|               LG-EDFVRIAFFAARAADPOAKLYINDYNLDSANYCK-TTGLANHVKKWIAQGIPIDGIO
gi|74664704|sp|Q96VB6.1|XYNF3_ASPOR      LG-EDFVRIAFETARAADPQAKLYINDYNLDSANIGK-TTGLANHVKKWIAQGIPIDGIG
gi|165906534|gb|ABY71931.1|              LG-EEFVSIAFRAARDADPSARLYINDYNLDSATIGKV-NGLKSYVSKWISQGVPIDGIG
gi|169159203|dbj|BAG12101.1|             IG-EDFVRIAFETARAADPNAKLYINDYNLDSASYSK-VNGMVSKVKKWIAAGIPIDGIG
gi|119500612|ref|XP_001267063.1|         LG-EDFVRIAFETARSVDPSAKLYINDYNLDSASYGK-TQGMVSHVKKWLAAGIPIDGIG
gi|402083948|gb|EJT78966.1|              LG-FDFVRITFEAARKADPDAVLYINDYNLDSPNAAKLTRGMVANVKKWISOGIPIDGIG
gi|121818962|sp|Q4JHP5.1|XYNC_ASPTE      LG-EDFVRIAFETARSVDPQAKLYINDYNLDNANYAK-TKGMADHVRKWISQGIPIDGIG
```

TABLE 6.2-continued

Multiple alignment of FveXyn4 and homolog sequences

```
                                            1         10        20        30        40        50        60
                                            |         |         |         |         |         |         |
gi|292495633|sp|Q0CBM8.2|XYNC_ASPTN         LG-FDFVRIAITTARSVDPQAKLYINDYNLDNANYAK-TKGMADHVRKWISQGIPTDGIG
gi|6690415|gb|AAF24127.1|AF127529_1         IG-EDYIPIAFQTARAADPNAHLYINDYNLDSASYPK-TQATVERVKQWRAAGVPIDGIG
gi|380719871|gb|AFD63136.1|                 LG-FDFVRIAFFTARSVDPQAKLYINDYNLDNANCAK-TKSMADHVREWTSOGIPIDGIG
gi|345505465|gb|AEN99940.1|                 IG-EDFVGIAFRAAHAADPNAKLYINDYNLDIANYAKVTRGEVEKVNKKIAQGIPIDGIG
gi|157834036|pdb|1TUX|A                     IG-FDYIPTAFRTARAADPNAKLYINDYNLDSASKPK-TSAIVKRVYKWRAAGVPIDGIG
gi|360482707|emb|CCF41074.1|                LG-EDFVGIAFRAARAADPNAKLYINDYNLDQASYAKT-QAMARKVKEWIGKGIPIYGIG
gi|13432255|sp|P23360.4|XYNA_THEAU          IG-EDYIPTAFQTARAADPNAKLYINDYNLDSASIPK-TQAFVNRVKQWRAAGVPIDGIG
gi|3915310|sp|O59859.1|XYNA_ASPAC           IG-EDYVRIARETARAVDPNAKLYINDYNLDSASYPK-LTGLVNHVEKWVAAGVPIDGIG
gi|28373360|pdb|1I1W|A                      IG-EDYIPTAFQTARAADPNAKLYINDYNLDSASIPK-TQAIVERVKKWRAAGVPIDGIG
gi|358384163|gb|EHK21815.1|                 LG-EEFVSTAFRAAREADPSCRLYINDYNLDRAGSSKV-NLMRYYVDKWISQGVPIDGIG
gi|292495276|sp|A2QFV7.1|XYNC_ASPNC         IG-EDYVRTAFFTARAADPNAKLYINDYNLDSASYPK-LTGMVSHVKKWIAAGIPIDGIG
gi|292495635|sp|C5J411.2|XYNC_ASPNG         IG-EDYVRTAFETARAADPNAKLYINDYNLDSASYSK-LTGMVSHVKKWIAAGIPIDGIG
gi|342887934|gb|EGU87360.1|                 SQTHLDPGAA----GQIQGALTAIANSGVKEVATTELDIRTAPANDIATVTKACLNVPKC
gi|2981137|gb|AAC06240.1|                   SQTHLDPGAA----GQI0GALTAL8NSGVKEVAITELDIRTAPANDYATVTKACLNVEKC
gi|408392452|gb|EKJ71807.1|                 SQTHLDPGAA----NGVQAALQQMASTGVKEVAITELDIRSAPAADIATVTKACINVPKC
gi|46139945|ref|XP_391663.1|                SQTHLDPGAA----NGVQAAL0QMASTGVKFVAITEL0IRSAPAADYNEVIKAGLNVPRC
gi|50844272|gb|AAT84258.1|                  SQTHLDPGAA----NGVQAALQQMASTGVKEVAITELDIRSAPAADIATVTKACLNVPKC
gi|302893580|ref|XP_003045671.1|            SQTHLDPGAA----SGIQGALQALAGSGVSEVATTELDIASAPANDIATVTKACLNVPKC
gi|302404956|ref|XP_003000315.1|            SQTHLDAGAA----GNIKGVLQQLASAQVSEVATTELDIKTAPAADFATIVGACLDVPKC
gi|76160900|gb|ABA40421.1|                  TQTHLGAGAS----SSVKGALTALASSGVSEVAITELDIAGASSQDYVNVVKACLDVPKC
gi|346979854|gb|EGY23306.1|                 SQTHLDAGAA----GNIKGVLQQLASTQVSEVATTELDIKMAPAADFATVVGACLDVPKC
gi|292495638|sp|Q0H904.2|XYNC_ASPFU         TQTHLGAGAS----SSVKGALTALASSGVSEVAITELDIAGASSQDYVNVVKACLDVPKC
gi|310798877|gb|EFQ33770.1|                 SQAHLQANQG----GNALGALQTLAGSGVKEVAITELDIVGASSNDYSAVTRACLQVPQC
gi|310797994|gb|EFQ32887.1|                 SQTHLNPGQA----AGVAGALKTLASSGVKHVAITELDIAGANPNDYSTVTKACLDLPQC
gi|389633727|ref|XP_003714516.1|            SQGHLQSG0G----NGLAQAIKALADSGVKEVAVTELDIQGNNANDYAAVTKGCLAVPAC
gi|304442663|gb|ADM34973.1|                 SQSHLEAGMG----AGVSAALNALATAGTKEVAITELDIAGASSTDYVNVAKACLNQPKC
gi|321150383|gb|ADW66245.1|                 SQSHLEAGMG----AGVSAALNALATAGTKEVAITELDIAGASSTDYVNVAKACLNQPKC
gi|121707433|ref|XP_001271831.1|            SQSHL-----------SQALSALASTGVSEIAITELDIKGANFSEYVAVTEACLEVKKC
gi|292495637|sp|B0Y6E0.2|XYNC_ASPFC         TQTHL-----------GALTALASSGVSEVAITELDIAGASSODYVNVVKACIBVPKC
gi|7326942|dbj|BAA92882.1|                  SQTHLSAGGS----SGVKGALNILARSGVSEVATTELDIAGASSNDIVNVVKACLEVSKC
gi|74664704|sp|Q96VB6.1|XYNF3_ASPOR         SQTELSAGGS----SGVKGALNTLAASGVSEVATTELDTAGASSNDYVNVEACLEVSKC
gi|165906534|gb|ABY71931.1|                 SQTHLSPGGA----SGTLGALQQLATVPVTEVAITELDIQGAPTNDITQVVQACLNVSKC
gi|169159203|dbj|BAG12101.1|                SQTELGAGAG----SAVSGALNALASAGTKEVATTELDIAGASSTDYVNVVNACLNQPKG
gi|119500612|ref|XP_001267063.1|            SQTHL-----------ALTALASSGVSEVATTELDIAGASSQDYVNVVNACLGVPKC
gi|402083948|gb|EJT78966.1|                 TQGHLQSGQG----SALAGAIKALADTGVKEVAVTELDIQNNANDYAAVTKGCLAVKSC
gi|121818962|sp|Q4JHP5.1|XYNC_ASPTE         SQTHLGSCGS----WTVEDAINTTASSGVSEVAITELDIAOASSTDYVNVNACLSVSKC
gi|202435633|sp|Q0CBM8.2|XYNC_ASPTN         SQTHLGSGGS----WTVEDALNTLASSGVSEVAITELDIAGASSTDYVNVVNACLSVSKC
```

TABLE 6.2-continued

Multiple alignment of FveXyn4 and homolog sequences

```
                                              1         10        20        30        40        50        60
                                              |         |         |         |         |         |         |
gi|6690415|gb|AAF24127.1|AF127529_1            SQTELSAGQG----ASVLQALPLIASAGTPEVAITELDVAGASSTDYVNVVNACLNVQSC
gi|380719871|gb|AFD63136.1|                    SQTHLGSGGS----WTVKDALNTLASSGVSEVAITELDIAGASSTDYVNVVNAGLSVSKC
gi|345505465|gb|ARN99940.1|                    TQCHLAGPGGWNTAAGVPDALKALAAANVKEIAITETDIAGASANDYLTVMNACLQVSKC
gi|157834036|pdb|1TUX|A                        SQTHLSACQG----ASIDAALPNTASAGTPEVAITELDTAGATSTDYVEVVNACLDVDSC
gi|380482707|emb|CCF41074.1|                   SQAELQANQG----GNALGALQTLAGSGVKEVAITELDIVGASTNDYTAVTRACLQVRQC
gi|13432255|sp|P23360.4|XYNA_THEAU             SQTHLSAGQG----AGVTQALRLLASAGTPEVAITELDVAGASPTDYVNVVNACLNVSSC
gi|3915310|sp|O59859.1|XYN2_ASPAC              SQTHLSAGAG----AAVSGALNALAGAGTKEVAITELDIAGASSTDYVNVVKACLNQPKC
gi|28373360|pdb|1I1W|A                         SQTHLSAGQG----ASVLQALPTLASAGTPEVAITETDVAGASSTDYVNVVNACLNVSSC
gi|358384163|gb|EHK21815.1|                    TQTHLSAGGG----ASTQGALQQLATAPVTELAITELDIAGAPSNDYNAVVQGCLSVAKC
gi|292495278|sp|A2QFV7.1|XYNC_ASPNC            SQTELSAGGG----AGISGALNALAGAGTKETAVTELDIAGASSTDYVEVVEACLNQPKC
gi|292495635|sp|C5J411.2|XYNC_ASPNG            SQTHLSAGGG----AGISGALNALAGAGTKETAVTELDTAGASSTDYVEVVEACLNQPKC
gi|342887934|gb|EGU87360.1|                    IGITVWGVSDKNSWRKEHDSLLFDANYNPKAAYTAVVNALR-
gi|29811371|gb|AAC06240.1|                     IGITVWGVSDKNSWRKEEDSLLFDANYNFKAAYTAVVNALR-
gi|408392452|gb|EKJ71807.1|                    VGITVWGVSDKDSWRKEKDSLLFNAQYQAKPAYTAVVNALR-
gi|46139945|ref|XP_391663.1|                   VGITVWGVSDKDSWRKEKDSLLFNAQYQAKPAYTAVVNALR-
gi|50844272|gb|AAT84258.1|                     VGITVWGVSDKDSWRKEKESLLFNAQYQAKPAYTAVVNALR-
gi|302893580|ref|XP_003045671.1|               VGITVWGVRDQDSWRTGENPLLEDNNYSPKEAYDAVVQALR-
gi|302404956|ref|XP_003000315.1|               KGITVWGVSDKDSWRQGTNPLLFDADYNPKAAYTAINTKLS-
gi|76160800|gb|ABA40421.1|                     VGITVWGVSDRDSWRSGSSPLLFDSNYQPKAAYNATIAAL--
gi|346979854|gb|EGY28206.1|                    KGITVWGVSDKDSWRKGANPLLFDGDYNPKAAYTAIVTKLS-
gi|292495638|sp|Q0H904.2|XYNC_ASPFU            VGITVWGVSDRDSWRSGSSPLLFDSNYQPKAAYNAIIAAL--
gi|310798877|gb|EFQ33770.1|                    VGITVWGVRDPDSWRAQNNPLLFDANWNPKAAYNAVVSALQ-
gi|310797994|gb|EFQ32887.1|                    VGISVWGVRDSDSWRTGANRITFDANFQPKQAYNAVAQVIG-
gi|339633727|ref|XP_003714516.1|               VGITAWGVRDNDSWRPQGNPLLFDSNYNPKAAYNSVVQALK-
gi|304442883|gb|ADM34973.1|                    VGITVWCVSDNDSWRSQKSRCTFQRNYNVKPAYNAITTAL--
gi|321150383|gb|ADW66245.1|                    VGITVWGVSDNDSWRSDESPCLEDRNYNVKPAYNAITAAL--
gi|121707433|ref|XP_001271831.1|               IGITVWGVSDKNSWRKENSPLTFDRNYNPKAYNAIIAAL--
gi|292495637|sp|B0Y6E0.2|XYNC_ASPFC            VGITVWGVSERDSWRSGSSELLFDSNYQPKAAYNAIIAAL--
gi|7328942|dbj|BAA92882.1|                     VGITVWGVSDENSWRSAESPLLFDGNYQPKTAYNAILNAL--
gi|74664704|sp|Q96VB6.1|XYNF3_ASPOR             VGITVWGVSDKNSWRSAESPLLFDGNYQPKSAYNAILNAL--
gi|165908534|gb|ABY71931.1|                    VGITVWGISDKDSWRASTNRLTEDSNFNPKPAYNSTVSTLQ-
gi|169159203|dbj|BAG12101.1|                   VGITVWGVADPDSWRASSNPLLEDGNYNPKAAYNAIANAL--
gi|119500612|ref|XP_001267063.1|               VGITVWGVSDKDSWRSSSSPLLFDSNYQPKAAYNAIIAAL--
gi|402033948|gb|EJT78966.1|                    VGITVWGVRDQDSWRPQGNPLLFDSGFNAKANYNAIVQALQ-
gi|121818962|sp|Q4JHP5.1|XYNC_ASPTE             VGITVWGVSDKYSWRSNDKPLLEDSNFQPKAAYNAIISAL--
gi|292495633|sp|Q0CBM8.2|XYNC_ASPTN            VGITVWGVSQKYSWRSNDKPLLFDSNFQPKAAYNAIISAL--
gi|6690415|gb|AAF24127.1|AF127529_1            VGITVWGVADPDSWRASTTPLLEDGNENPKPAYNAIVQDLQQ
gi|380719871|gb|AFD63136.1|                    VGITVWGVSDKYSWRSNDKRTTFDSNFQPKAAYNATTSAL--
```

TABLE 6.2-continued

Multiple alignment of FveXyn4 and homolog sequences

```
                                             1         10        20        30        40        50        60
                                             |         |         |         |         |         |         | gi|345505465|gb|AEN99940.1|                  VGITVWGVEDEDSWRSSSNRLLFDSNYQFKAAYNATINAL--
gi|157834036|pdb|1TUX|A                      IGITVWGVADPDSWRASTTPLLFDGNFNPKPAYNAIVQLL--
gi|380482707|emb|CCF41074.1|                 VGITVWGVRDPDSWRAQNNPLLFDANWNPKAAYNAVVQALQ-
gi|13432255|sp|P23360.4|XYNA_THEAU           VGITVWGVADPDSWRASTTPLLFDGNFNPKPAYNAIVQDLQQ
gi|3915310|sp|O59859.1|XYNA_ASPAC            VGITVWGVADPDSWASSSSPLLFDSNYNPKAAYTAIANAL--
gi|28373360|pdb|1I1W|A                       VGITVWGVADETSWRASTTPLLFDGNFNPKPAYNAIVQNLQQ
gi|358354163|gb|EHK21815.1|                  WGITVWGISDKDSWROGTNPLLFDSNFNPKPAYNSIVSILQ-
gi|292495278|sp|A2QFV7.1|XYNC_ASPNC          IGITVWGVADPDSWRSSSTPLTFDSNYNPKPAYTAIANAL--
gi|29249563.5|sp|C5J411.2|XYNC_ASPNG         IGITVWGVADPDSWRSSSTPLLFDSNYNPKPAYDAIANAL--
```

The invention described and claimed herein is not to be limited in scope by the specific aspects herein disclosed, since these aspects are intended as illustrations of several aspects of the invention. Any equivalent aspects are intended to be within the scope of this invention.

Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A xylanase polypeptide variant having at least 90% sequence identity with SEQ ID NO:2 which comprises a substitution at productive amino acid position 79 corresponding with the amino acid residue position of the amino acid sequence shown in SEQ ID NO:2, wherein said substitution increases the thermostability of the polypeptide without significantly reducing the specific activity, pepsin resistance and expression of the polypeptide, and wherein the xylanase variant meets at least one of the following criteria:

a. Relative performance (Performance Index, PI) for specific activity in at least one of the two activity assays I and II is greater than 0.8, PI for pepsin resistance is greater than 0.9 and PI for thermostability assay 1 is greater than 1.2 or PI for thermostability assay 2 is greater than 1.5;

b. Relative performance (Performance Index, PI) for specific activity in at least one of the two activity assays I and II is greater than 0.5, PI for pepsin resistance is greater than 0.8, and PI for Thermostability assay 1 is greater than 1.2 or PI for thermostability assay 2 is greater than 1.3; or c. Relative performance (Performance Index, PI) for specific activity in at least one of the two activity assays I and II is greater than 0.9, PI for pepsin resistance is greater than 0.9, and PI for Thermostability assay 1 is greater than 1.0 or PI for thermostability assay 2 is greater than 1.0;

and said substitution is selected from the group consisting K079Y, K079I, K079L, K079F, K079V, K079M.

2. The xylanase variant of claim 1 wherein the xylanase in an endo-1,4-β-xylanase.

3. An enzyme composition comprising a xylanase polypeptide variant of claim 1.

4. A feed additive composition comprising a xylanase polypeptide variant of claim 1.

5. A premix comprising a xylanase polypeptide variant of claim 1 and at least one vitamin and/or at least one mineral.

6. The feed additive composition according to claim 4 which further comprises a phytase.

7. A feed or feedstuff comprising a xylanase polypeptide variant of claim 1.

8. A method of preparing a feedstuff comprising admixing a feed component with a xylanase polypeptide variant of claim 1.

9. A method for degrading xylan in a xylan-containing material, comprising admixing said xylan-containing material with the xylanase polypeptide variant according to claim 1.

10. The method of claim 9, wherein the xylan-containing material is insoluble xylan (AXinsol).

11. The method of claim 9, wherein the xylan-containing material is selected from one or more of the group consisting of: a feed or feedstuff; a feed component; a grain-based material; a mash; a wort; a malt; malted barley; an adjunct, a barley mash; and a cereal flour.

12. The method of claim 9, wherein the xylan is solubilized without increasing viscosity in the reaction medium.

13. The method of claim 11, wherein the feed or feedstuff or feed component comprises or consists of corn, Distillers Dried Grain Solubles (DDGS), corn based Distillers Dried Grain Solubles (cDDGS), wheat, wheat bran or a combination thereof.

14. The method of claim 11, wherein the feed or feedstuff is a corn-based feedstuff.

15. The method of claim 9, wherein the xylanase is used in combination with one or more of the enzymes selected from the group consisting of endoglucanases; celliobiohydrolases, β-glucosidases, cellulases, lichenases, lipases, lipid acyltransferases, phospholipases, phytases, amylases, other xylanases, glucoamylases, hemicellulases, proteases, debranching enzymes, cutinases, esterases and mannanases.

16. The method of claim 9, wherein the xylanase is used in combination with one or more of the enzymes selected from the group consisting of a protease, an amylase, and a phytase.

17. The method of claim 9, wherein the method is or is part of a wheat gluten-starch separation process.

18. The method of claim 9, wherein the method is or is part of a biofuel or biochemical production process.

19. The method of claim 9, wherein the method is or is part of a malting or brewing process.

20. A premix comprising the enzyme composition of claim 3, and at least one vitamin and/or at least one mineral.

21. A premix comprising the feed additive composition of claim 4 and at least one vitamin and/or at least one mineral.

22. The premix of claim 5 which further comprises a phytase.

23. A feed or feedstuff comprising the enzyme composition of claim 3 or the feed additive composition of claim 4 or 6 or the premix of claim 5.

24. A method of preparing a feedstuff comprising admixing a feed component with the enzyme composition according to claim 3 or the feed additive composition of claim 4 or 6 or the premix of claim 5.

* * * * *